United States Patent
Schmutzer et al.

(10) Patent No.: US 9,173,803 B2
(45) Date of Patent: *Nov. 3, 2015

(54) INTEGRATED INFUSION MANAGEMENT SYSTEM

(71) Applicant: MEDICAL EQUIPMENT SYSTEMS, INC., Fort Collins, CO (US)

(72) Inventors: Stephen E. Schmutzer, Fort Collins, CO (US); Robin Richard Slaton, Fort Collins, CO (US); Christopher Pullen, Fort Collins, CO (US); Lucas Weidner, Loveland, CO (US)

(73) Assignee: Firefly Medical, Inc., Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/804,337

(22) Filed: Mar. 14, 2013

(65) Prior Publication Data
US 2013/0270799 A1 Oct. 17, 2013

Related U.S. Application Data

(60) Continuation of application No. 13/367,645, filed on Feb. 7, 2012, now Pat. No. 8,534,616, which is a division of application No. 11/961,834, filed on Dec. 20, 2007, now Pat. No. 8,136,773.

(60) Provisional application No. 60/883,205, filed on Jan. 3, 2007.

(51) Int. Cl.
*F16M 11/00* (2006.01)
*B60B 33/00* (2006.01)
(Continued)

(52) U.S. Cl.
CPC ............... *A61H 3/04* (2013.01); *A61M 5/1415* (2013.01); *A61M 5/1417* (2013.01); *B60B 3/048* (2013.01);
(Continued)

(58) Field of Classification Search
CPC .... A61H 3/04; A61M 5/1415; A61M 5/1417; B60B 33/0044; B60B 33/0049; B60B 33/006
USPC ........ 248/121, 25.8, 129, 157, 166, 170, 171, 248/188, 2, 5, 7, 434, 309.11; 280/32.5, 280/47.2, 651, 652; 5/503.1, 600, 658; 297/338, 423, 12, 488; 180/6.5, 19.3, 180/21, 22
See application file for complete search history.

(56) References Cited

U.S. PATENT DOCUMENTS
907,171 A * 12/1908 Poles et al. ...................... 211/62
D45,770 S 5/1914 Shaw
(Continued)

FOREIGN PATENT DOCUMENTS
JP S49-062892 6/1974
JP H01-284250 11/1989
(Continued)

OTHER PUBLICATIONS
Australian Patent Examination Report for Australian Application No. 2007342126, Issued Jul. 25, 2012.
(Continued)

*Primary Examiner* — Tan Le
(74) *Attorney, Agent, or Firm* — Lathrop & Gage LLP

(57) ABSTRACT

An integrated infusion management system provides for stable support of components attached to the system, even when the system is mobile. The system is optionally a mobility assist or walker for a patient who is attached to any number of medical components. A central trunk connects to a two-sided base that does not interfere with patient motion. The trunk may be angled with respect to vertical and oriented to support medical components in a configuration that is tip-resistant. The system is optionally deployable to facilitate conversion between a compact storage configuration and a stable deployed configuration. In an embodiment, additional deployable features include holding arms for holding various medical components, wheels, mobility arms and handles. Also provided is a novel wheel system with deployable wheels and methods associated with providing compact storage of any one or more of the systems presented herein.

20 Claims, 41 Drawing Sheets

(51) Int. Cl.
*F16M 11/20* (2006.01)
*A61H 3/04* (2006.01)
*A61M 5/14* (2006.01)
*B60B 3/04* (2006.01)

(52) U.S. Cl.
CPC ......... *B60B 33/0023* (2013.01); *B60B 33/0039* (2013.01); *B60B 33/0049* (2013.01); *B60B 33/0055* (2013.01); *B60B 33/0073* (2013.01)

(56) References Cited

U.S. PATENT DOCUMENTS

| | | | |
|---|---|---|---|
| 1,612,148 A * | 12/1926 | Oettinger | 211/85.6 |
| 2,583,114 A | 1/1952 | Monteith | |
| 2,596,055 A | 5/1952 | Thomas | |
| 2,794,612 A | 6/1957 | Clifton | |
| 2,795,387 A * | 6/1957 | Elsey | 248/520 |
| 3,437,296 A | 4/1969 | Hinz | |
| 3,533,583 A | 10/1970 | Azim | |
| 3,719,789 A | 3/1973 | Harnden, Jr. | |
| 4,251,044 A | 2/1981 | Olson | |
| 4,332,378 A | 6/1982 | Pryor | |
| 4,341,381 A | 7/1982 | Norberg | |
| 4,541,596 A * | 9/1985 | Price | 248/125.8 |
| 4,725,027 A | 2/1988 | Bekanich | |
| 4,744,536 A | 5/1988 | Bancalari | |
| 4,807,837 A | 2/1989 | Gawlik et al. | |
| 4,832,294 A | 5/1989 | Eidem | |
| 4,867,273 A | 9/1989 | Schaevitz | |
| 4,892,279 A | 1/1990 | Lafferty et al. | |
| 4,905,944 A | 3/1990 | Jost et al. | |
| 4,907,794 A | 3/1990 | Rose | |
| D310,570 S | 9/1990 | Wells | |
| 5,167,389 A | 12/1992 | Reimers | |
| 5,411,044 A | 5/1995 | Andolfi | |
| 5,458,305 A | 10/1995 | Woodward | |
| 5,479,953 A | 1/1996 | Pasulka | |
| 5,526,894 A | 6/1996 | Wang | |
| 5,556,065 A | 9/1996 | Wadley | |
| 5,617,958 A * | 4/1997 | Laug et al. | 211/85.7 |
| 5,622,344 A | 4/1997 | Gracie | |
| D385,348 S | 10/1997 | Ward et al. | |
| 5,704,577 A | 1/1998 | Gordon | |
| 5,772,162 A | 6/1998 | Lin | |
| 6,056,249 A | 5/2000 | Fillon | |
| D434,495 S | 11/2000 | Whalen | |
| 6,161,850 A | 12/2000 | James et al. | |
| D436,167 S | 1/2001 | Ebert | |
| 6,226,833 B1 | 5/2001 | Kawaguchi et al. | |
| 6,296,260 B1 | 10/2001 | Schiavone | |
| 6,296,263 B1 | 10/2001 | Schultz et al. | |
| D457,239 S | 5/2002 | Kunik | |
| 6,430,761 B1 | 8/2002 | Brandorff et al. | |
| 6,467,797 B1 | 10/2002 | Lofy et al. | |
| D479,164 S | 9/2003 | Wu | |
| 6,619,599 B2 | 9/2003 | Elliot et al. | |
| 6,698,789 B2 | 3/2004 | Reimers et al. | |
| 6,839,939 B2 | 1/2005 | Donakowski | |
| D503,909 S | 4/2005 | Tolfsen et al. | |
| 6,899,660 B1 | 5/2005 | Chin et al. | |
| 6,969,031 B2 | 11/2005 | Ugent et al. | |
| 6,983,915 B2 | 1/2006 | Adelman | |
| D519,423 S | 4/2006 | Tolfsen | |
| 7,048,222 B1 | 5/2006 | Curtiss | |
| 7,065,812 B2 | 6/2006 | Newkirk et al. | |
| 7,118,079 B2 * | 10/2006 | Kung | 248/125.8 |
| 7,278,615 B2 | 10/2007 | Schubert et al. | |
| 7,353,731 B2 | 4/2008 | Lin | |
| D568,467 S | 5/2008 | Cottone | |
| 7,591,479 B2 | 9/2009 | Golias | |
| 7,634,824 B2 | 12/2009 | Gramkow et al. | |
| 7,726,327 B2 | 6/2010 | Battiston | |
| D622,377 S | 8/2010 | Jackson | |
| D627,063 S | 11/2010 | West et al. | |
| D628,691 S | 12/2010 | Sung et al. | |
| D630,731 S | 1/2011 | Schmutzer et al. | |
| 7,935,030 B1 | 5/2011 | Nesbitt | |
| 8,136,773 B2 | 3/2012 | Schmutzer et al. | |
| 8,534,616 B2 | 9/2013 | Schmutzer et al. | |
| 2003/0178538 A1 | 9/2003 | Hasloecher et al. | |
| 2005/0139736 A1 | 6/2005 | Breda et al. | |
| 2005/0230573 A1 | 10/2005 | Ligertwood | |
| 2006/0001226 A1 | 1/2006 | Refsum | |
| 2007/0267551 A1 | 11/2007 | Townsend | |
| 2008/0156946 A1 | 7/2008 | Schmutzer et al. | |
| 2008/0210831 A1 | 9/2008 | Considine | |
| 2011/0016628 A1 | 1/2011 | Masterson | |
| 2011/0023920 A1 | 2/2011 | Bolton | |
| 2011/0030749 A1 | 2/2011 | Miller | |
| 2011/0290979 A1 | 12/2011 | Henault et al. | |
| 2012/0133111 A1 | 5/2012 | Schmutzer et al. | |

FOREIGN PATENT DOCUMENTS

| | | |
|---|---|---|
| JP | 03-046338 | 4/1991 |
| JP | 3040162 | 8/1997 |
| JP | 2002-211405 | 7/2002 |
| JP | 2005-506244 | 3/2005 |
| JP | 2006-335355 | 12/2006 |
| WO | WO 2004/101034 | 11/2004 |
| WO | WO 2008/085698 | 7/2008 |

OTHER PUBLICATIONS

Final Rejection, Corresponding to Japanese Application No. P2009-544881, Dispatched Aug. 6, 2013—Japanese and English translation.
International Search Report and Written Opinion, Corresponding to International Application No. PCT/US2007/088433, Mailed Aug. 7, 2008.
Notice of Reasons for Rejection, Corresponding to Japanese Application No. P2009-544881, Dispatched Jul. 3, 2012—Japanese and English translation.
Office Action in corresponding Japanese Patent Application No. P2013-252977, dispatched Oct. 14, 2014 (with English translation)—9 pages.
International Search Report for PCT/US2014/047254 mailed Nov. 12, 2014—2 pages.
Blickman Catalog, Nezzie Ambulation Device, http://www.blickman.com/products/0429000000—3 pages, accessed Mar. 2, 2015.
LivenGood PACE, http://www.livengoodmed.com/—5 pages, accessed Mar. 10, 2015.
European Search Report and Opinion for Application No. EP2007869691 of Feb. 9, 2015—5 pages.

* cited by examiner

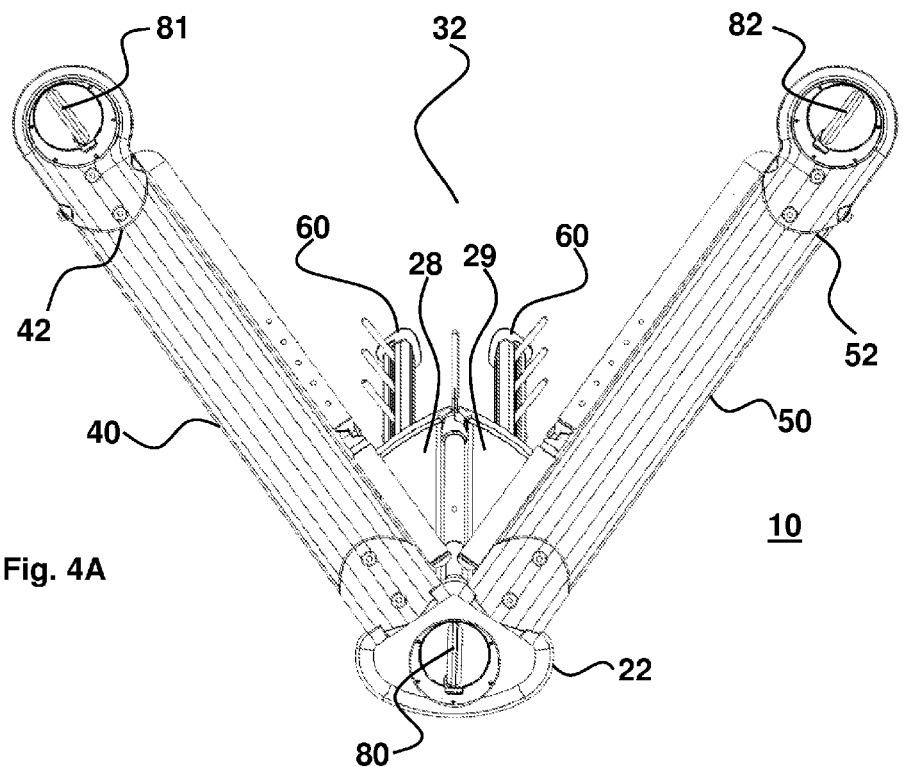
Fig. 4A
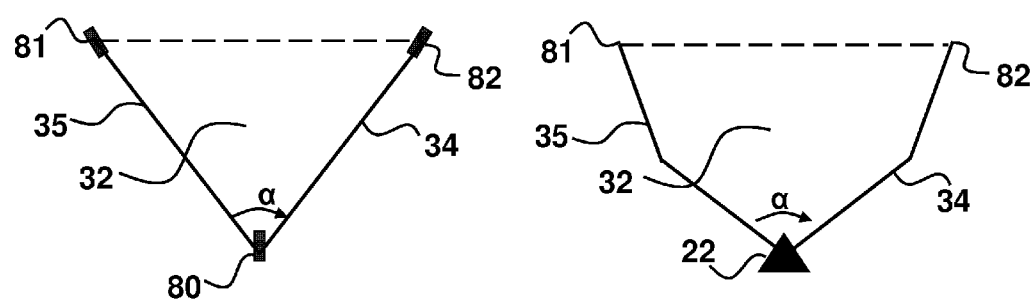
Fig. 4B
Fig. 4C

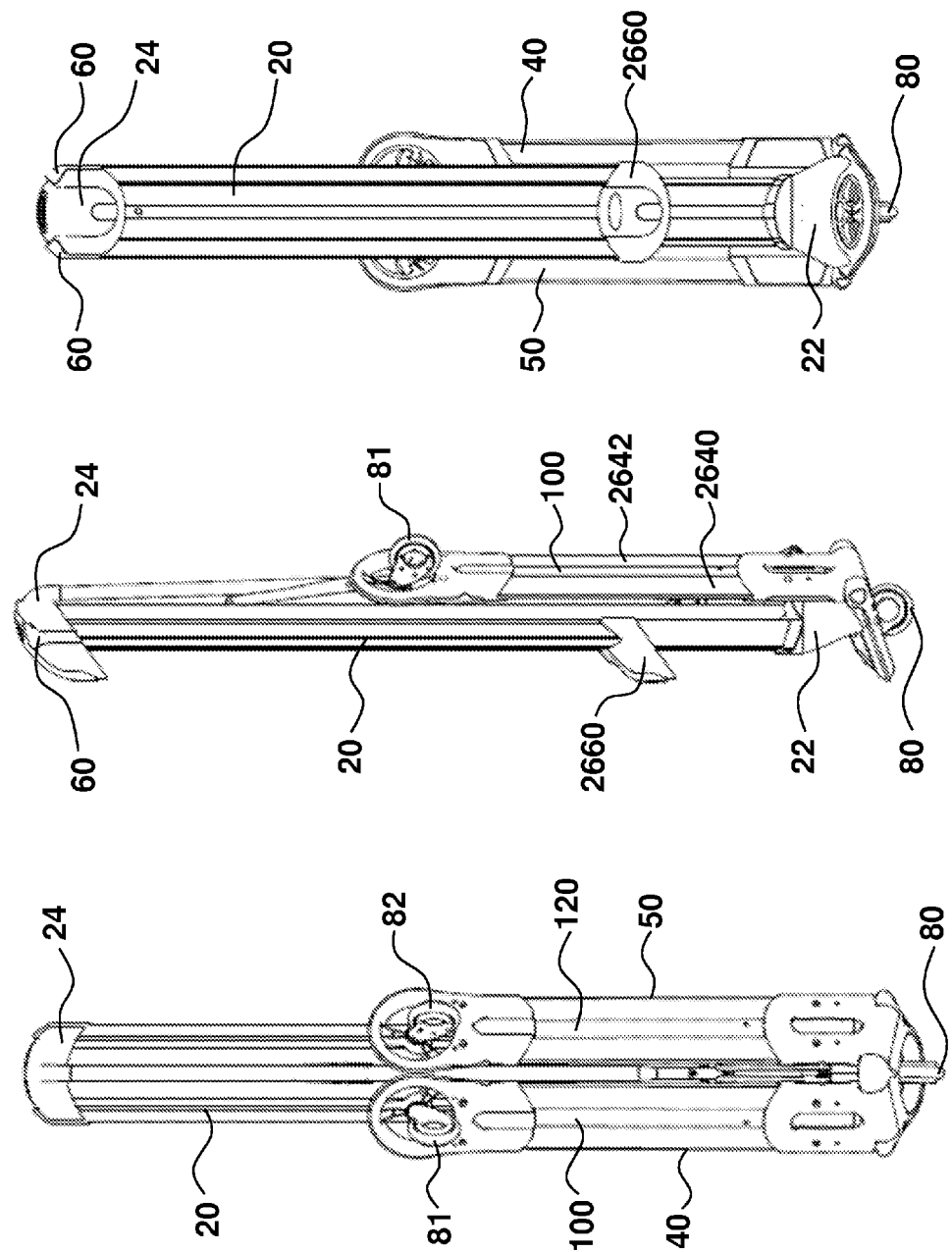

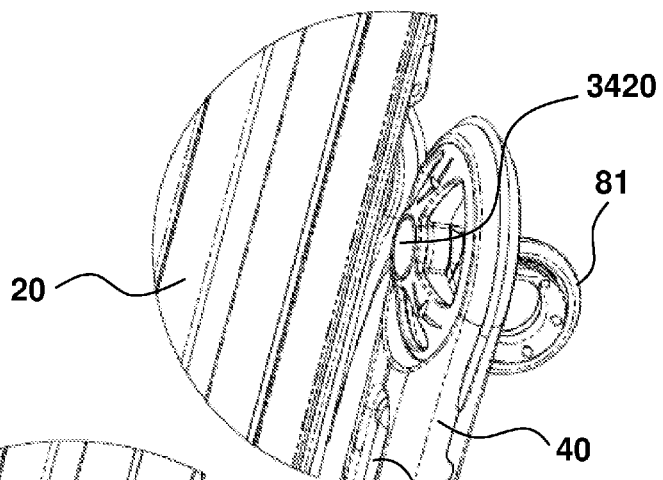
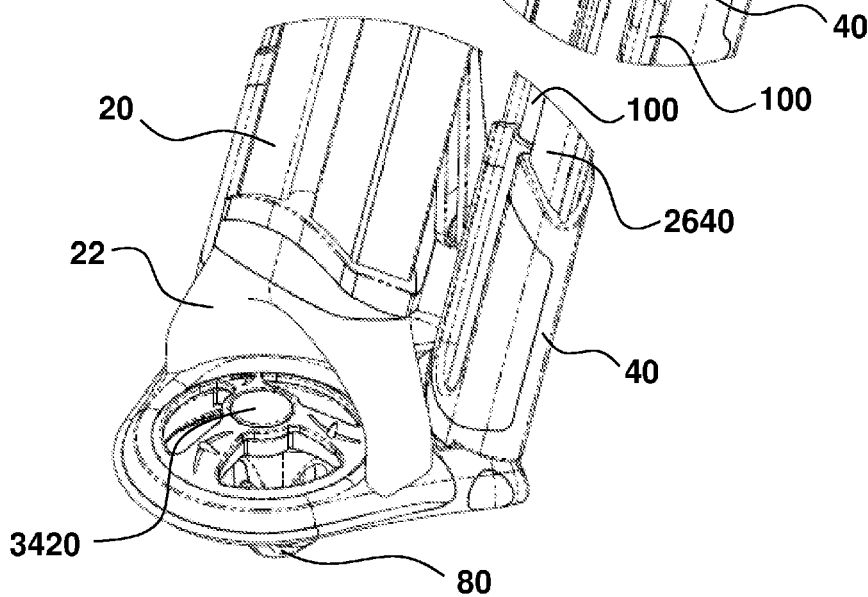

INTEGRATED INFUSION MANAGEMENT SYSTEM

CROSS-REFERENCE TO RELATED APPLICATIONS

This application is a continuation of U.S. patent application Ser. No. 13/367,645 filed Feb. 7, 2012, which is a divisional of U.S. patent application Ser. No. 11/961,834 (now U.S. Pat. No. 8,136,773), filed on Dec. 20, 2007, which claims benefit of provisional patent application 60/883,205 filed Jan. 3, 2007, each of which is hereby incorporated by reference to the extent it is not inconsistent with the present disclosure.

BACKGROUND OF THE INVENTION

The invention is generally in the field of a stable support stand capable of providing medical support to a patient and is optionally mobile and readily maneuverable by a patient to whom a medical device is connected. Disclosed herein are aspects related to a convenient and reliable systems for intravenous fluid supply systems that are capable of folding into a compact storage configuration, and can provide patient mobility assistance, such as a combination walker and infusion management system ("IMS"). In particular, the IMS is a radical improvement and departure over traditional intravenous ("IV") poles currently in use.

It is important for patient rehabilitation and recovery that a patient be able to walk, even when connected to a medical component, after a medical procedure (see U.S. Pat. No. 4,332,378). A walking patient, however, presents special safety problems in terms of ensuring the supporting pole is stable and does not tip or hinder the patient or caregiver when it is moving with the patient. This safety concern is not adequately addressed by current IV poles that have a vertical pole connected to a wheeled base. The IMS provided herein is designed to ensure medical components (including relatively heavy components) are easily attached to the IMS, and the IMS is extremely stable, maneuverable, and optionally capable of providing reliable physical support to a walking or moving patient. In addition, an IMS of the present invention is capable of folding into an extremely compact configuration when not in use.

Although the medical products and healthcare industries have undergone rapid development, the basic IV pole has remained relatively unchanged for most of the last century. They remain rigid, heavy, difficult to roll, unwieldy, ugly, easily tipped and nearly impossible to conveniently store when not in use. The IV poles known in the art generally require two-handed manipulation to appropriately configure the pole height to a specific patient and oftentimes the pole does not reliably lock at a certain height. The wheels of the poles often stop rolling or catch (such as on a rug or uneven surface transition between rooms), increasing the risk of pole-tipping, potentially causing serious injury and damage to valuable attached medication and equipment.

Another major drawback to the IV poles currently used is that they are very difficult to store. Generally, when not in use they are clustered together in a storeroom (or an unused patient room converted to a storage room), or at the end of a hall. This clustering results in a jumble of devices that may be difficult to access when a pole is needed, as well as occupying valuable hospital space that could be better utilized. This is not a simple problem because a typical hospital likely owns hundreds of IV poles. Even in smaller settings, such as doctors' offices, the presence of only a couple of IV poles can present serious storage issues.

Wheeled pole support systems used in clinical settings are generally known in the art (e.g., see U.S. Pat. Nos. 6,056,249, 4,744,536, 4,892,279, 4,725,027, 6,619,599, 5,772,162, 5,458,305, 4,905,944, U.S. Pub. No. 2005/0139736). One common limitation of each of those pole systems is that the central vertical pole configuration in combination with the conventional base structure is inherently unstable and ill-suited for holding heavy medical components. Components are generally connected to the IV pole by clamping or connecting them to the central vertical pole. This configuration is more prone to tipping because the center of gravity inherently shifts toward the perimeter of the base as equipment and accessories are added. In addition, the long lever arm and the height of suspended components result in a large lever arm which acts to exacerbate the inherent instability of the system, especially in view of how such systems are maneuvered. Accordingly, the configuration of the IV poles known in the art is prone to tipping, especially for a moving system whose wheels have a tendency to catch on surface disturbances.

IV poles currently used are also extremely ineffective walkers and do not provide any mobility assistance to a user. To walk with an IV pole, the patient grips the central pole with one hand, and cannot rely on the pole for support because the pole can easily and rapidly roll in an unwanted or unpredicted direction. This reflects the fact that a force-couple is created by having to maneuver the IV pole with only one hand, where the pole is generally located beside the user, and in a direction that is not inline with the direction of motion of the user. Therefore, the inertia of the IV pole is not inline with the direction of motion of the user. This creates the aforementioned force couple. Accordingly, the user must exert additional force/effort to move the IV pole and has a reduced ability to correct the IV pole in the event it tips or begins to tip. This problem increases as the mass or weight of the IV pole increases, such as by the connection of medically-needed components such as infusion pumps, for example. In addition, the base configuration that contains the wheels can interfere with patient walking and are easily caught on cracks (e.g., elevators) or other disturbance, further increasing instability.

Ambulatory patient support stands are generally known in the art (U.S. Pat. Nos. 6,969,031, 4,332,378). Those stands, however, still suffer from being inherently unsteady and unwieldy in that the wheeled base remains attached to a central pole and the patient still relies on the central pole for support. Accordingly, those systems remain unstable, unable to hold multiple heavy components, and do not easily fold for storage or deploy for use.

The fact that IV poles are inherently terribly designed for providing walking support is recognized in U.S. Pat. No. 5,704,577 where a walker-IV stand coupler is disclosed for connecting a traditional four-wheeled walker with an IV pole. That system, however, is unwieldy and complicated, requiring three different components that occupy a significant amount of space.

Walkers known in the art (U.S. Pat. Nos. 5,479,953, 5,411,044) have been adapted to receive an IV pole and/or IV solution bags. Those walkers, however, are relatively bulky four-wheeled systems that are not easily stored and do not have the capability and features of the present invention. Other walkers that may be collapsible for storage (e.g, U.S. Pat. No. 4,251,044) are not able to hold multiple heavy components, do not provide reliable physical support for an ambulating patient and/or are relatively difficult for a patient to maneuver.

Portable IV stands for field-use (U.S. Pat. Nos. 4,807,837, 6,983,915) and other types of stands having special caster wheel mechanisms (U.S. Pub. No. 2003/0178538, U.S. Pat. No. 2,794,612 for tripod with caster wheel mechanisms) are known in the art. Those stands, however, do not address the need for stable, easily deployable patient mobility assistance systems and infusion stands provided herein.

SUMMARY OF THE INVENTION

Conventional IV pole systems suffer from stability and/or storage deficiencies. Provided herein are a variety of geometrical configurations that provide increased stability and resistance to tipping under a variety of load and use conditions. Another feature disclosed herein is the capability of storing the variously configured systems in a compact and space-saving manner that is both convenient and easy to use. In addition, any of the systems provided herein are simple to maneuver and can assist with patient mobility, even for patients connected to any number of medical devices, including relatively heavy devices. These various one or more improvements are accomplished by radically redesigning the traditional IV pole geometry into an infusion management system ("IMS") having enhanced capabilities and features while being aesthetically pleasing. The base geometry generally provides a relatively large base area without interfering with either a caregiver's or patient movement. This is accomplished by providing a two-sided base having an open (e.g., notional) side across from a vertex from which the each of the two sides extend.

A safe, attractive and modern-looking system is important to help encourage patients to leave the bed and exercise by walking, thereby hastening recovery time after surgical or medical procedures. Optionally, the IMS is folded into a compact storage position for convenient storage, thereby minimizing the storage footprint when the IMS is not needed without sacrificing rapid availability and deployment when needed.

In an embodiment, the geometry of the IMS ensures that they stably roll and are extremely tip-resistant. The IMS can rapidly deploy (e.g., fold-out) to receive any number of components, irrespective of mass, that can be connected to a patient. In addition, the IMS is readily collapsible into a compact configuration for storage or is capable of nesting with other IMS to provide compact storage. Any of the systems and devices presented herein are optionally configured as a walker to support a walking patient or as a mobility assist device for providing easy and safe maneuvering for a patient. The various number of innovative features include one or more of deployable wheels, deployable base and trunk configuration, multiple deployable component supporting arms, holding arms, deployable holders, cable management system, integrated ambulation (e.g., walker or mobility assist) capability, storability, power supply, power strip and the flexibility to accommodate various accessories and/or upgrades. Accessories, such as calculators, written materials, device for dosage calculations, small instrument tables, light and light clips, reading light attachments, oxygen canister holder, wheel chair attachment, diagnostic equipment mounts are easily connected to the system.

In an embodiment, the invention is generally a system for holding one or more components that is extremely stable, even under heavy loads, and readily folds into a compact storage configuration. Similarly, the system is able to easily and quickly deploy into a position ready to receive one or more components, including relatively heavy components. In an embodiment, the system is an Infusion Management System (IMS) useful in a medical or clinical setting for administering intravenous (IV) fluids or other medical treatments that are performed on mobile persons and immobile persons and may be associated with IV administration, such as pumps, power sources, lights, oxygen administration/monitoring. In a specific embodiment, the IMS also is a walker that provides physical support to a patient that is walking and optionally connected to one or more medical components. Alternatively, the IMS may be a mobility assistance device, in that the system does not hinder a patient's ability to maneuver but instead is easily steerable and helps facilitate (rather than conventional systems that hinder) ambulation. The walker feature of the IMS is particularly useful as it provides an extremely stable platform upon which the patient can rely for support, even when heavy medical components are attached to the IMS and connected either directly or indirectly to the patient, without a concern of tipping or unexpected movements that are associated with traditional "straight-line" wheeled IV poles known in the art.

In an embodiment, the stability of the IMS is obtained by configuring the system to have a relatively large base footprint and ensuring that medical components attached to the IMS are located over a central region of the base footprint, in contrast to IV poles currently used, where the bottom base is circular and relatively small (e.g., smaller than an "arm's length" so the patient may grasp the central trunk). In an embodiment, the base comprises two base arms that are connected either directly or indirectly to the bottom of a trunk, wherein the base provides a relatively large (and therefore stable) footprint without interfering or obstructing the mobility or movement of a patient who maneuvers or walks with the IMS. This is achieved by having an "open-ended" base. Open-ended refers to one end of each of the base arms being free from connections (to from a notional edge of the base footprint that connects these free ends), with a vertex opposite the notional edge from which each of the base arms extend. In an aspect the trunk is vertical. In an aspect the trunk is angled relative to vertical. A large base footprint is obtained by constructing each of the two base arms to have a relatively long length and join at the trunk to form a base apex angle at the vertex region. In the embodiment where each of the base arms are straight, the base footprint is a triangle having a footprint area, $A_F=\frac{1}{2}*b*h$, where b is the separation distance of the ends of the base arms and $h=L*\cos(\alpha/2)$, where L is the length of the base arm, and $\alpha$ is the base apex angle. The particular dimensions are not critical, so long as the system remains stable and is capable of being maneuvered by a patient. Accordingly, in an embodiment the dimensions are such that a deployed device move through a door opening. Typical base arm lengths are between about 25 to 30 inches (64 cm to 76 cm), or any value therein. Typically, the base arms are separated by a maximum distance that is less than the width of a door in which the system must traverse, such as a conventional door width of about 36 inches (92 cm). From these parameters, the base apex angle or "vertex angle" $\alpha$ can be calculated.

The trunk to which medical components are connected (either directly by a holder or indirectly via a holding arm), is optionally angled in a direction so that the trunk extends over the base footprint, thereby ensuring the center of gravity of the deployed IMS, including an IMS to which multiple heavy medical components are attached, is located over the base footprint. A center of gravity over a relatively large base footprint that does not interfere with a user's stride, results in an extremely stable system that is very difficult to tip, but capable of easy and reliable maneuverability. A conventional circular base footprint, in contrast, must be rather small (e.g., certainly less than a patient's arm length) to not interfere with the patient's stride, thereby resulting in inherent instability.

In the embodiment where the IMS is deployable, the system comprises a trunk for holding one or more medical components, and a base comprising a first base arm and a second base arm, wherein one end of each of the base arms is pivotally connected to the trunk bottom end, wherein in a base-deployed configuration the trunk optionally forms an acute angle relative to the base; and in a base-storage configuration each of the base arms pivot to a position parallel to the trunk. The IMS is designed so that the trunk angle and position relative to the base footprint ensures the trunk is located over the base footprint, and preferably a central region of the base footprint. Alternatively, where the trunk is vertical, an extended vertex region past where the trunk meets the base (e.g., where the extension is distal to the trunk), provides for a center of mass located over the base footprint, wherein the base that defines the base footprint does not interfere with the patient's stride.

Deployable base refers to a base that is capable of being positioned to provide a stable (e.g., "folded-out" or "deployed") IMS and is also capable of being positioned to provide a compact (e.g., "folded-in" or "stored") IMS for storage. In an embodiment, in the base storage configuration each of the base arms are positioned in a manner that is parallel to the trunk. In this aspect, parallel encompasses paired surfaces that are within about 20° of parallel. In an embodiment the base arms are parallel to the trunk but not touching the trunk. In an embodiment the base arms are parallel to the trunk and touching a trunk surface in at least one axial location. In an embodiment, substantially the entire length of the base arm contacts a trunk surface.

In an aspect, the trunk has three major surfaces extending between the trunk bottom and top ends, a front surface and two side surfaces, wherein each side surface receives a base arm when the system is positioned in its base storage configuration. In this aspect, a trunk surface has a surface shape that is substantially complementary to a base arm top surface, so that the shaped trunk surface receives one base arm when the system is in the base storage configuration.

In an aspect, the IMS is capable of ambulating over a surface, such as by providing three or more wheels that stably contact the surface "Stably contacting" refers to the device and wheels being situated such that the center of gravity of the system is within the base footprint defined by the points of contact of the at least three wheels and the device does not tip under an applied force to the handles and/or when medical components are supported by the holders. The IMS is mobile by connecting three or more wheels to the base, wherein the base comprises the base arms and the portion of the trunk bottom surface or vertex region that is opposed to the surface on which the IMS rests. For example, any of the IMS disclosed herein can further comprise a first wheel connected to the trunk bottom end or to a vertex region formed by the connection point (e.g., vertex) between the base arms, a second wheel connected to the first base arm and a third wheel connected to the second base arm. Connecting each of three wheels to appropriate positions on the base results in a stable system that can ambulate over a supporting surface under an applied force, for example a directional force applied by a patient and/or medical person. Maximum stability is obtained by connecting the wheels to the end of the base arm that is furthest from the wheel that is connected to the trunk bottom or vertex region, or in other words, by maximizing the magnitude of the base area footprint. This can be further accomplished by locating the wheel in the vertex region that is distal to where the trunk connects to the base. Such a configuration further provides an easily-maneuvered system, wherein the open-ended base footprint does not obstruct or interfere with a patient's stride, in contrast to conventional IV pole bases that are not open-ended.

In an embodiment, each of the wheels are connected to the system by casters, such as hubless casters or conventional casters, to facilitate automatic wheel swiveling that aligns the wheels in the direction from which the system is pushed or pulled. In an embodiment, all (three) wheels swivel allowing the IMS to be easily positioned or moved. When the mobility arms (or "handle arms") are deployed to their "walker position" and are ready to support a person during ambulation, the rear wheels optionally lock in a forward direction. This "locking" prevents the IMS from uncontrolled shifting toward the side, and facilitates a person to ambulate in the forward direction. The front wheel under the trunk continues to caster or swivel which facilitates controllable steering of the IMS. In an embodiment, the rear wheels are capable of swiveling when the mobility arms are in a stored position but lock in a fixed direction (e.g., do not to swivel) when the mobility arms deploy. In an embodiment, each of the wheels swivel irrespective of the status of the mobility arms.

Any of the wheel or wheel systems connected to the IMS may be deployable to ensure maximum compactness during storage. When the IMS is not in walker mode, the wheels may be stored to ensure the IMS remains in a fixed position. In this aspect, a deployed wheel is capable of rolling over a supporting surface, and in a storage position the wheel is positioned such that it does not contact the supporting surface, or contacts in such a manner that it cannot roll over the surface. In an embodiment, each of the wheels swivel (e.g. capable of "directional rotation") when deployed. Directional rotation refers to the wheel being able to freely swivel to orient in the direction of an applied force. Three swiveling wheels facilitate maximum maneuverability for when the system is not supporting a patient in a walker mode. In an alternative embodiment, only the front wheel is able to swivel when deployed, and the two rear wheels deploy in a fixed direction. Alternatively, each of the wheels deploy in a fixed direction. In an aspect, the second and third wheels (e.g., the rear wheels) deploy in a direction substantially parallel to the forward direction. In this aspect, substantially parallel refers to the wheel positioned in a direction that is within 20° of true parallel. In an embodiment, the rear two wheels are capable of swiveling when the mobility arms are in a stored position, but lock in a fixed direction when the mobility arms are deployed. This aspect is useful because in the mobility arm deployed position, the system can be used as a walker and it is important that the rear two wheels are incapable of sudden changes in direction to ensure the walking patient is appropriately supported. This aspect is achieved by a caster-locking assembly that lockably engages the wheel component that swivels, such as a rotable ring mount connection, when the mobility arms are rotated into a deployed position.

Any of the ambulatory IMS embodiments can further comprise a pair of handles for receiving a force to ambulate or move the IMS. The handles are optionally pivotally connected to allow the handle to be positioned substantially parallel to the base arm for storage when the handle is not needed and deployed substantially perpendicular to the base arm for receiving a force from a patient or caregiver when the IMS is ambulating. Each handle can have a handle grip configured (e.g., comfortable rubber material) to receive a force from a hand, for example. For sanitation reasons, the handles or handle surface on which a patient's hands are placed may be disposable, thereby facilitating replacement as needed.

In an embodiment, the handle further comprises a mobility arm pivotally connected to the base arm, a grip joint that connects the handle grip to the mobility arm, and a handle lock assembly lockably engaged with the mobility arm, whereby said mobility arm can be locked in storage or deployed position. In this embodiment, a release button conveniently positioned on the IMS, such as on the base arm, is pressed to release the ambulation or mobility arm allowing it to be deployed into its deployed position or to be stored in its storage position In an aspect, the handle and more specifically the mobility arm (also referred herein as a "mobility handle"), comprises two sections telescopingly connected for adjusting the length of the mobility arm to facilitate use of the walker by patients of different heights or by a standing patient and one confined to a wheelchair. In this aspect, the mobility arm further comprises an upper arm portion and a lower arm portion telescopingly connected to each other. In another embodiment, the handle has a grip joint with means for selectably positioning the grip handle. In the embodiment where the mobility handles are deployable, the mobility handles may connect to the base arms by any means known in the art such that in a stored position the mobility handles are not available for use. For example, the mobility handles may be rotably connected to the base arm so that during storage the handles are substantially parallel to the base arms. This can be on an inner, top or outer surface. Alternatively, the base arms may have a recess feature for receiving the mobility handles, so that the handles are substantially within the base arm during storage. In an aspect, the recess is formed by having a portion of the base arm length be split into two. Another example of storability relates to the complete removal of the mobility arm, such as by threaded, magnetic, or tight-fitting connections that are made to facilitate reversible or temporary connection of the mobility and base arms.

The particular point of connection of the mobility handle to any of the devices or systems presented herein is not critical, so long as the mobility, stability and maneuverability of the system remains satisfactory. For example, in certain embodiments the point of connection is on a base arm that tends to be relatively far from the trunk. In other embodiments the point of attachment may be at the trunk or at the vertex region. For example, a single connector may connect to the trunk at one end, and at the other end a pair of mobility handles may connect. Alternatively, a pair of mobility handles may connect to and extend from the trunk. In an aspect, the mobility handles are generally located in an area that corresponds to the vertical space above the base footprint area.

In an embodiment, the trunk indirectly supports medical component(s) by connecting to holding or folding arms that support the medical components. This type of medical component support mechanism, rather than direct medical component attachment to the trunk, is extremely flexible in terms of component positioning, easy-to-use, and capable of supporting a large number of components and provides maximum compact storage when the IMS is not in use. In an aspect, each of the holding or folding arms is itself deployable.

In an aspect, the IMS has a holding arm telescopingly connected to the trunk top end for holding medical components so that the holding arm is height-adjustable. The IMS can further comprise a holding arm lock assembly lockably engaged with the holding arm, whereby the holding arm can be locked in storage or deployed position with one hand. In particular, the lock assembly facilitates positioning of the holding arm with a variety of holding arm lengths. The lock assembly can further comprise a button that moves a member out of a recess in the holding arm thereby permitting movement of the holding arm relative to the trunk top end. When the desired position is reached, the button can be released so that the member engages another recess in the holding arm, thereby securely positioning the holding arm. In an aspect, this locking mechanism button is located on the trunk top surface. In another aspect, provided is a holder that is operably connected to both the trunk and one or more holding arms. The handle is movable along at least a portion of the axial length of the trunk. A latch-type mechanism is provided so that the handle (and therefore the holding arm) is capable of locking and unlocking the handle the handle moves as desired, thereby adjusting the maximum height of the holding arm. This provides a means for "infinite" height adjustability of one or more medical components supported by the holding arm(s).

In an aspect, the holding arm further comprises one or more holders for holding one or more medical components. Alternatively, holders may connect directly to the trunk. The holders themselves can be positionable, thereby providing further control of where the medical component(s) are attached relative to the IMS trunk. The holders can be deployable, removable or both. In an embodiment, the holders are positioned in a groove that runs at least a portion of the length of the holding arm. The groove can contain a system for one-handed holder manipulation, wherein the holder can be connected to the groove in a manner that allows placement or positioning of the holder when the holder is manipulated, and the holder is firmly positioned when the holder is not manipulated. The groove may comprise a series of spaced receptacles for mating with a holder, such as a ladder recess and relief pattern and/or may employ a ratchet mechanism. The groove system is particularly useful for receiving pump shaft mounts. In an embodiment, the groove is capable of receiving the plurality of positionable holders. To provide secure attachment of medical fluid bags to the holders, the holder can have one end shaped or contoured (e.g., hooks), such that relief and/or recess features receive the medical fluid bag. The holders are capable of holding any component that needs to be in proximity to a patient and is useful in providing medical treatment.

In an embodiment, the holding arm is three-sided with each of the three sides having a groove running in a longitudinal direction for receiving at least one holder. In this aspect, longitudinal direction refers to the long-axis direction of the holding arm. This three-sided system provides additional flexibility in locating and positioning medical components attached to the IMS. In an embodiment, the IMS comprises a pair of holding arms, with each holding arm independently telescopingly connected to the trunk top end. Alternatively, each of the two holding arms are controlled by a single handle located in a slideable engagement with the trunk.

In another aspect of the invention, the IMS further comprises a folding arm or "collapsible support", "pump mount" or, more generally, "mount". The collapsible support provides an additional or alternative site for connecting medical components. The collapsible support is connected to the trunk at both collapsible support ends, in contrast to the holding arm that has one end that is telescopingly connected to the trunk top end. The attachment sites are preferably located in a position that is opposite the trunk front and between the two trunk side surfaces. In the exemplified embodiment, the collapsible support has a bottom collapsible support section capable of telescoping between a stored position and a deployed position for receiving medical components. For example, a spring button is capable of lockably engaging with a corresponding hole so that the trunk and lower collapsible support are "locked." The collapsible support section has a bottom end deployably connected to the trunk bottom end and a top collapsible support section with a top end deployably connected to the trunk top end. The bottom and top arm sections are connected by a folding joint. Similar to the holding arm, the collapsible support is capable of attaching a plurality of deployable holders, and specifically holders that are connected to the top collapsible support section for attaching a medical component. The collapsible support also has a means for deploying and storing the collapsible support, wherein in a stored position the collapsible support is parallel to the trunk, including contained within a collapsible support groove in the trunk that separates two side trunk surfaces. The means for deploying the collapsible support facilitates rapid and easy positioning of the collapsible support away from the trunk for receiving one or more medical components. Means for deploying the collapsible support includes, but is not limited to, a small ring located at the elbow for transmitting a force. When a deploying force is applied to the ring (e.g., ring is pulled), the lower telescoping collapsible support section extends and a button mates with a hole in the shaft, thereby locking the system into a deployed configuration. Alternatively, a pair of springs or other tension providing means is provided, such that the collapsible support is under tension when stored, and when a force is applied to the joint in a direction away from the trunk, the arm unfolds and deploys. Alternatively, the collapsible support ends can have a positionable connection with the trunk (e.g., slide and lock mechanism). In another aspect, this pump mount or collapsible support is automatically deployed when the base arms are deployed. This is achieved by operably connecting the pump mount to the base arms such that pivotal motion of the base arms relative to the trunk causes a corresponding pump mount or collapsible support motion.

The trunk of any of the systems claimed has a trunk optionally shaped to have three major surfaces, a front face and two side faces to which the base arms are substantially parallel when the base arms are positioned in a storage configuration. In an embodiment, the front face has an axial trunk groove in which a cord or tubing of a medical component may be disposed. One or more clips can be operationally connected to the trunk groove, including rotably connected, for organizing or holding cords or tubing associated with the components attached to the IMS. In an embodiment, the collapsible support is positioned within a collapsible support groove located between the two trunk side faces. For an automatically deployable pump mount (collapsible support), the operable connection between the mount/support and the base arm(s) can be along a trunk surface or contained within the interior volume defined by the trunk surfaces.

In an aspect, the IMS further comprises an electrical system for providing power to electrical components that are attached to the IMS. The electrical system comprises at least one electrical outlet capable of supplying electrical power to a medical component attached to the system. The electrical outlet can be located anywhere on the system that is convenient for supplying electrical power to an electrical component, for example on a base arm top surface or trunk surface. In an embodiment, one or more electrical outlets are located on the trunk side surface(s) or the trunk front surface. The electrical system connects to a power source, wherein the electrical power is AC, DC, or both. AC power can be supplied by a conventional wall outlet connected to the electrical system (e.g, a power strip) by a conventional AC power cord and plug. In addition, DC power can be supplied by a battery, such as a primary or secondary battery. The ability to power the system with a DC portable power source is particularly important for the embodiment where the system is ambulating, so that a continuous source of electrical power is available even when the system is not connected to a wall outlet. The DC power source can be a battery that is attached to the system. In an aspect, the electrical system includes a rechargeable battery and means for charging the rechargeable battery from an external power source. The means for charging includes a cord connected to an ac plug for connecting to an ac outlet, a cord connected to a dc plug for connecting to a dc outlet, and the various associated circuitry known in the art for ensuring efficient and safe battery charging from these sources. The rechargeable battery can be an integral component of the IMS, such as positioned within the trunk or a trunk recess. Alternatively, the battery can be attached to one of the holders of the IMS.

The trunk of the present invention can have any of a variety of shapes, so long as the trunk and base arms are capable of relatively compact storage when the base arms are positioned substantially parallel to the trunk. Accordingly, the trunk has an axial or longitudinal direction selected from the group consisting of angled, curved and linear. In an aspect the trunk is angled or curved. An angled or curved trunk is useful for positioning the IMS near objects such as a bed, gurney, tables and dressers, for example. In an aspect the trunk is linear. A linear trunk is the simplest geometry and can yield the most compact configuration suitable for wall-hanging storage or placement within a cart capable of holding a plurality of IMS of the present invention. In an aspect, a plurality of systems may nestle within each other for compact storage without a need for rotating the base relative to the trunk.

In an embodiment, the IMS is also a mobility assistance device capable of being maneuvered by a walking patient who is connected to, or must have readily available, one or more medical components. In this aspect, the IMS device comprises a trunk having one or more holders for holding one or more medical components, wherein the trunk has a bottom end and a top end. Axially spaced holders can be connected directly to the trunk or indirectly to the trunk by a holding arm and/or collapsible support or pump mount ("mount") described herein. A base, having a first base arm and a second base arm wherein one end of each of the base arms is connected to the trunk bottom end, is connected to the trunk. To provide IMS mobility, a first wheel is connected at the vertex region or near the trunk bottom end, a second wheel is connected to the first base arm end, and a third wheel is connected to the second base arm end, wherein each of the wheels are capable of stably contacting a supporting surface on which the system rests. The points of contact between the wheels and supporting surface provides a stable triangular base footprint over which the trunk extends. Additional wheels may be employed as necessary. Mobility arms for supporting a walking patient, and in a specific embodiment receiving a patient's hand, are connected to each of the base arms for supporting a patient's hand. The patient is able to move the system in a direction by applying appropriate force to each of the handles or mobility arms. The system is able to provide stable support to the walking or moving patient and is also tip-resistant, even with one or more heavy components attached to the system.

In an embodiment, each handle (or mobility arm) of the IMS walker is rotably connected to the base arms to allow the handles to be rotated into storage or deployed position. In another aspect providing further deployability capability, each of the base arms are pivotally connected to the trunk for pivoting each of the base arms into base-storage or base-deployed configuration. Alternatively, the mobility arms are reversibly connected to the base arms. Optionally, additional attachments can be provided so that a caregiver may also apply an ambulating force to the walker. Examples include strategically placed handles and/or handle attachments for connecting tethers or cords.

Any of the systems described herein can be of any appropriate dimension or shape, so long as the system is stable and resistant to tipping even when relatively heavy components are attached to the system and is sized so that the system can be used in hallways, through doors, etc., as desired. For example, the trunk can have at least a portion that is linear, with the linear portion having an angle relative to vertical. The angle relative to vertical is any suitable angle, including an angle selected from a range of between about 5° and about 25°, 10° and 15°, or about 12°, thereby ensuring the trunk, and more particularly components supported by the trunk, is positioned over a central portion of the base footprint. The vertical distance between the top and bottom ends of the trunk can have a range selected to match the height of a user (e.g., child versus adult). For example, the vertical height (e.g., distance of top end from the floor) is selected from a range of between about 3' and 6', 4' and 5', or about 4.5'. The telescoping support provides additional vertical height, such as a height selected from a range of between about 1' and 2', or about 18". Accordingly, the total vertical height of the trunk plus telescoping support in an exemplified embodiment is about 6'.

The base footprint of the IMS and IMS walker systems of the present invention with wheels deployed is triangular, with each vertex corresponding to the contact point between the wheel and supporting surface. The particular trunk and base arm geometry are dependent on each other so that the deployed system is extremely stable. In an embodiment, the base arms have a length selected from a range of between about 2' to 3.5', 30" to 36", or about 3'. The base footprint corresponds to about the area between the base arms and for base arms of 36" length and vertex angle of 70° is about 610 in$^2$.

In another aspect, any of the systems described and claimed have a base vertex angle selected from the range of 40° to 100°, 50° to 90°, or about 70°, where the base vertex angle is defined by the angle formed by the directions of the first and second base arms, and particularly the directions of the base arm ends adjacent to the trunk bottom. An important aspect of the invention is that even for an IMS having a large base footprint and capable of holding a significant number of components, when not in use the IMS is capable of folding into a compact configuration having dimensions that are only slightly greater than the dimensions of the trunk. For example, when folded for storage, the footprint of the device can be as small as the horizontal cross-section of the trunk, or about the cross-section of the trunk plus the cross-sections of each of the base arms in their stored position. In contrast, the footprint of the deployed IMS corresponds to the area defined by the deployed base arms. Accordingly, in an aspect the stored footprint is less than 20%, less than 10%, or less than 5% the deployed footprint.

The invention further provides methods related to the IMS and IMS walkers disclosed herein. In an embodiment, the invention is a method of simultaneously providing medical treatment and supporting a patient while walking by providing an infusion management walker system of the present invention. The medical components that provide medical treatment are attached to the holders of the walker system and each of the mobility arms are rotated to a position suitable for receiving force from a walking patient. A patient who wishes to walk while connected to the medical component(s) is positioned behind the system (e.g., in the base area region generally defined as between the second and third wheels attached to the base arms) and each of the patient hands are positioned on the handle grip. The patient can walk with the IMS walker and ambulate the IMS walker by applying a force to the handle grip and thereby simultaneously receive medical treatment and receive walking support from the IMS walker. This method provides a stable IMS that is much more resistant to tipping or uncontrolled movement then traditional IV poles and is capable of preserving the patient's line of sight during ambulation. In an aspect, the medical component that is attached to the IMS is selected from the group consisting of an intravenous fluid container (e.g., IV bags), catheter and drainage bags, testing equipment, infusion pumps, a power supply, an optical source, oxygen canisters, monitoring equipment or any medical item whose use may be facilitated by proximity to a patient.

Also provided are methods for compactly storing an infusion management system, such as by providing an IMS having a trunk connected to a base, wherein the base comprises a pair of base arms that pivotally connect to the trunk. Pivoting the base to a position that is substantially parallel to the trunk provides compact storage of the infusion management system. The system is then available to be stored where convenient, such as by mounting to a wall or ceiling mount. Alternatively, any of the systems provided herein are stored by nesting adjacent devices in a manner similar to how conventional carts are nested (e.g., close proximity and stacking of the devices).

The invention is also a specialized, wheeled-system to ensure a safe and easy-to-use walker IMS. The wheel system of the present invention is optionally hubless and/or deployable. The wheel system comprises a bearing that facilitates rotation of an outer wheel portion that contacts the surface over which the wheel rolls, and an inner wheel portion that does not itself rotate when the outer wheel is rolling. The bearing can be any bearing known in the art such as ball bearings and roller bearings, so long as the outer wheel portion is capable of rotating without any inner wheel rotation. Alternatively, the wheel is of an open-hub design.

In an embodiment, the invention is a deployable wheel system having a ring mount with an inner facing surface that defines a central orifice. A wheel holder is rotably connected at one end to the inner-facing surface of said ring mount and connected to a wheel at the wheel holder other end. The wheel itself is a "hubless wheel" having an outer portion and an inner portion, wherein the outer portion is rotably connected to the inner portion, and the wheel holder is rigidly connected to the wheel inner portion. This configuration allows the wheel outer portion to roll over a surface, and the wheel holder is capable of deploying the wheel in a deployed position or a stored position. In the wheel stored position, the wheel is said to be aligned with the ring mount, wherein the wheel is generally concentric to the ring mount and the wheel outer portion is covered by the ring mount. In the wheel deployed position, the wheel is not aligned with the ring mount, and a significant portion of the wheel outer surface is not covered by the ring mount and is available for contacting and rolling over a supporting surface.

In an aspect, the ring mount has an outer facing surface that is attached to a wheel cover. The wheel cover has an end that is available for connecting to a device, including a medical device, a table or stand, or a generic holder such as a bicycle holder, for example. The other end of the cover can be curved and shaped as desired, including curved and shaped to cover the wheel, thereby minimizing injury arising from incidental contact with the wheel. The ring mount connection between the ring mount and wheel cover is optionally rotably connected, thereby providing swivel capability to the wheel (e.g., a wheel caster that aligns with the direction of applied force).

The wheel systems of the present invention are particularly useful when connected to a piece of medical equipment. The wheel systems of the present invention can be connected to a device arm by any means known in the art, including by slidably engaging the device arm into a hollow opening at the wheel cover connecting end. Alternatively, the wheel cover can be an integral part of the device arm (e.g., by injection molding, casting, etc), or permanently affixed to the device by fasteners, adhesives and/or welds. In the exemplified embodiment, the wheel cover receives a base arm of an intravenous pole (including the IMS of the present invention) and fasteners securely connect the base arm and wheel cover.

In an embodiment, the wheel system further comprises a wheel swivel lock assembly lockably engaged with said ring mount outer surface, whereby said ring mount can be locked in a direction thereby preventing wheel swivel. This embodiment is useful for providing straight-line walkers while retaining the ability to deploy a more maneuverable walker as needed.

In another aspect, the wheel system comprises a wheel lock assembly lockably engaged with the wheel outer portion, whereby the wheel is capable of locking in stationary position, thereby preventing wheel rotation over a supporting surface. In an embodiment, the IMS comprises a wheel system having a controlled braking system to provide a range of friction a user must overcome in order to move the IMS. In an embodiment the braking system comprises a hand-brake similar to a hand brake commonly used on bicycles. The hand-brake comprises a rubber pad that brakingly engages a wheel, a lever attached to the handle grip of the mobility arm and a cable running between pad and lever for transmitting lever depression by the user to rubber pad motion to brakingly engage the wheel. Alternatively, for IMS users who may have difficulty generating sufficient force to engage a hand-brake, a throttle grip is used, wherein rotational displacement of the grip provides wheel friction adjustment. In an embodiment, the IMS comprises a means for braking the wheels, such as by the controlled braking lever and throttles discussed herein, operator-assisted brakes such as a foot clip, lever, dial and other mechanisms providing controllable braking friction. The braking system provides the ability to vary IMS movement from free rotating to locked in position.

BRIEF DESCRIPTION OF THE DRAWINGS

FIG. 4: A Bottom view of the IMS of FIG. 1. B Schematic illustration of the base footprint defined by the triangle having each apex corresponding to the contact point between the wheel and surface on which the IMS is resting. C shows a base footprint for when the wheels are stored and not contacting the surface and for base arms that are angled.

FIG. 35 Various views of the system of FIG. 26 in a stored position. A is a front view; B is a side view; C is a rear view.

FIG. 38 is a close up view of the various wheel portions of the system in a stored position illustrated in FIGS. 35-36. A shows the end-portion of the base arms. B shows the trunk bottom portion, vertex region, and other end-portion of the base arms.

DETAILED DESCRIPTION OF THE INVENTION

Figure 1:
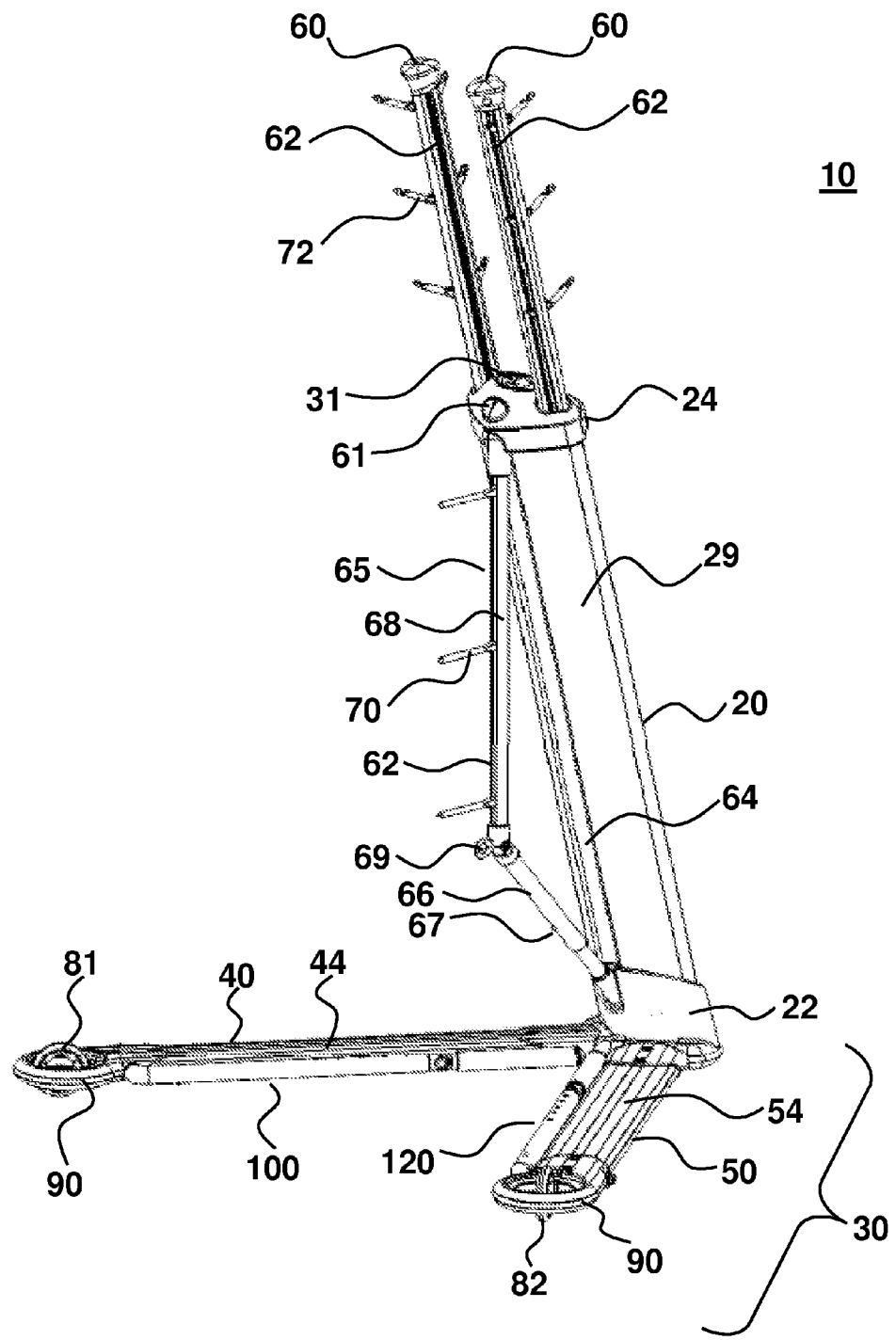
FIG. 1: Perspective view of the infusion management system (IMS) with base deployed. The handles for receiving a force from a patient are in a stored position. The lines on the base arm surface indicate surface contour.

Referring to the drawings, like numerals indicate like elements and the same number appearing in more than one drawing refers to the same element. In addition, hereinafter, the following definitions apply:

The invention has a number of innovative features related to one or more of stability, foldability, and maneuverability. For example, the systems provided herein can replace conventional intravenous (IV) pole by providing improved stability and maneuverability during ambulation, compact storage when not in use. The base footprint combined with the location of the trunk allows for a patient to ambulate without interference from any of the base arms, trunk, or components connected to the system. A v-base and angled trunk embodiment create a stable platform for hanging a large number of heavy devices and/or materials to the system while maintaining their ability to connect or interface with the patient. In an embodiment where the system is mobile, the system facilitates connection of a large number of medical accessories to a patient without sacrificing stability or control when the patient is walking.

"Trunk" refers to the central shaft or pole to which any number of components (e.g., medical components) can be held or attached. The trunk may be vertical, substantially vertical, or angled with respect to vertical. "Substantially vertical" refers to plus or minus 5° from vertical (e.g., 90° relative to the base). A trunk having at least a portion that is angled with respect to vertical to provides further stability to the system, even when multiple relatively heavy components are attached to the system. If an angle formed by the trunk and base is less than 90°, that angle is said to be "acute". In an aspect, the trunk is linear (e.g., not bent or curved). In an aspect the trunk is bent or curved.

"Base" refers to the portion of the system that rests on a supporting surface (e.g., a floor). In the exemplified embodiment, the base comprises a pair of base arms with each base arm pivotally connected to the trunk bottom end. "Pivotally connected" refers to a base that is deployable with respect to the trunk. Accordingly, when the base arms are folded-out the arms are positioned at an angle relative to the trunk and the system is ready for supporting one or more medical components. When the base arms are folded-in they are positioned substantially parallel to the trunk and the system is relatively compact and ready for storage. As used herein, "parallel" refers to a longitudinal direction of the base arm being within at least 5° of true parallel with respect to the longitudinal direction of the trunk. "Substantially parallel" refers to the longitudinal directions of the axis or the surfaces being within at least 30°, at least 15°, or at least 5° of parallel.

Many features of an IMS are said to be deployable. "Deployable" refers to the component being "folded-in" (positioned) to make the component or system more compact for storage, or "folded-out" (positioned) to make the component or system ready for use. Alternatively, deployable refers to a portion of the system that can be removed or connected to the device as needed.

In the embodiment where the trunk is a straight shaft, the base arms can have correspondingly straight geometry, with the base arms forming a base arm apex angle corresponding to the vertex located at the trunk where each of the arms are pivotally connected. In the embodiment where the trunk is angled or curved, each of the base arms are preferably correspondingly angled or curved to ensure maximum compact storage of the system when the base arms are pivoted to a position parallel to the trunk. Although it is preferred, for maximum compactness, the base arms and trunk have similar longitudinal geometry, the invention tolerates mismatch in geometry without undue loss in the ability to compact the system when not in use.

The contact points between the base and the surface on which the base rests define the edges of a base footprint. "Base footprint" refers to the area defined by the contact points between the base and the supporting surface and a notional line running from the base arm ends that are not attached to the trunk (e.g., the open-ended portion of the base footprint). A "two-sided" footprint refers to a configuration where there is an open-ended side opposite the vertex region from which each of the base arms extend. When three wheels are deployed, this area is triangular. When the base arms contact the surface, the area may be triangular (e.g., each of the base arms are linear), or can have a more complex shape (e.g., U-shaped, v-shaped or multi-angled shaped), with each side having a shape corresponding to a non-linear base arm, and a third notional straight-line that joins the base arm ends that are not attached to the trunk.

An aspect of the present invention is an infusion management system capable of ambulating over a supporting surface. "Ambulating" refers to a system that can move over a surface, and particularly a system capable of functioning as a mobility assist or walker for a patient that is connected to one or more medical components. In addition to the system functioning as a walker, the system is also constructed to ensure medical support personal can readily maneuver the system that is deployed or stored and optionally connected to one or more medical components. "Medical component" refers to a material, device, or structure useful in providing medical treatment to a patient including, but not limited, bags of fluid such as intravenous (IV) fluid, infusion pump, optical sources, power supplies, platforms for holding medical components, oxygen monitor, oxygen canisters, etc.

"Holding" or "attaching" a medical component to the IMS encompasses passive hanging (e.g., a bag suspended by a holder), orienting the holders to more securely receive the component, shaping the hanger to provide relief and recess features to facilitate secure holding as well as more complex connections such as a male-female connection with an adaptor connected to the devices (e.g., threaded screws, one-handed quick connects, snap-beads, etc.). Optional accessories such as light sources, calculator, computer, video screens, power supplies can be more permanently attached to and/or in the trunk surface.

The core system (e.g., trunk and base arms) itself can be made from any of a number of materials including, but not limited to, traditional chrome, any metal or metal composites, fiberglass, plastics, carbon fiber, and/or composite material.

The system preferably has rounded edges and corners to minimize the chance of injury arising from inadvertent contact with the system and may have rubber-like bumpers or protecting strip to minimize unwanted impact arising from accidental contacts. In addition, the system can be designed to be aesthetically pleasing, having dramatic sweeping arms with striking color, sharp and clean lines to reassure patients who are uncertain about ambulating.

"Caster" is used to refer to a wheel mounted with an offset steering pivot such that the wheel will automatically swivel to align itself to the direction from which it is pushed or pulled. Typical caster systems known in the art are commonly found on shopping carts, rolling chairs and other movable objects (see, e.g., Hamilton Caster & Mfg. Co., Hamilton, Ohio). The wheel system of the present invention is optionally a hubless caster (see U.S. Pat. No. 6,839,939 for a hubless caster assembly) and deployable.

Unless explicitly otherwise defined herein, "substantially" refers to a value that deviates less than about 10% from the true value.

All references cited throughout this application, for example patent documents including issued or granted patents or equivalents; patent application publications; and non-patent literature documents or other source material are hereby incorporated by reference in their entireties, as though individually incorporated by reference, to the extent each reference is not inconsistent with the disclosure in this application (for example, a reference that is partially inconsistent is incorporated by reference except for the partially inconsistent portion of the reference).

Every formulation or combination of components described or exemplified herein can be used to practice the invention, unless otherwise stated.

Whenever a range is given in the specification, for example, a size range or an angle range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein may be practiced in the absence of any element or elements, limitation or limitations which is not specifically disclosed herein.

One of ordinary skill in the art will appreciate that materials and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Example 1

IMS Geometry

The infusion management system (IMS) in its most basic configuration comprises a base 30 having a first 40 and second 50 base arm connected to a trunk 20 (FIG. 1). FIGS. 1-6 show an IMS in the base deployed configuration 10. Base arms 40 and 50 are connected to trunk 20 bottom end 22. The trunk 20 has at least an axial portion corresponding to a non-zero angle relative to vertical and an acute angle relative to base arms 40 and 50. This geometry is summarized in FIG. 2B, with the acute angle formed between trunk 20 and base arm 40 (or 50) labeled as $\theta$ and the non-zero angle relative to vertical labeled as $\phi$. In the exemplified embodiment of FIGS. 1-6 (e.g., three wheels deployed), the wheels 81 and 82 attached to base arms 40 and 50, and wheel 80 attached to trunk bottom 22 form a base footprint 32 that is triangular (e.g., see top and bottom views in FIGS. 3 and 4B). Base footprint 32 refers to the triangle defined by the contact point between each of the three wheels and surface on which the wheels rest, for the embodiment when the wheels are deployed (FIG. 4B). The sides 34 and 35 of base footprint triangle corresponds to base arms 40 and 50 for the straight base arm embodiment depicted in FIG. 4A. The exemplified embodiment shows a base 30 having a "v-shaped configuration." The base apex angle, $\alpha$, is defined as the angle formed by the base arms 40 and 50 at the trunk bottom, 22 (see FIG. 4B).

When the wheels are in a stored position (e.g, see FIG. 22), the base footprint corresponds to the contact points between the base arms 40 and 50 and trunk bottom 22 with the surface on which the base arms and trunk bottom rest (FIG. 4C). The invention encompasses non-linear base arm shapes including, but not limited to, curved, U-shaped, multiply-edged. FIG. 4C illustrates base arms that are angled (e.g., two-edged). Accordingly, in the wheels stored position, the base footprint can have more complicated non-triangular shapes whose edges correspond to the axial shape of the base arms 40 and 50. To ensure maximum compact storage, the shape of the trunk arm is preferably matched to the shape of the base arms, thereby ensuring parallel positioning of the base arms 30 and 40 to trunk 20 when the base arms are pivoted closed (compare FIGS. 2C and 4C). Accordingly, base footprint area can change depending on whether wheels are deployed (so that base arms do not contact the supporting surface (see FIG. 4B)) or stored (so that base arms do contact the supporting surface (see FIG. 4C)). FIG. 4C is an example of a multi-angled configuration base footprint, wherein a base arm can be made of individual segments having different axial orientation.

The base footprint 32 (for both wheels deployed and wheels stored) and angled relative-to-vertical ($\phi$) trunk 20 are important features of the present invention and ensures the center of gravity, even with one or more relatively heavy components attached to the system, is confined to a region within base footprint 32. Such a configuration ensures system 10 remains stable and tip-resistant even when it is ambulating and/or supporting a heavy load. Greater stability is provided by positioning holders 70 and/or 72 such that components are preferably located over a central region of base footprint 32, such as an area extending back from wheel 80 or trunk bottom 22 out to the notional line running between the ends of base arm 40 and 50 or wheels 81 and 82. In an aspect, a holder 70 may be connected directly to trunk 20.

The trunk 20, similar to the base arms 30 and 40, can also be non-linear. The exemplified embodiment illustrates a trunk that is linear, having an angle with respect to vertical ($\phi$) and horizontal ($\theta$) when base arms 40 and 50 are deployed to form base 30. The invention encompasses a trunk 20 that is curved or comprises more than one trunk section with each section having a unique angle with respect to horizontal. For example, the trunk can have a bottom section that is vertical (e.g., 90° angle with respect to horizontal) and an upper section that is angled with respect to horizontal, as illustrated in FIG. 2C. The trunk can have any axial shape/direction, so long as a significant portion of any suspended component is over the base footprint, thereby ensuring maximum stability and resistance to tipping. In an embodiment, the trunk 20 comprises three major surfaces, a trunk front surface 27, a first side surface 28 and a second side surface 29 (see FIGS. 3 and 4A).

Figure 3:
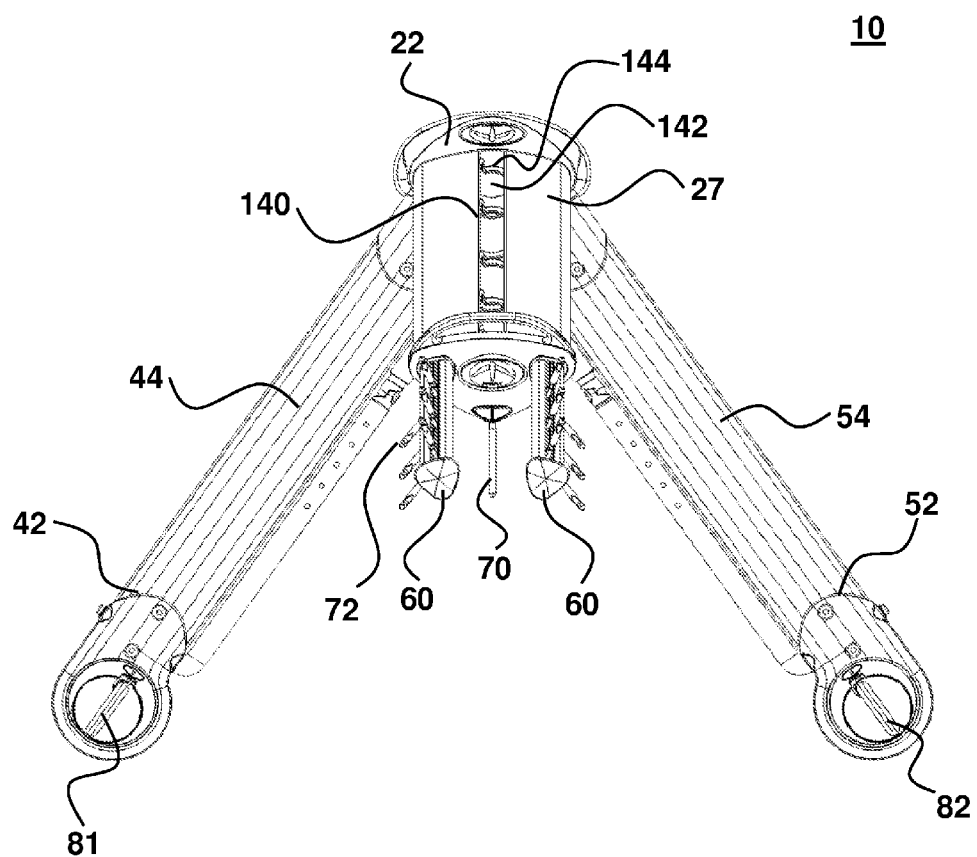
FIG. 3: Top view of the IMS of FIG. 1.

FIG. 3 illustrates that the front surface 27 of trunk 20 can further comprise a cord management system 140 for storing and organizing cords, including electric cords, component communication wires, and plastic IV tube lines. Cord management system 140 can comprise an opening 142 allowing cord placement within the trunk 20 body and optionally cord clips or organizers 144 for securably positioning cords or tubes. The cord management system can run substantially the entire length of trunk 20 or a portion thereof.

In the embodiment where the IMS facilitates patient ambulation, a plurality of wheels 79 are connected to the system 10. As shown in FIG. 4, a first wheel 80 is connected to trunk bottom end 22, and second and third wheels 81 and 82 and are connected to the end 42 or 52 of the base arm 40 or 50 by any means known in the art, such as by fasteners 87 (FIG. 19), adhesives, welds, etc. As discussed in the wheel example, in an aspect, each of the wheels is capable of orienting (e.g., swiveling) in any direction. This aspect is useful for patients who need not rely to a great extent on the system for support and also for situations where ease of maneuvering is required. In an alternative embodiment, wheels 81 and 82 deploy in a single fixed in a direction and wheel 80 is capable of swiveling. Optionally, each of wheels 81 and 82 are capable of swiveling, but upon activation of a wheel swivel locking mechanism each of wheels 81 and 82 are locked and unable to swivel. To ensure maximum patient safety, wheels 81 and 82 that can freely rotate in any direction (in response to a user changing direction), can optionally be locked in a user-specified direction, such as for example a substantially forward direction to facilitate straight-line walking upon deployment of mobility arms 100 and/or 120. Optionally, each of the one or more wheel systems has a braking mechanism brakingly engaged with the wheel for increasing the force required to roll or swivel the wheels, so that a patient must use a correspondingly greater pushing force to ambulate the system. Any such adjustable wheel-tensioning system that facilitates different amounts of friction encompassing complete braking to light brake application is particularly useful for patients first walking with the IMS.

Figure 13:
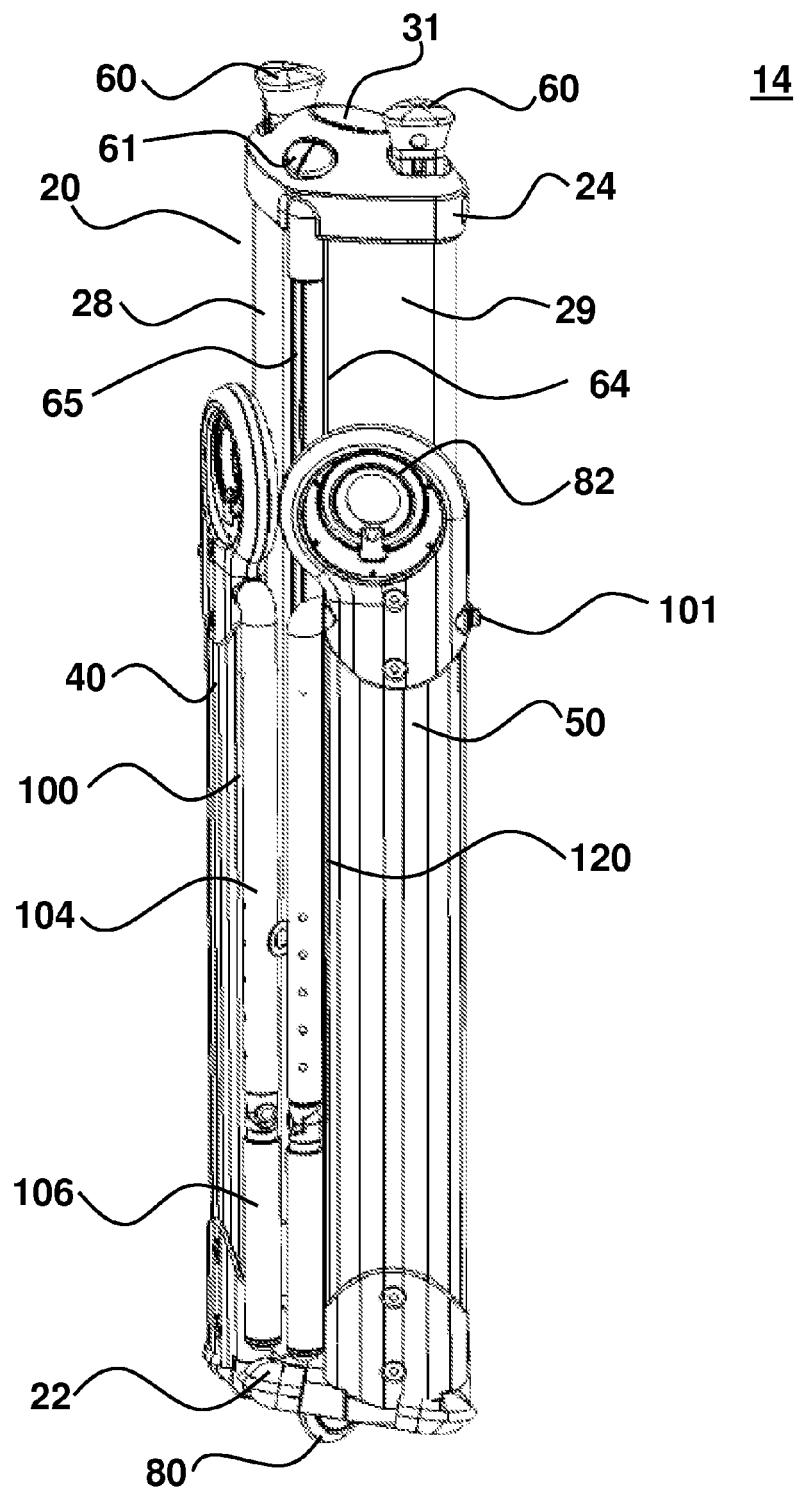
FIG. 13: Perspective view of the IMS in its storage configuration with base arms axially contacting the trunk.
Figure 14:
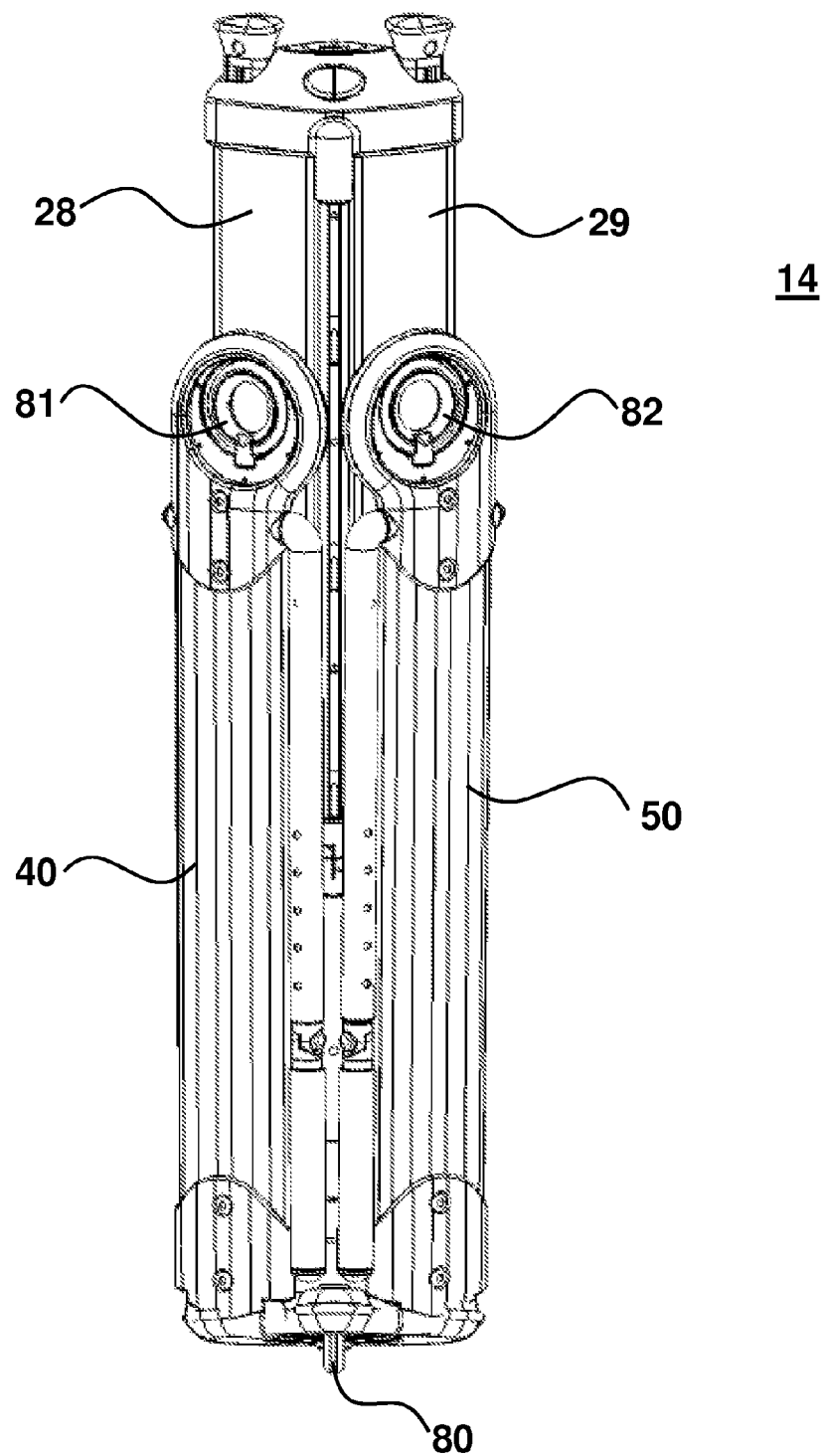
FIG. 14: Rear view of the IMS of FIG. 13.
Figure 15:
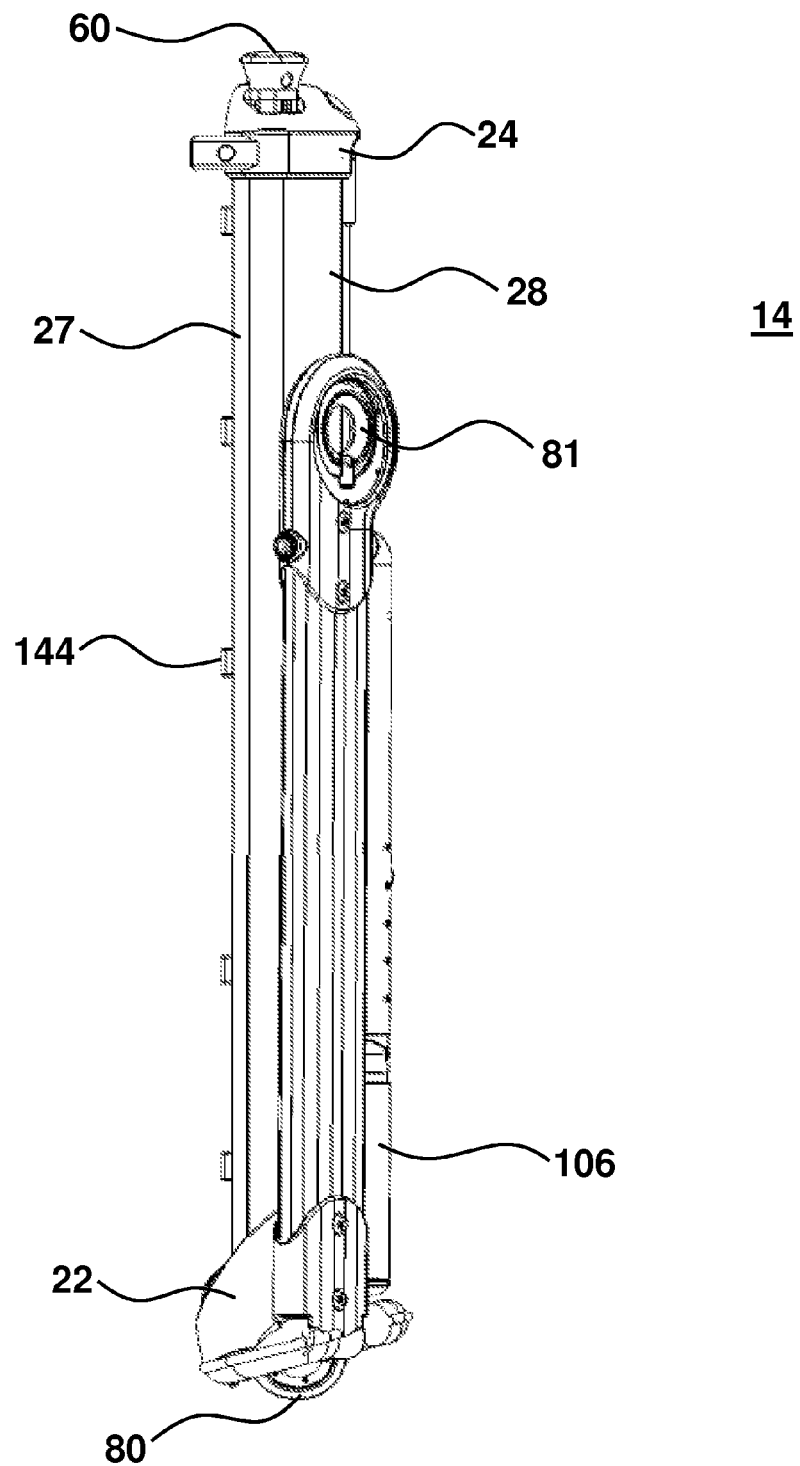
FIG. 15: Side view of the IMS of FIG. 13.
Figure 16:
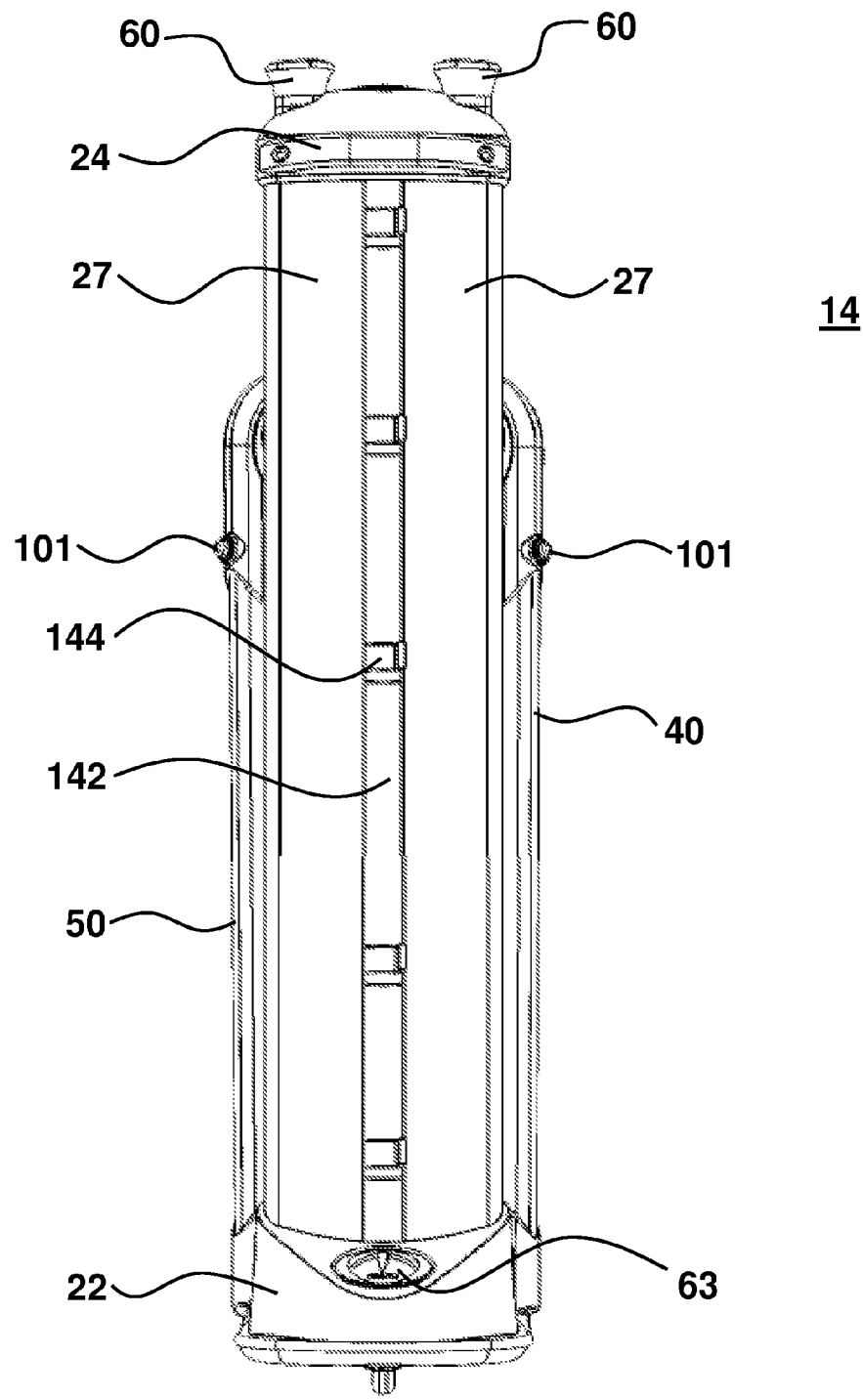
FIG. 16: Front view of the IMS of FIG. 13.

The IMS is particularly versatile in its modular system for supporting components. For example, one or more holding arms 60 are telescopingly connected to the trunk top end 24 (FIGS. 1-6). "Telescopingly connected" as known in the art (see, e.g., U.S. Pat. Nos. 5,458,305; 4,905,944) refers to the height of an object being adjustable by entering another object, thereby adjusting the height. The height of the holding arm is adjusted by engaging a holding arm locking mechanism, such as a holding arm lock button 61 (FIG. 1). In a stored position, holding arm 60 is substantially entirely contained within trunk 20 (FIG. 13). Holding arm 60 is particularly useful for supporting medical fluid bags such as IV fluid bags. In an embodiment, holding arm 60 is three-sided to provide multiple vertical and radial hook locations for each holding arm. The holding arm can further comprise means for selectably adjusting the location of holder 72. Means for selectably adjusting encompasses relatively simple configurations such as female receptacles axially spaced along each face of the holder arm 60 for receiving a holder or hook having a complementary male configuration. The receiving means can be by a threaded screw, snap bead or other system known in the art. In the exemplified embodiment, the means for selectably adjusting the location of a holder 72 is by interaction of holder 72 with a groove 62 that runs in each face along at least a portion of the longitudinal distance of arm 60. The groove can have a ladder to relief/recess features for receiving holder 72. In an aspect, each of the holders 72 is deployable, wherein in a stored position the holder 72 is folded into groove 62, to provide greater flexibility and options when hanging components and ease of storage when arm 60 is stored within trunk 20 (see FIG. 13). Any system that facilitates one hand hook deployment is preferable as such systems ease deployment/storage time and component hookup to the system.

Figure 2:
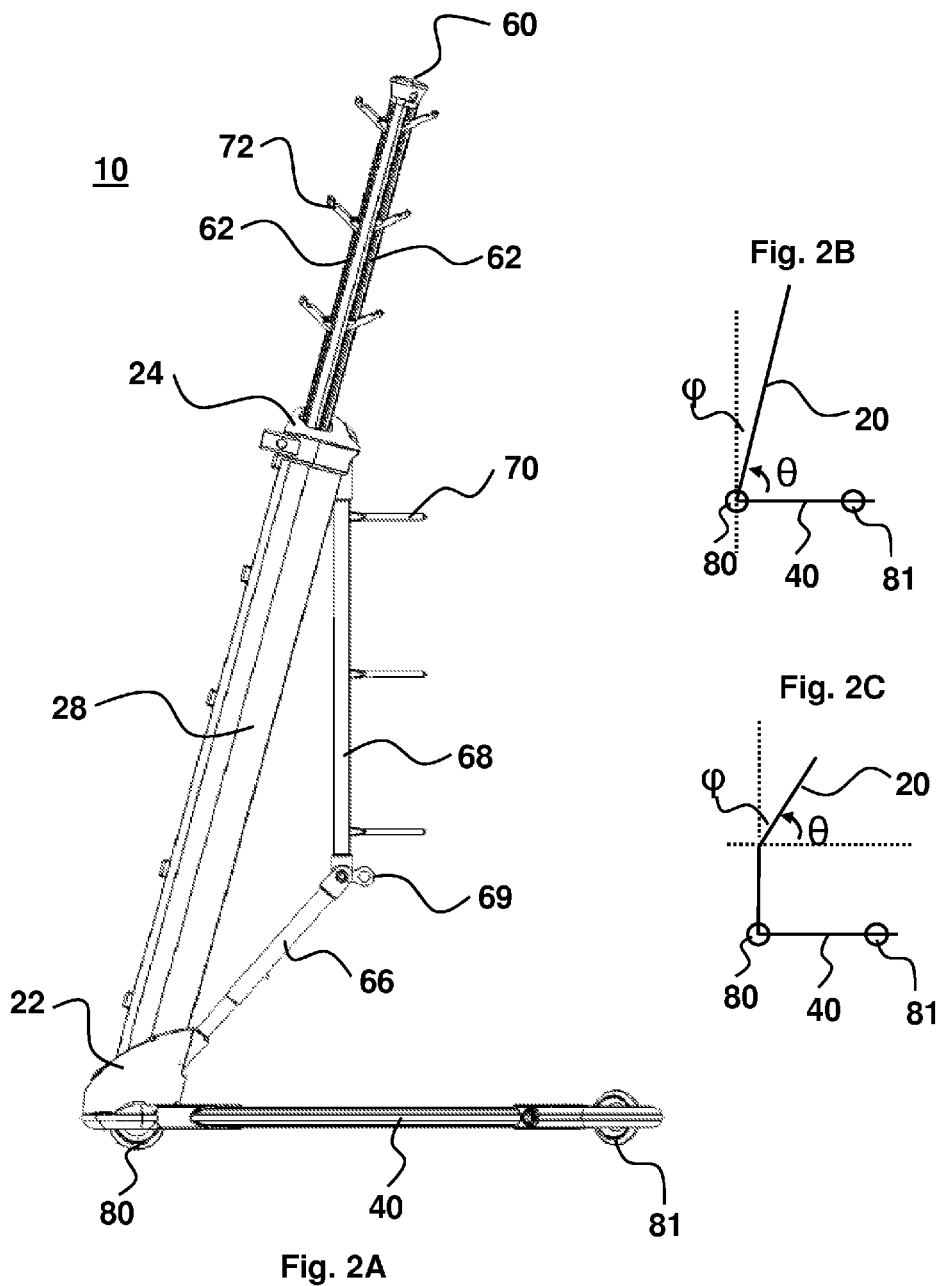
FIG. 2: A is a side view of the IMS of FIG. 1. B is a schematic diagram illustrating the trunk angle, θ, formed by the angle between the trunk and base arms and φ, trunk angle with respect to vertical. C. shows an embodiment where the axial trunk line is angled, with one trunk portion being vertical and another portion being tilted with respect to vertical.
Figure 5:
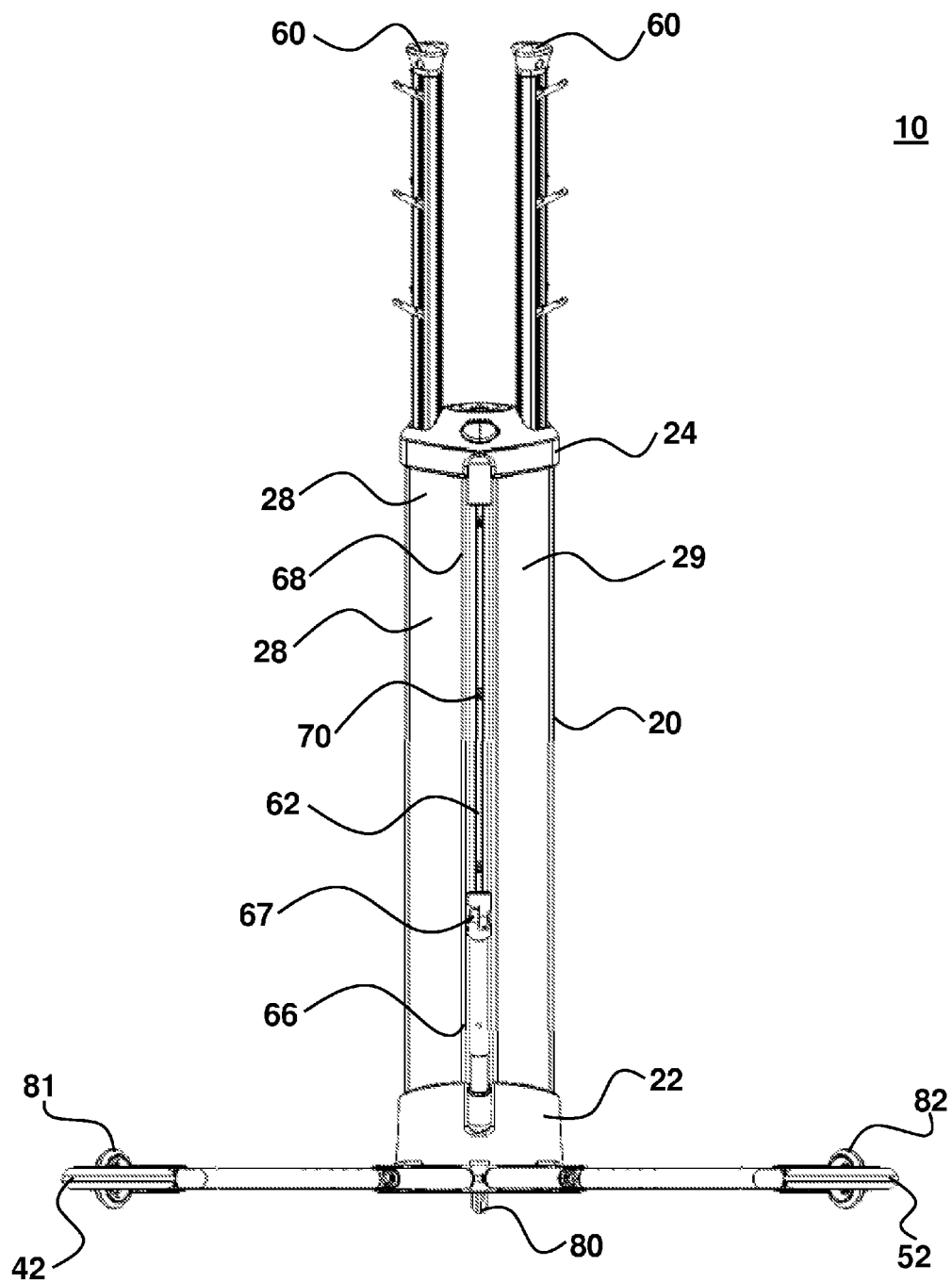
FIG. 5: Rear view of the IMS of FIG. 1.
Figure 6:
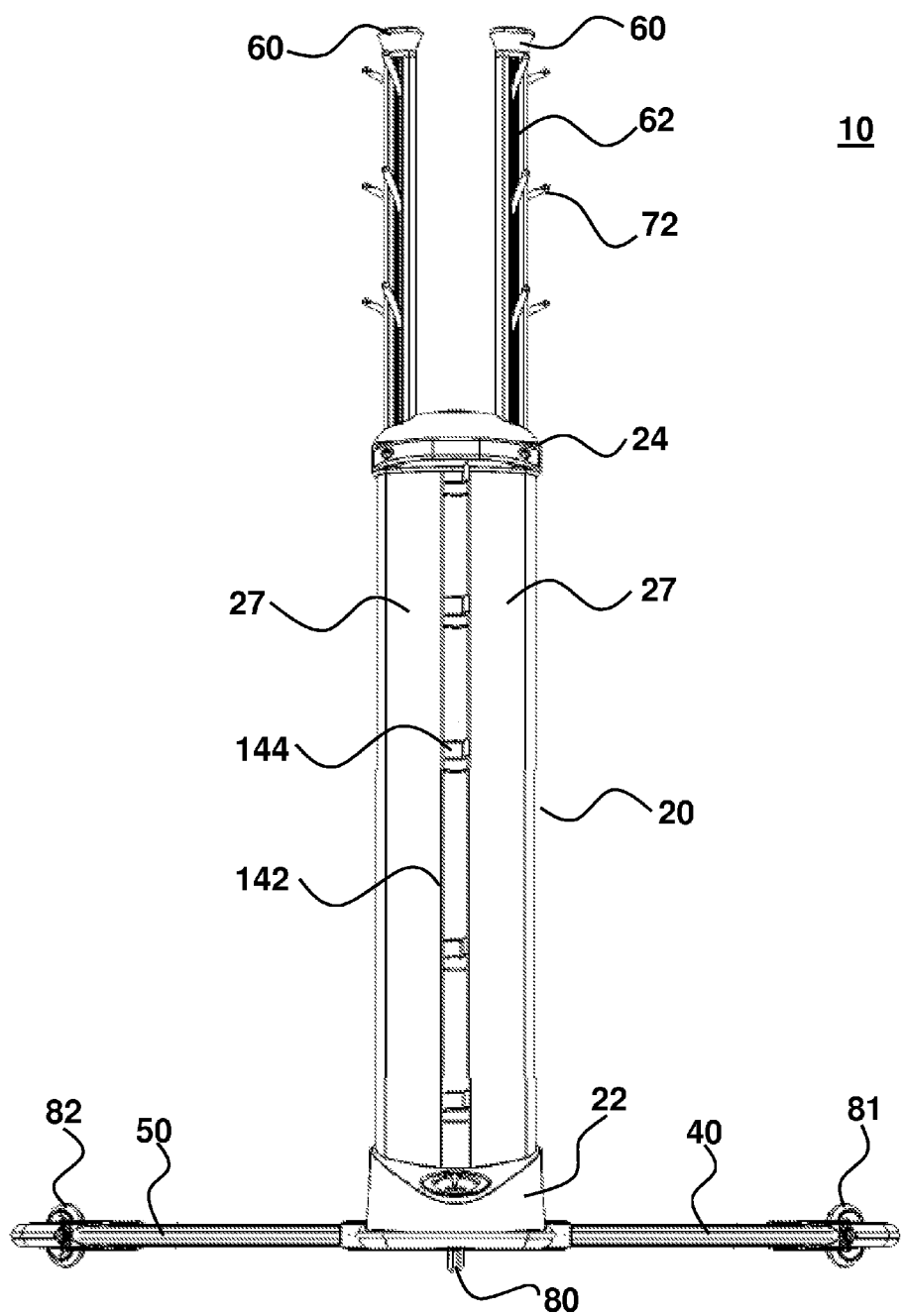
FIG. 6: Front view of the IMS of FIG. 1.

The exemplified embodiment illustrates an additional collapsible support or "foldable arm" 65 connected to the trunk 20 for holding medical devices and other relatively heavy objects (e.g., small platforms, power supplies, etc.). FIGS. 1 and 2 show collapsible support 65 connected to trunk top 24 and bottom 22. The collapsible support 65 comprises a bottom collapsible support section 66 having a telescoping connection that is lockingly positioned by pin 67 and a top collapsible support section 68. One end of sections 66 and 68 are deployably connected to trunk bottom 22 and top 24, respectively. The other end of sections 66 and 68 are connected to each other via folding joint 69. The folding joint 69 can further comprise means for deploying and storing the collapsible support, such as a handle, grip for one-hand deployment and storage of collapsible support 65. The deployable connection of ends of collapsible support 65 can comprise tension means such as a spring or hydraulics for facilitating stored configuration parallel to the trunk 20 and within trunk groove or recess 64 (when the collapsible support is not needed) and deployed configuration (when an attachment is to be mounted to a holder 70) where collapsible support 65 is pulled away from the trunk to ensure components connected to holder 70 are centrally located relative to base footprint 32. The holders 70 of collapsible support 65 can be selectably adjusted, positioned, deployed and removed, similar to the means described for holding arm 60. FIGS. 1 and 5 show holders 70 within collapsible support groove 62, wherein holders 72 may be deployed, folded within groove 62, mounted or removed, in a manner similar to the holding arm 60. In an embodiment, any of holders 70 or 72 can be specially shaped to have recess and relief features for receiving specific attachments having corresponding relief and recess features, where the attachment is in turn connected to a component.

The system 10 shown in FIGS. 1-6 is in the base-deployed configuration, with handles 100 and 120 that can be used in a walker-mode in their stored position, adjacent to base arms 40 and 50, respectively Example 2

IMS Walker/Mobility Assistance

Figure 7:
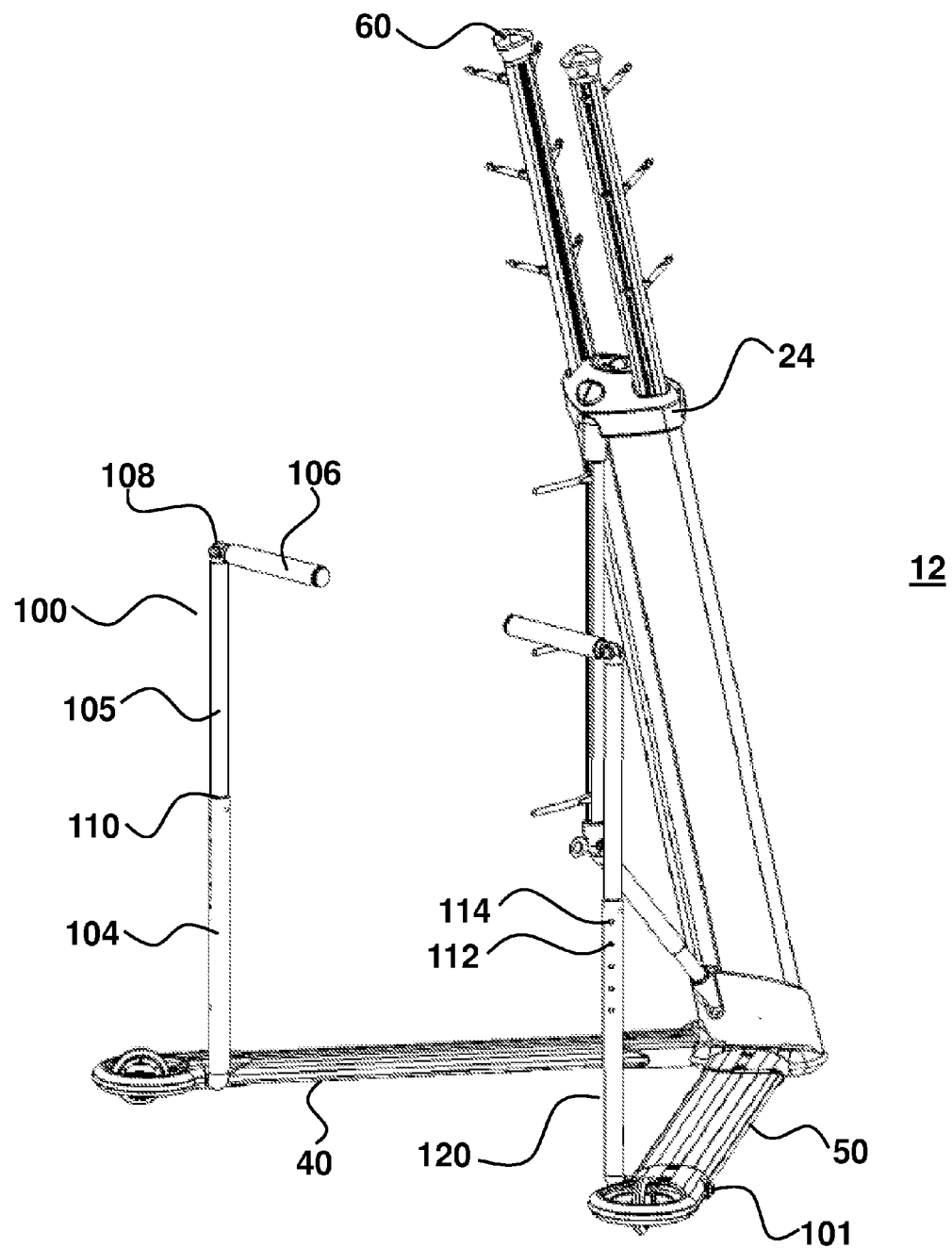
FIG. 7: Perspective view of the IMS of FIG. 1 with the handles deployed.
Figure 8:
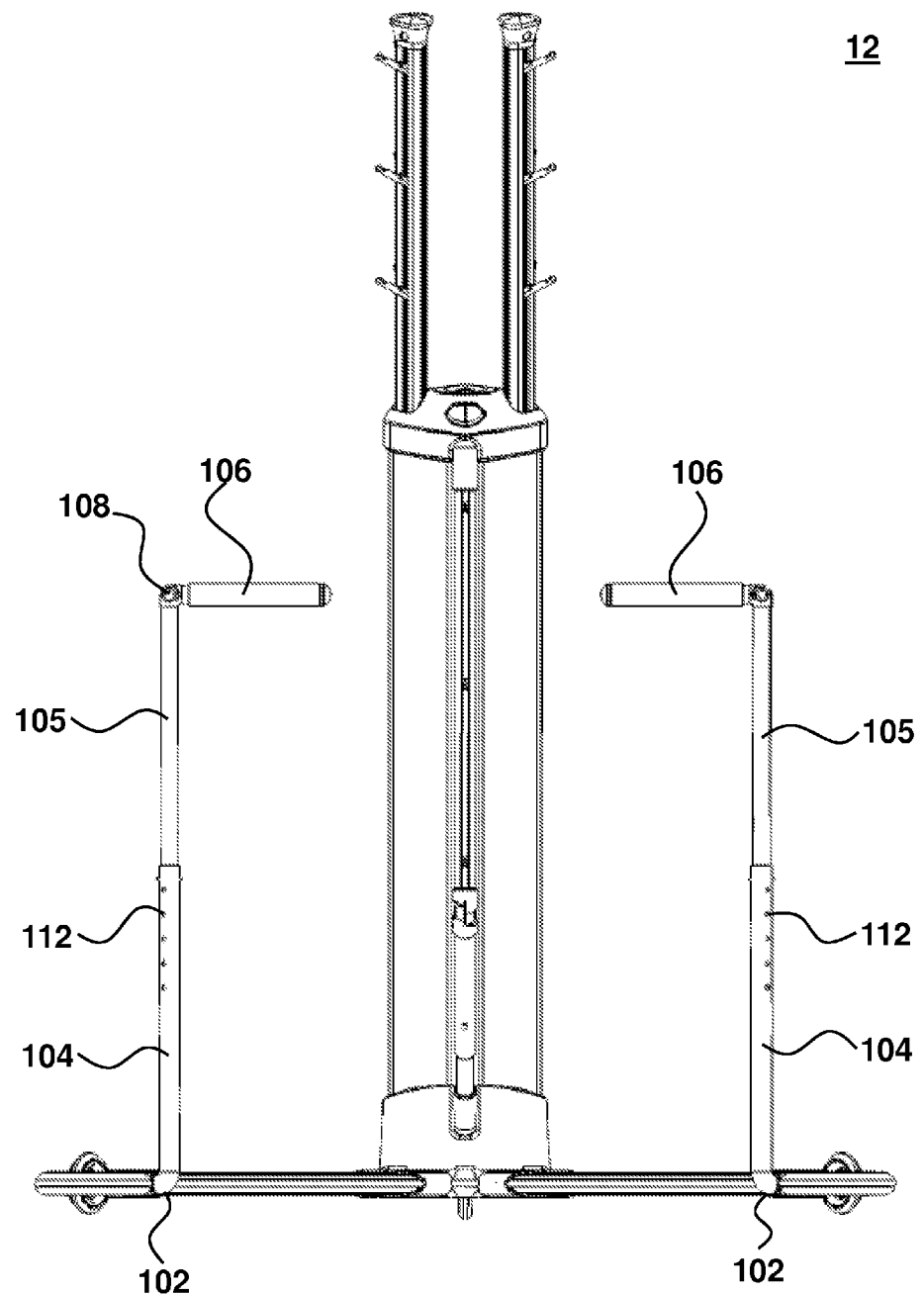
FIG. 8: Rear view of the IMS of FIG. 7.

A useful embodiment of the invention is a system that has mobility arms 100 and 120 deployed such that the system is in a base and walker deployed configuration 12 (FIGS. 7-12). FIGS. 1-6 illustrate base-only deployed configuration 10, and FIGS. 7-12 illustrate a system in a base and walker deployed configuration 12. Mobility arms 100 and 120 are connected to base arm 40 and 50, respectively (FIG. 7). The mobility arm 100 and 120 are each pivotally connected to base arm 40 and 50, respectively, so that the mobility arms are deployable. In the exemplified embodiment this pivot connection 102 is located at the inner surface of each base arm (FIG. 8). The connection can also be at other positions, such as the top surfaces 44 and 54 of the base arms 40 and 50 or outer facing surfaces of base arms. Mobility arms 100 and 120 are capable of locking into a deployed position (FIGS. 7-12) or a stored configuration (FIGS. 1-6) by a handle lock assembly 101 that lockably engages with the mobility arm. For example, depressing handle lock button 101 can disengage the lock that prevents rotation of mobility arm 100 or 120 with respect to base arm 40 or 50, thereby allowing mobility arm rotation. The lock can be under tension, so that when the mobility arm is in an appropriate position (e.g., vertical), the lock automatically engages thereby locking the mobility arm in its deployed position. Another locking mechanism is provided by lock assembly 101 and pivot connection 102, wherein when each of handles 100 and 120 deploy, each of caster wheels 81 and 82 lock in a fixed direction and cannot swivel, thereby improving the safety and stability of system 12 when ambulating by a patient.

Each handle optionally comprises a lower mobility arm section 104 and an upper mobility arm section 105. The arm sections 104 and 105 are optionally telescopingly connected to each other, thereby providing handles 100 and 120 that are length-adjustable and capable matching a user's height and hand position. For example, a single system can be used for a person walking or in a wheelchair (or by patients having different heights such as a child and an adult), by appropriately telescoping section 105 into section 104. A relatively simple telescopingly connection is illustrated in FIGS. 7-12, where a series of axially-positioned adjustment holes 112 on arm section 104 are capable of engaging a protuberance (such as a spring-loaded button) 114 located on upper arm section 105. Other telescopingly arm connections are known in the art, such as for walking poles and other stands with height-adjustable stands (e.g, U.S. Pat. No. 6,983,915; U.S. Pat. No. 5,458,305).

Figure 9:
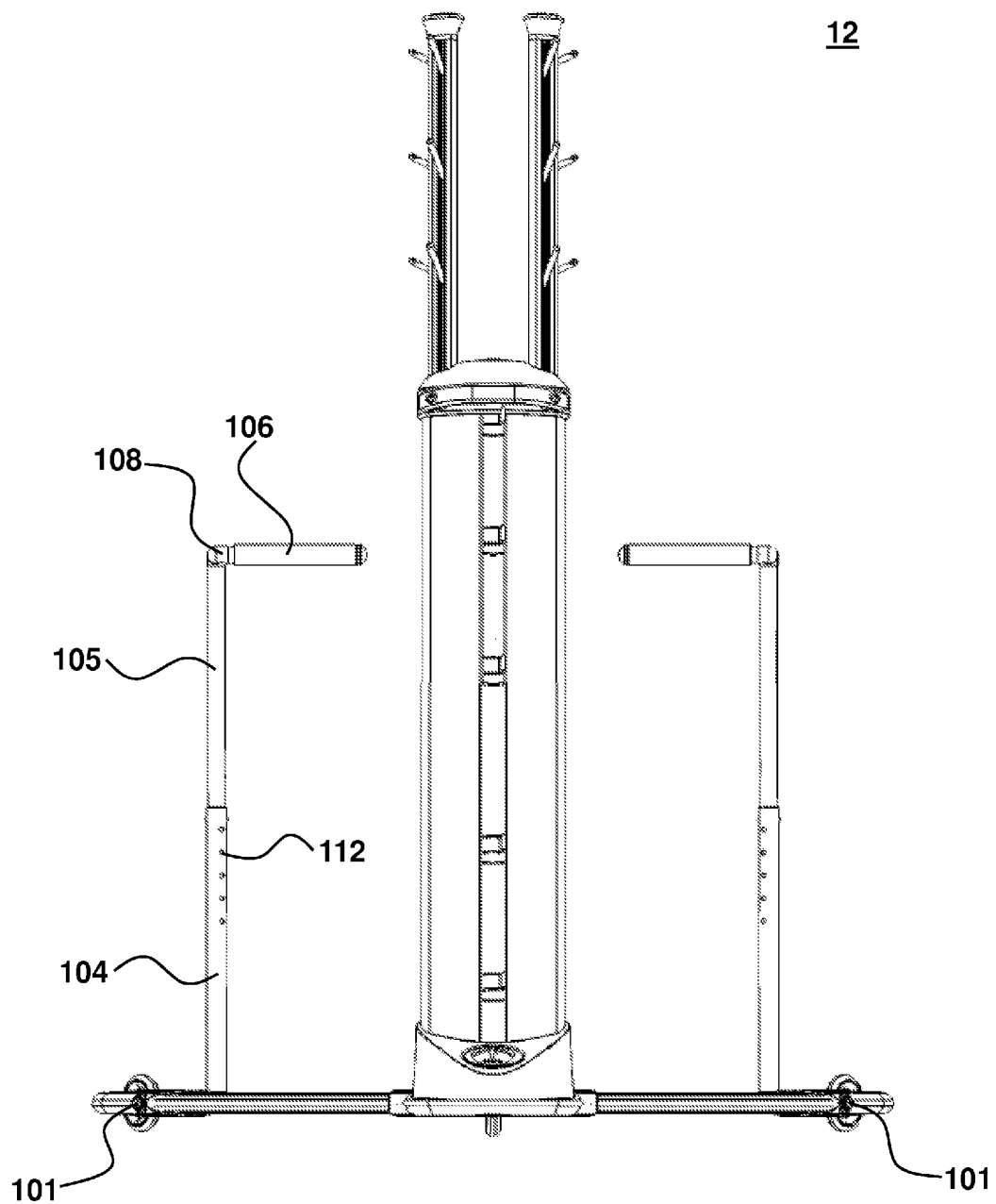
FIG. 9: Front view of the IMS of FIG. 7.

To facilitate compact storage and comfort for the user, each handle 100 and 120 can further comprise a handle grip 106 that is pivotally connected to the mobility arm 100 or 120, and more specifically to the upper mobility arm section 105. As shown in FIGS. 8 and 9, handle grip joint 108 connects handle grip 106 and upper section 105. The grip joint facilitates deployment of grip 106 from its stored position (e.g., parallel to mobility arm sections 104 and 105, see FIG. 4) to its deployed position (e.g., perpendicular to mobility arm sections 104 and 105, see FIG. 8B). The grip joint 108 can further comprise means for selectably positioning the amount of rotation of grip 106 relative to arm section 105, such as a male-female locking mechanism, tension screw, etc. The ability to selectably rotate grip 106 provides the ability to position grip 106 to ensure maximum comfort to a user who is using the system 12 in its walker configuration. In an embodiment, grip 106 is connected to a means for braking wheel 81 or 82. Means for braking includes a grip 106 that further comprises a throttle assembly for controlling or braking wheel rotation on the corresponding wheel (e.g., 81 or 82), or a braking lever connected to grip 106.

Figure 10:
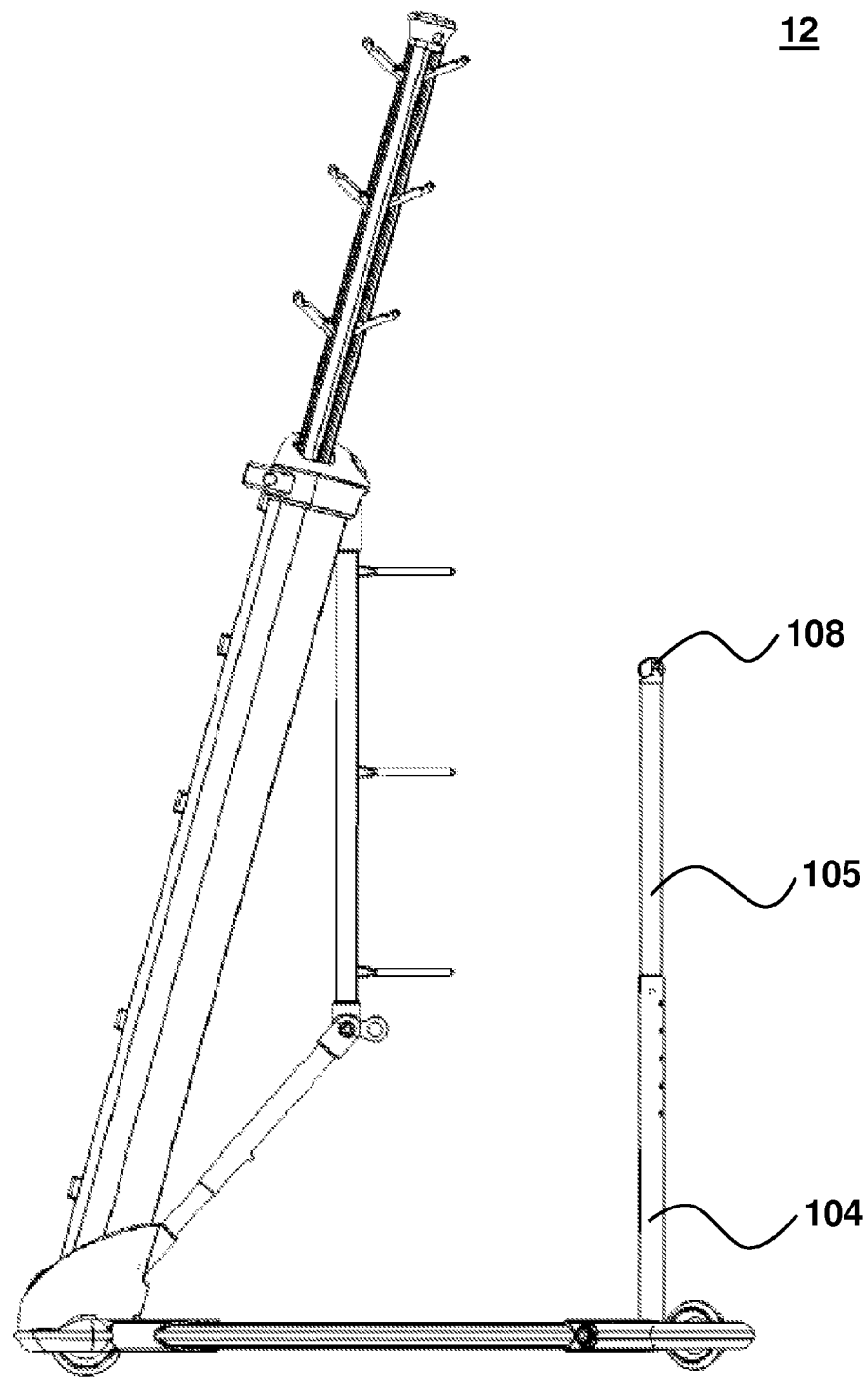
FIG. 10: Side view of the IMS of FIG. 7.
Figure 11:
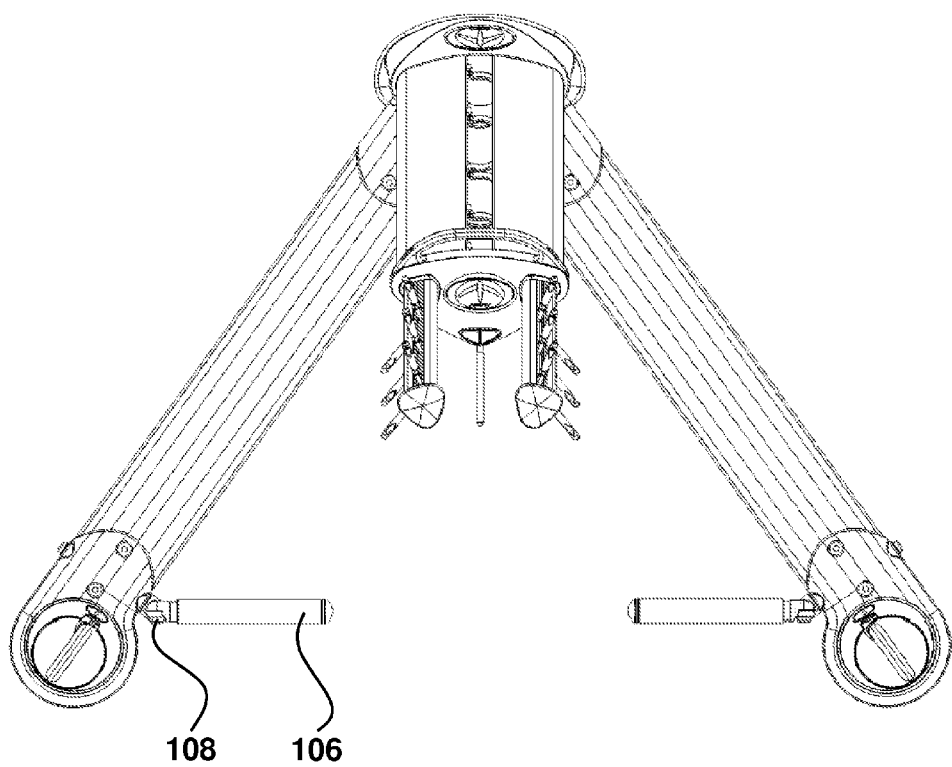
FIG. 11: Top view of the IMS of FIG. 7.
Figure 12:
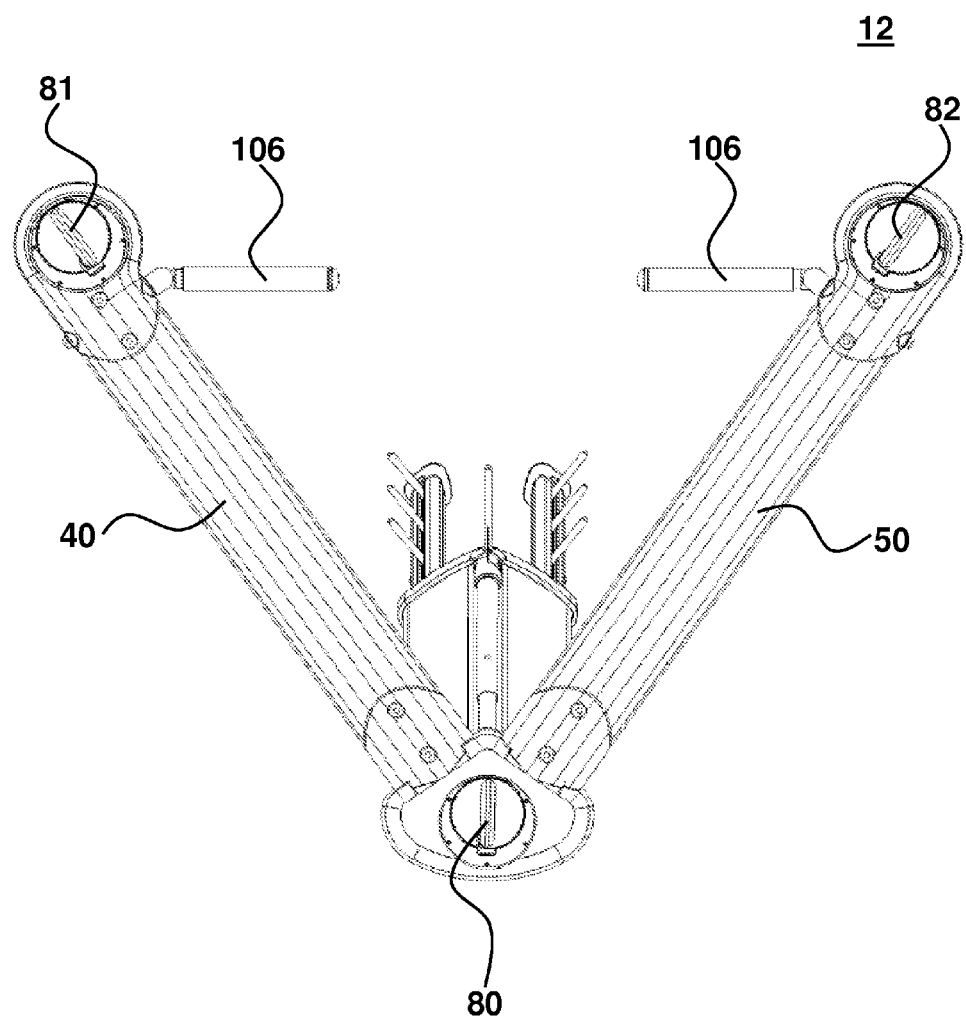
FIG. 12: Bottom view of the IMS of FIG. 7.

As shown in FIGS. 7, 10 and 11, the handle (and specifically the handle grip 106) is positioned such that none of the handles, wheels, IMS or components attached to the IMS interferes with the ability of the patient to walk and maneuver the system. The system 10 and 12 provides great flexibility in positioning components in a wide variety of locations so as to provide maximum stability during system movement, patient support to ensure safety during movement, as well as ensuring that the attached components do not interfere with patient movement or obstruct the patient's line of site. The system is also capable of receiving an ambulating force from a person besides the ambulating patient (e.g., a caregiver). The means can be a handle on trunk 20, as well as a tether or rope system.

Example 3

IMS Storage

FIGS. 13-18 illustrate the system in its stored configuration 14. In particular, each of the individually deployable components (wheels 81 and 82, base arms 40 and 50, handle grip 106, handle (100, 120, 104, 105), holding arm 60, collapsible support 65, holders 70 and 72) are stored to provide maximum compactness. Wheel 80, is shown deployed and can be used to assist in moving system 14 by rolling it over a surface to or from a storage location or to an area where it is to be deployed.

The system is able to be compactly stored, while retaining the ability to be quickly and easily deployed by a single person. For example, depressing base lock button 31 allows base arms 40 and 50 to unlock from their stored position (parallel to trunk 20) and into their deployed base configuration. Holding arm lock 61 is depressed to deploy holding arms 60 in a position ready to receive one or more medical components. Folding arm 65 is located within a trunk storage groove 64 in the stored position. The folding arm is deployed by engaging means for deploying the folding arm, as discussed. The mobility arm is rotably engaged and deployed by disengaging the lock mechanism by, for example, depressing handle lock button 101. The handle grip 106 is deployed by rotating the grip 106 relative to mobility arm 104. Each of wheels 80-81 are deployed when a walker configuration 12 is desired. A locking assembly mechanism, such as activatable button 63 provides one convenient means for deploying and unlocking base arms 40 and 50.

Figure 17:
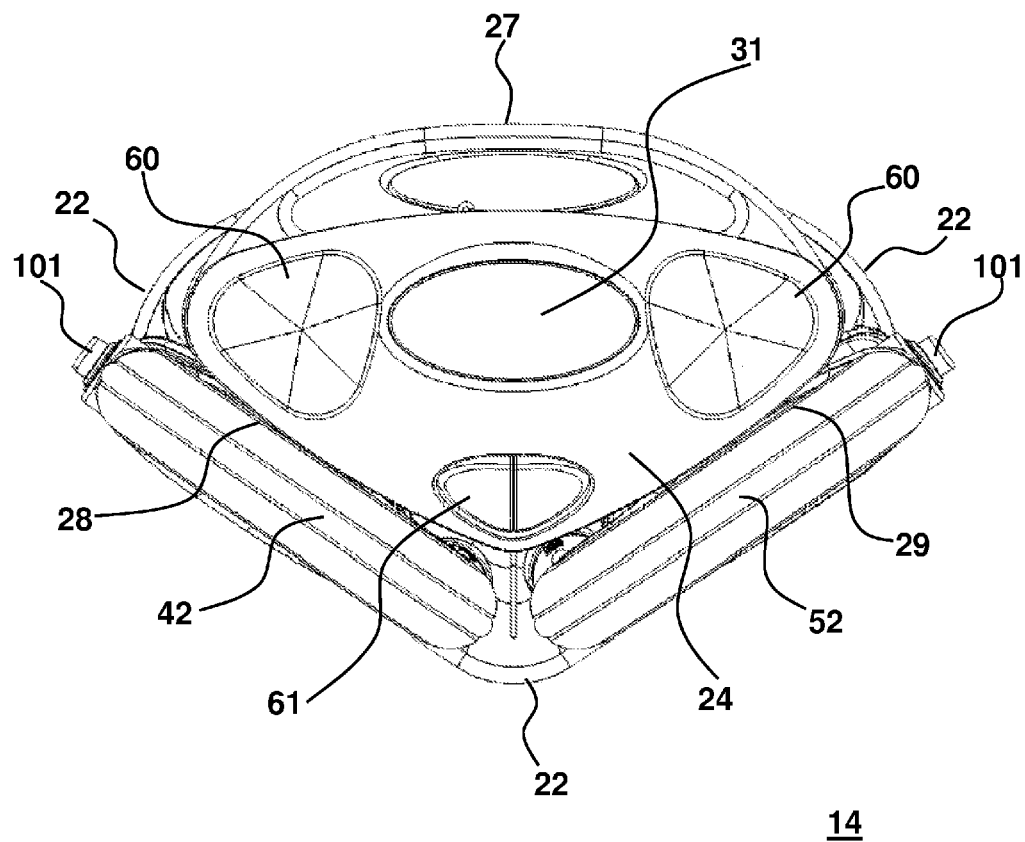
FIG. 17: Top view of the IMS of FIG. 13.

As shown in FIG. 17, the trunk is generally three-sided, having major surfaces 27 (front) and 28 and 29 (sides) each connected by a curved corner. Each of the sides is configured to compactly receive arms 40 and 50. Sides 28 and 29 are optionally contoured to receive a corresponding contoured top surface (44 or 54) of base arms 40 and 50. The invention encompasses base arms 30 and 40 that are substantially parallel to the long axis of trunk 20 when stored. Maximum compactness is achieved by having the base arm contact or have a minimum separation distance from the trunk along the length of the base arms 40 and 50.

The invention includes means for hanging the IMS in its stored configuration. Hangers fastened to the wall are configured to receive and hold the stored system 14. For example, the holder can firmly connect to a trunk portion, such as a portion that is between the trunk top 24 and end of the base arm wheel system. This connection is by any means known in the art for holding, such as hook and receiver (with the hook attached to the wall and/or the trunk), orifice, grooves, etc. The stored system can also be hung from a ceiling by top end 24 or bottom end 22. The system and wall bracket is optimally configured by angling the wall-stored system such that one person can easily and readily remove the system from the wall bracket by, for example, deploying base arms 40 and 50. In addition, the wall-mounted IMS can still be used to connect a patient (such as a patient in bed) to medical components, while remaining ready to be ambulated as-needed.

For systems that are not base-deployable (or for base-deployable systems, where the bare is in a deployed configuration), multiple systems may be stacked/nested relative to each other, thereby providing compact storage.

Example 4

Wheel System

An important aspect of the invention that is a walker is the wheel and associated wheel system that connects the wheels to the IMS. FIGS. 18-24 provide close-up views of a wheel in a deployed 88 (FIGS. 19-21) and storage 89 (FIGS. 22-24) configuration. The wheel system can be used in other systems where the ability to position a structure in different locations is important, such as a variety of stands (e.g., bicycle stands) furniture (tables, nightstands).

Figure 19:
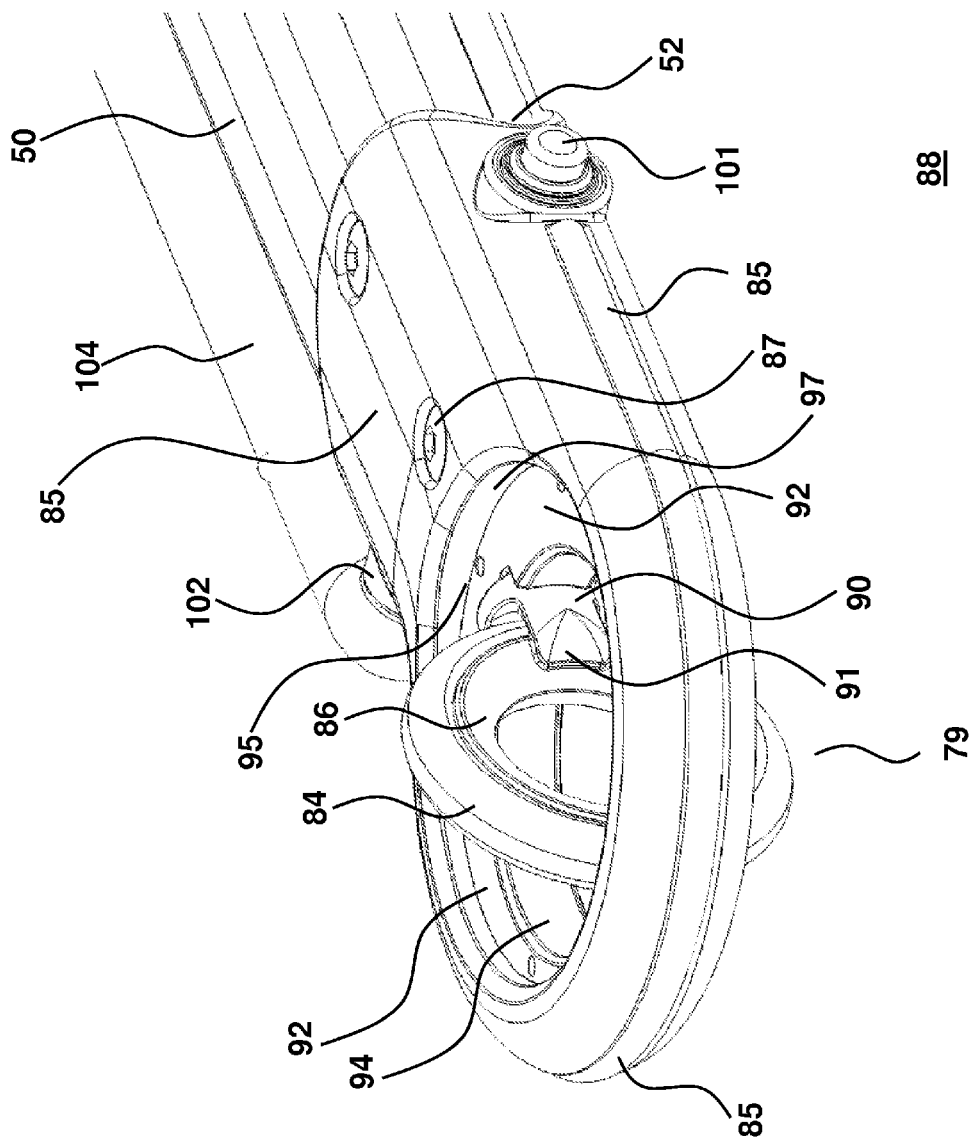
FIG. 19: Perspective close-up view of a wheel system useful in the IMS of the present invention. This wheel corresponds to a wheel connected to one of the base arms and shows the wheel deployed to facilitate IMS ambulation.
Figure 21:
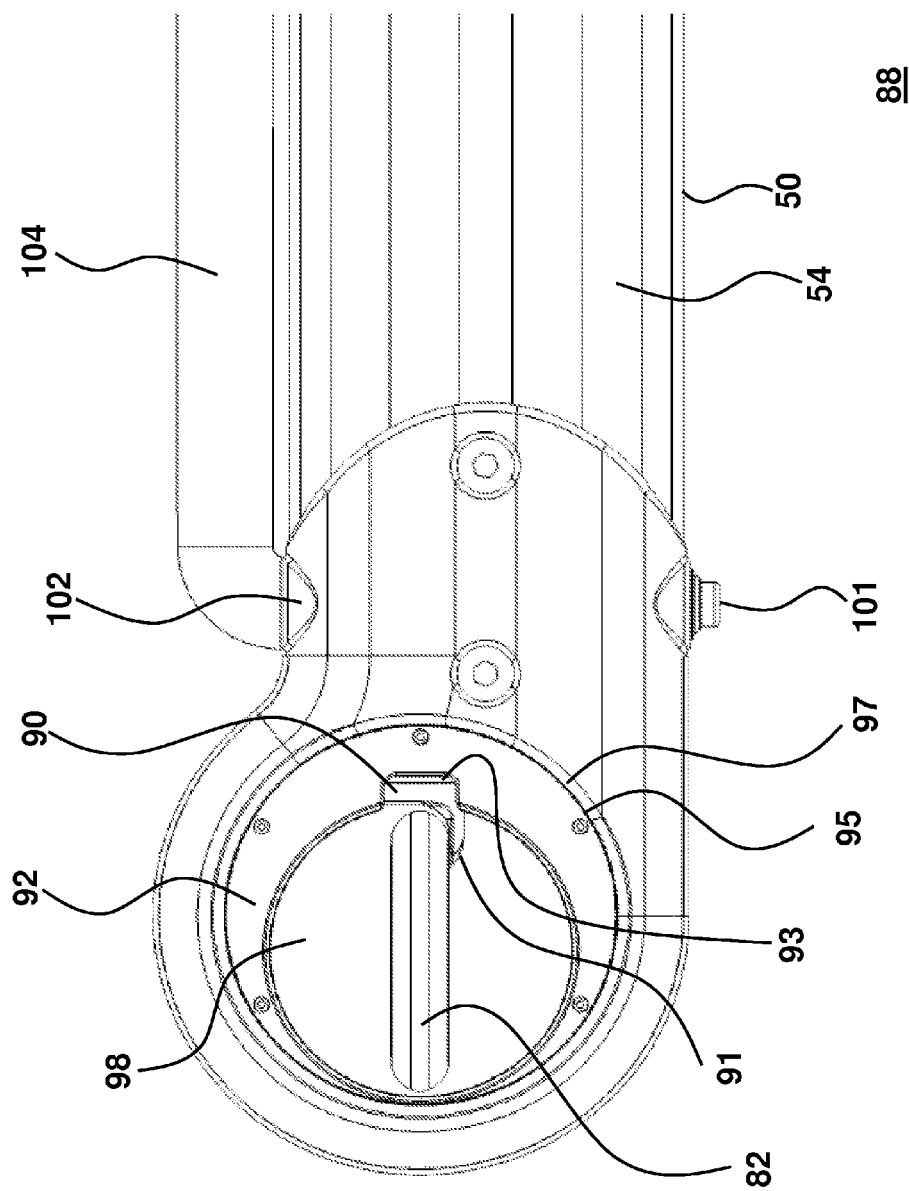
FIG. 21: Top view of the deployed wheel system of FIG. 19.

Referring to FIG. 19, a wheel system 79 comprises an outer wheel portion 84 that is rotably connected to an inner wheel portion 86. This rotable connection is by any means known in the art such as ball bearings, so that the outer portion 84 can rotate relative to the inner portion 86. The inner wheel is connected to one end 91 of a wheel holder 90, and the other end 93 of wheel holder 90 is connected to ring mount 92, and optionally pivotally connected to ring mount 92 (FIG. 21). The pivotal connection between wheel holder 90 and ring mount 92 provides the wheel deployable capability, wherein a rotating (orthogonal to the direction of wheel rolling) force can be applied to wheel outer portion 82, thereby pivoting the wheel and wheel holder 90 from the deployed position shown in FIG. 19 to the stored position shown in FIG. 22.

Ring mount 92 is generally ring-shaped, having an inner-facing surface 94 and outer facing surface 95. The inner surface 94 defines the edges of a generally cylindrical passage or orifice 98 having a diameter greater than the diameter of the outermost surface of outer wheel portion 82, so that the wheel is positioned within the orifice 98 defined by inner surface 94. In this example, wheel holder 90 is rotably attached to the inner surface 94 of ring mount 92. Outer ring mount surface 95 is connected to a wheel cover 85, and more specifically to cover wheel receiving surface 97. In the embodiment where the wheel is capable of swiveling to point in the direction of an applied force, the connection between outer ring mount surface 95 and wheel receiving surface 97 is a rotable connection. The rotable connection is facilitated by any means known in the art, including by ball bearings that permits rotation of ring mount 92 relative to wheel receiving surface 97. The orientation of the wheel (e.g., the direction the wheel rolls) can be fixed in position by a lock that lockably engages ring mount 92. The ease of ring mount 92 to rotate relative to surface 97 can also be controlled by any braking means known in the art. For example, a rubber brake pad that brakingly engages ring mount outer surface 95 provides a means for controlling the amount of force required to swivel the wheel 79. Varying the frictional force that must be overcome in order to swivel a wheel is useful in an IMS walker that provides greater support to the patient at the expense of requiring greater force to maneuver the walker.

A wheel system that does not need to swivel can have fewer parts and connections. For example, wheel holder 90 can be mounted directly to wheel receiving surface 97 without the need for any cylindrical ring mount 92. Alternatively, the wheel holder 90 can connect directly to the end of the base arm.

Figure 20:
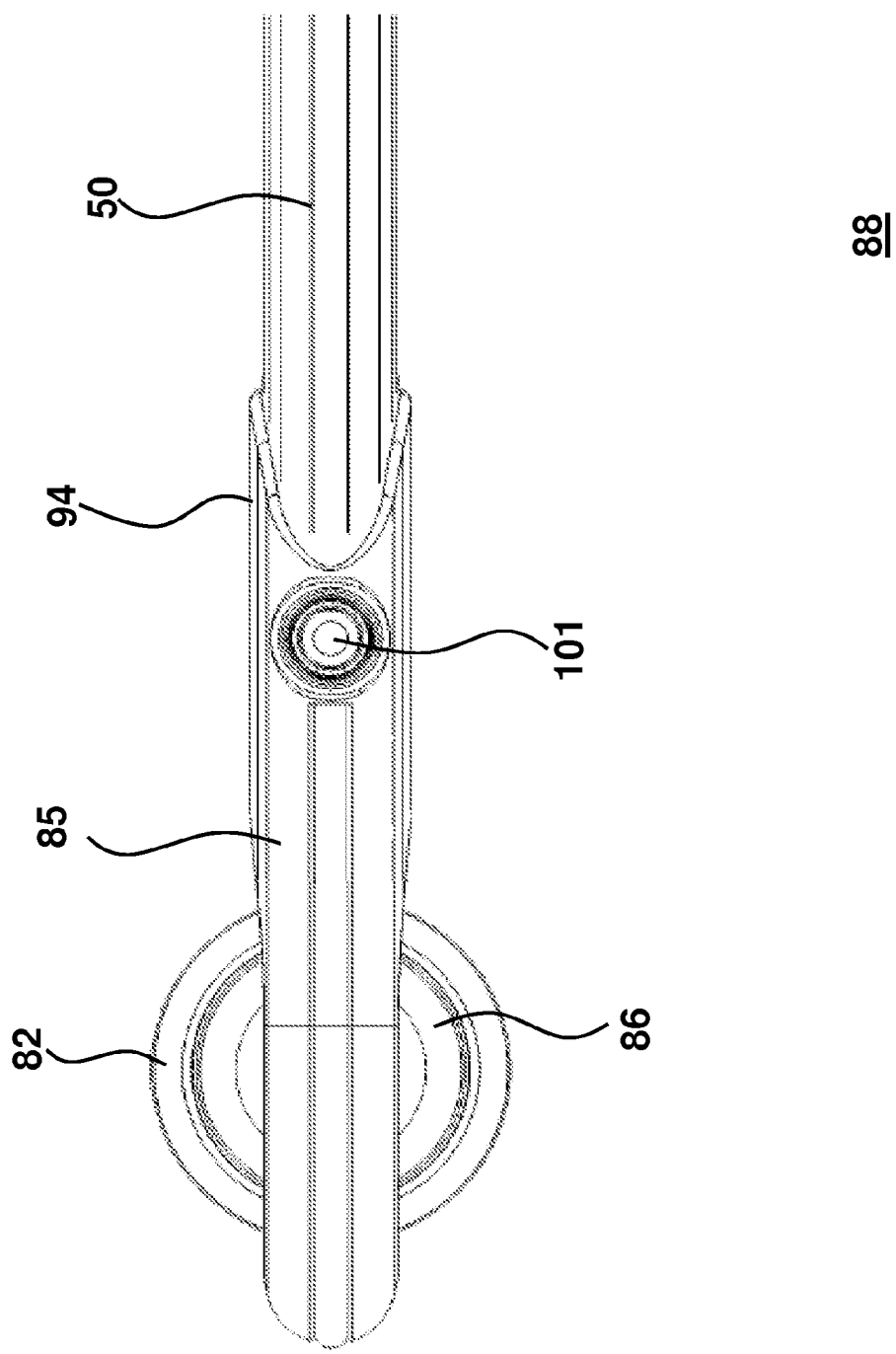
FIG. 20: Side view of the deployed wheel system of FIG. 19 useful in the IMS of the present invention.

FIG. 19 shows that wheel cover 85 is capable of connecting to a base arm, such as base arm 50, by sliding over the base arm and fastening the cover 85 to the base arm 50 by fastening means 87. Cover 85 can be shaped to have an open end capable of receiving base arm 40 or 50 and an opposite end 52 that surrounds the wheel, ensuring the wheel is able to roll without worrying about incidental contact from a foot or a person's clothing, for example. FIGS. 20 and 21 provide different views of a deployed wheel 88 that is connected to a base arm. Any of the wheel systems described herein can further comprise means for braking to prevent rolling movement of the IMS, including a rubber brake pad that brakingly engages rotating wheel portion 84.

Figure 18:
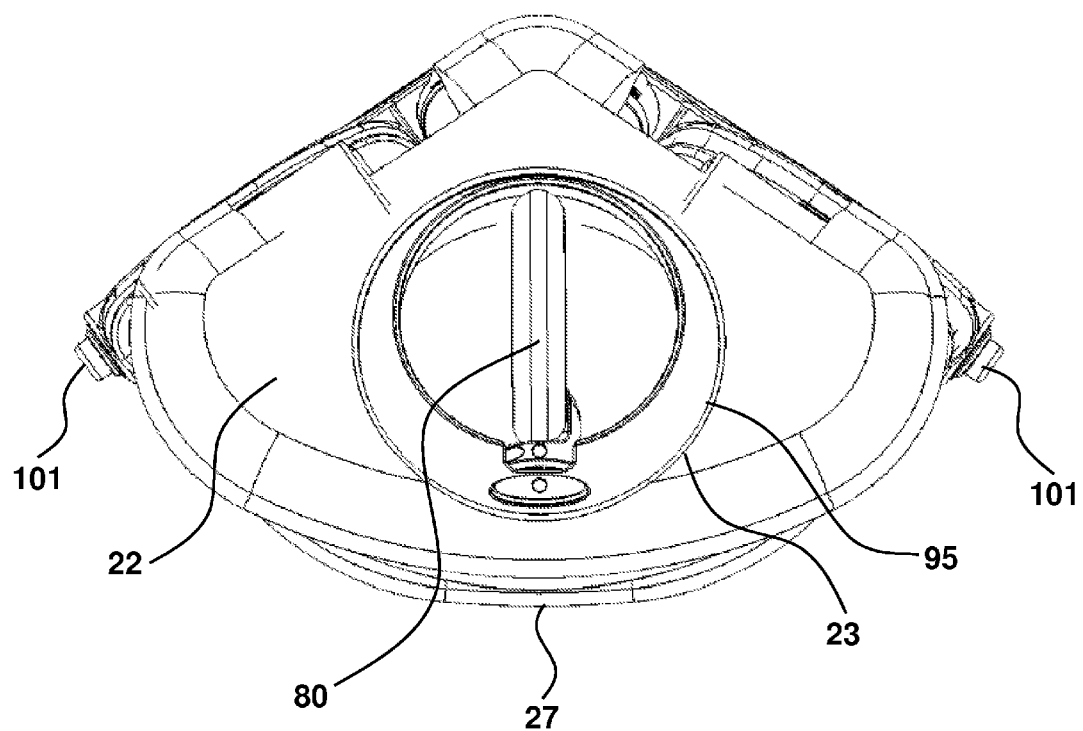
FIG. 18: Bottom view of the IMS of FIG. 13.

FIG. 18 (and also FIG. 4) illustrates the first wheel 80 that is connected to the trunk bottom 22. In this embodiment, the outer ring mount surface 95 contacts the orifice 23 disposed in the bottom-facing surface of trunk bottom 22. In the embodiment where the first wheel can swivel, the connection between surfaces 23 and 95 is a rotable connection.

Figure 22:
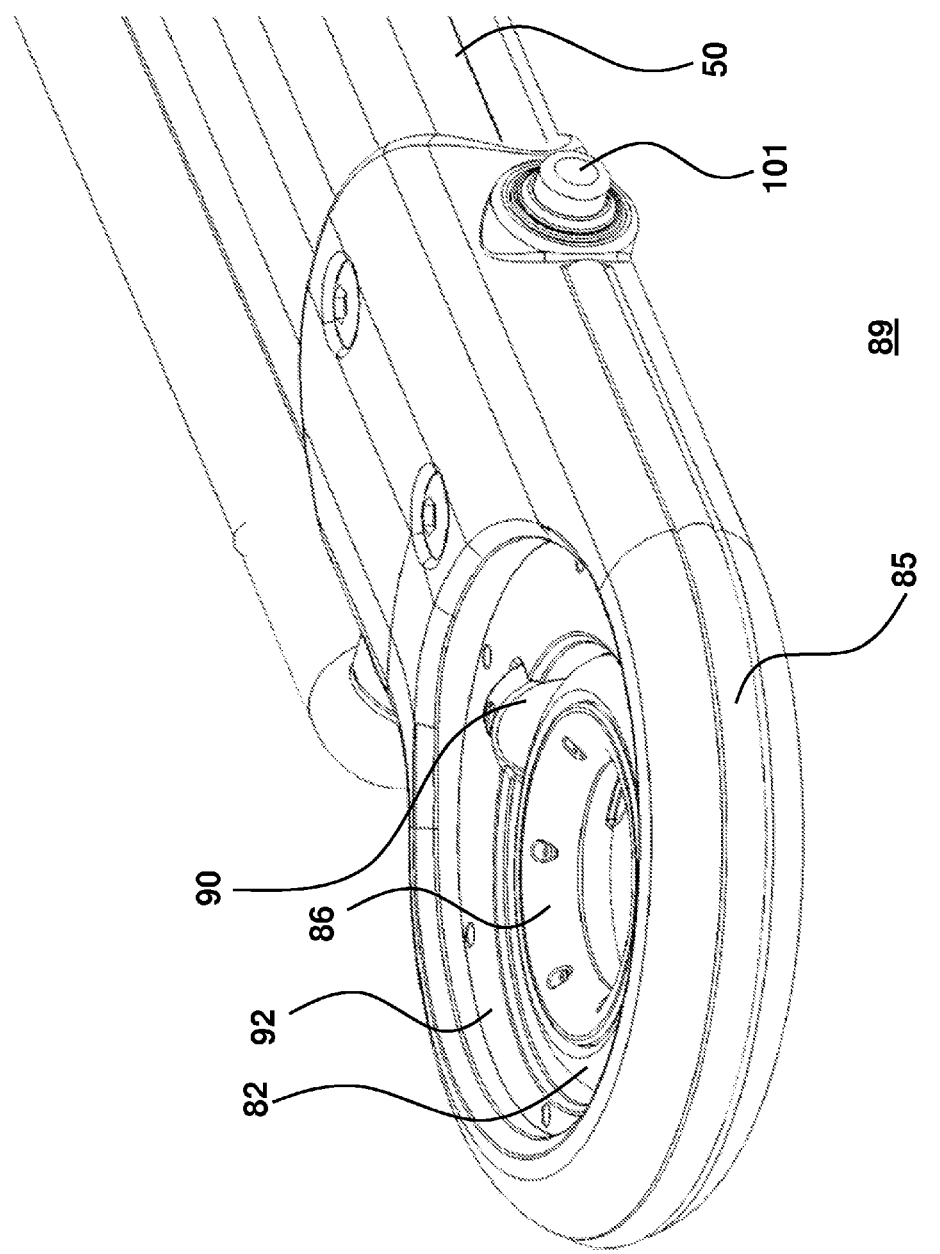
FIG. 22: Perspective view of the wheel system illustrated in FIG. 19 with the wheel in its stored position. This configuration is useful for when the IMS is to be folded into its stored configuration and also for when the IMS is to be deployed but not ambulated.
Figure 23:
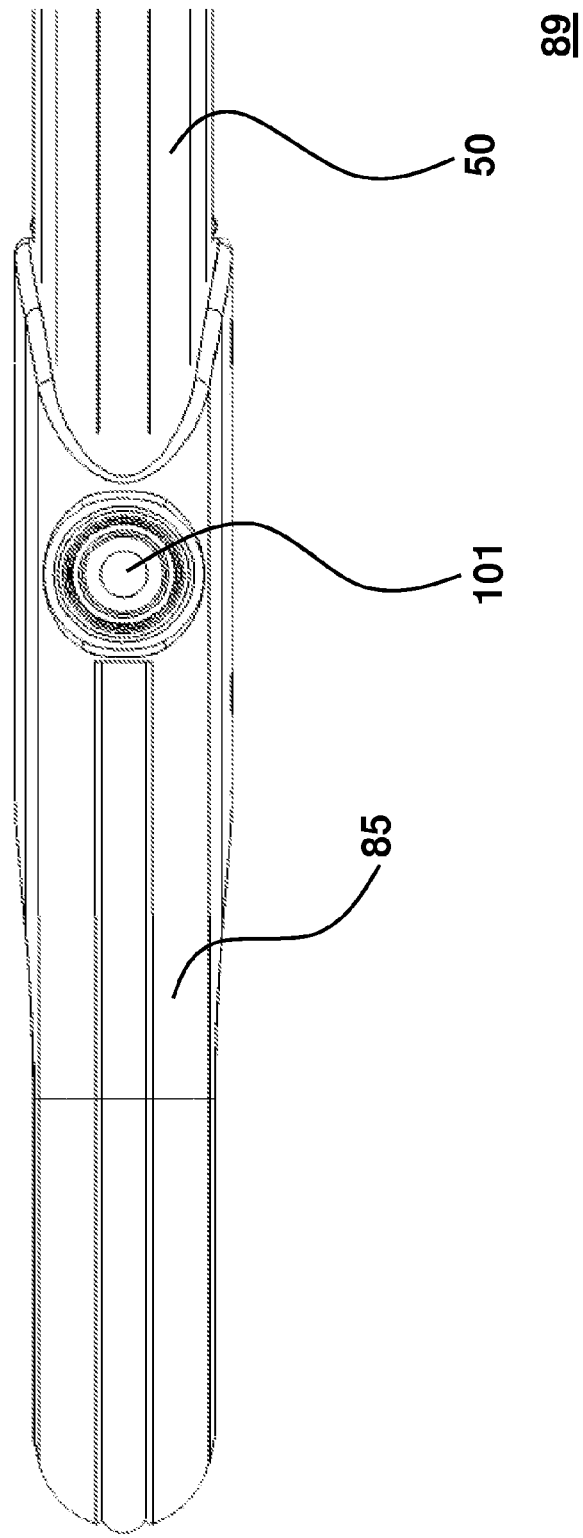
FIG. 23: Side view of a wheel system of FIG. 22.
Figure 24:
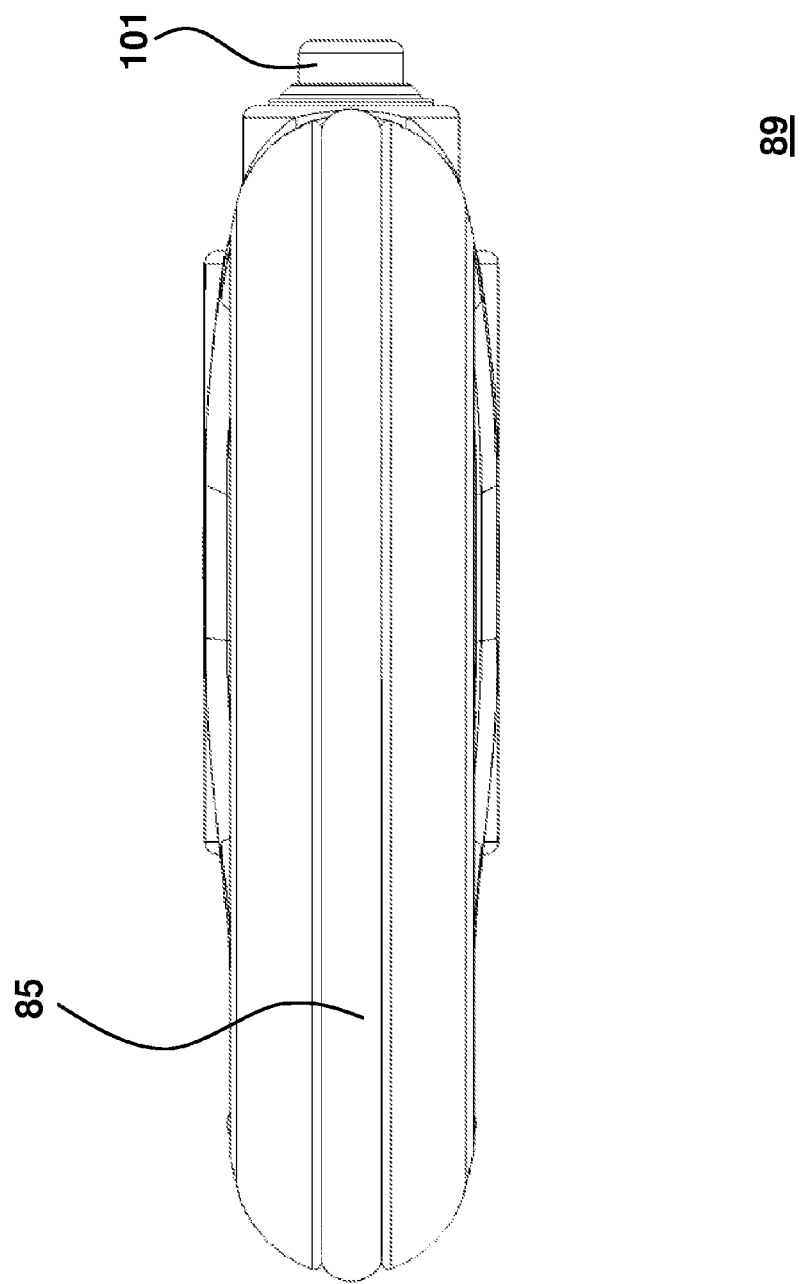
FIG. 24: End view of a wheel system of FIG. 22.

FIGS. 22-24 show the wheel in its stored configuration 89. In particular, FIGS. 23-24 illustrate that the wheel is contained completely within wheel cover 85 thereby providing an increase in surface area contact between the IMS and supporting surface.

Figure 25:
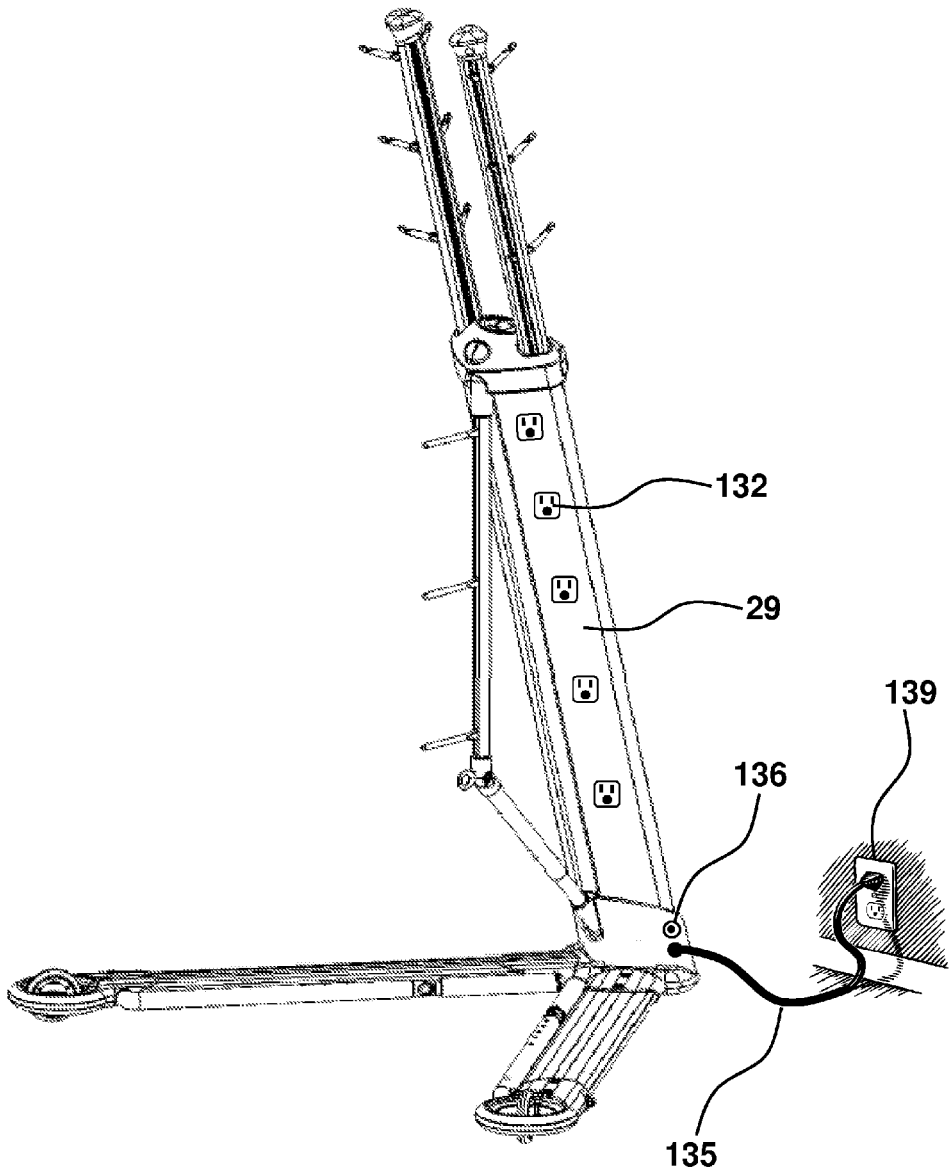
FIG. 25: Illustration of an IMS of the present invention having an integrated electrical system for powering one or more electrical devices.

Any of the systems of the present invention can have additional features such as built-in components (e.g., calculators), illumination systems and/or electrical systems. One example of an electrical system is provided in FIG. 25, where a plurality of electrical outlets 132 is located on a trunk side surface 29. Power is provided by any means known in the art, such as by an AC cord 135 connected to a conventional AC outlet 138, wherein the AC cord 135 is electrically connected to each of the electrical outlets 132. The aspect depicted in FIG. 25 is not practical when the system is moving. Accordingly, another aspect of the invention is a power supply that is either attached to the system externally (for example, at one of the holders) or contained within the system (for example, disposed within trunk 20) and electrically connected to outlets 132. The power supply can be a primary or secondary (e.g., rechargeable) battery. The electrical connection to a DC source can be by a DC power cord connector 136, as known in the art. Any one or both of the AC and DC power connecting cords can be retractable, for storing the length of electrical cord within the trunk body 20 when the cord is not in use. The electrical system can be a single outlet or a multiple outlet power strip connected to the front and/or back of the trunk 20.

Example 5

Mobility Assistance Devices

Figure 26:
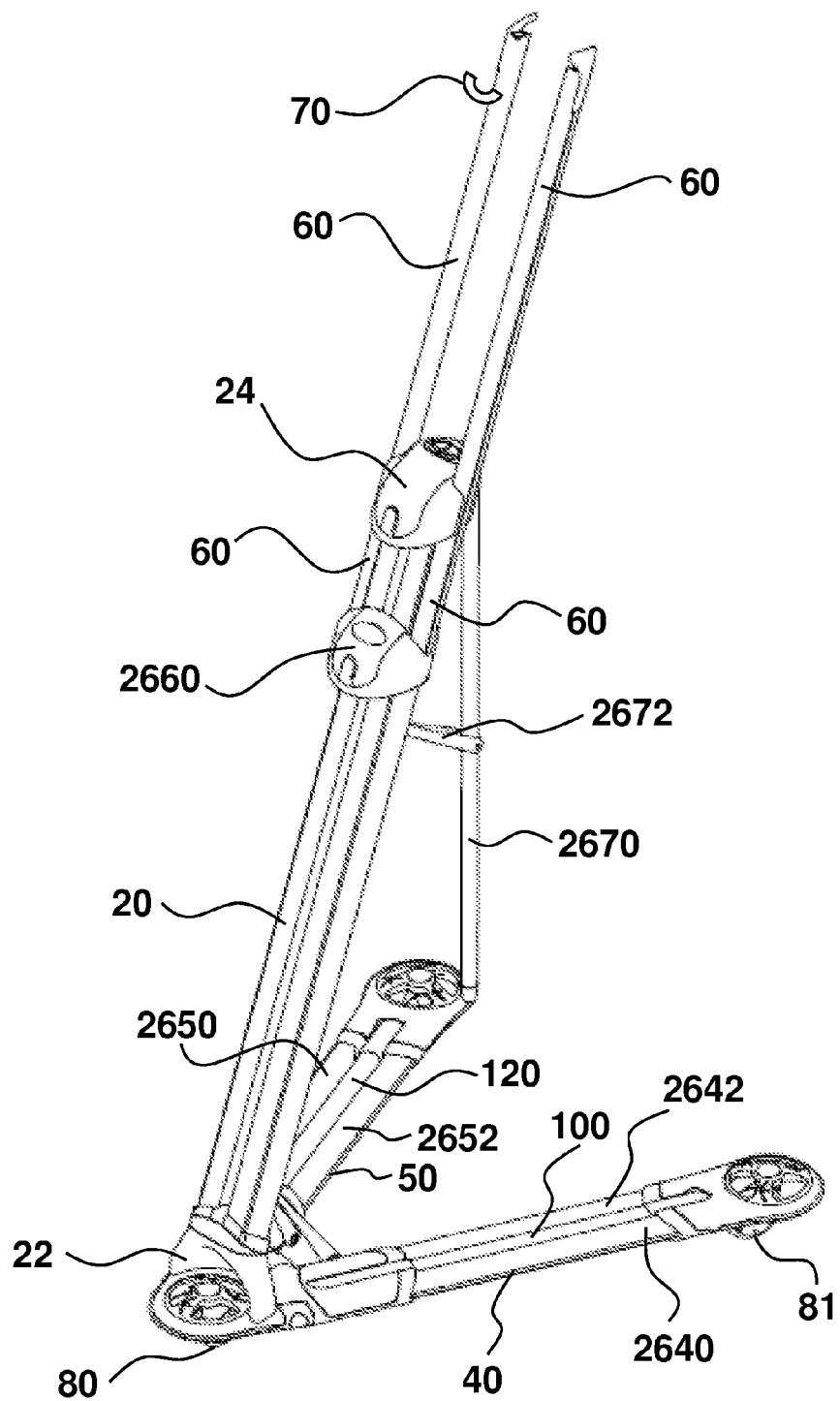
FIG. 26 is a perspective view of a mobility assist IMS with the mobility assist arms in a stored configuration.
Figure 29:
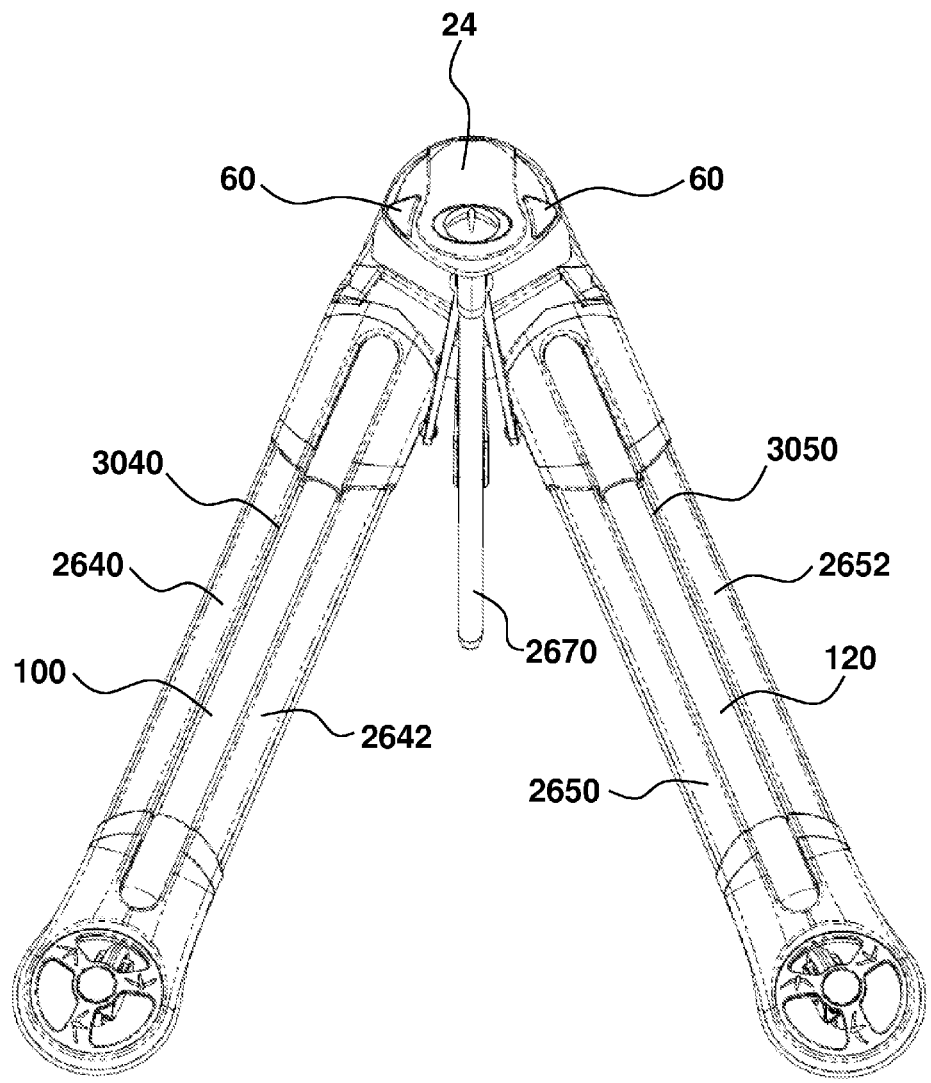
FIG. 29 Top view of the system of FIG. 26.

An example of a relatively basic IMS is provided in FIGS. 26-39. In this embodiment, mobility arms 100 and 120 are stored, respectively, in a recess within each of base arms 40 and 50 (see FIGS. 26, 29, 30 and 34A). Referring to FIGS. 26 and 29, the edges of the recess are defined by split base arms 40 and 50. In particular, the exterior-facing base arm section 2640 2650 and interior facing base arm section 2642 2652 of split base arms 40 50 (respectively). Providing base arms 40 and 50 having at least a portion that is split corresponding to 2640 and 2642 for base arm 40, and 2650 and 2652 for base arm 50 provides in a mobility arm stored configuration (see FIGS. 26-29), mobility arms 100 and 120 that are substantially flushingly engaged within the confines of base arms 40 and 50, respectively. This conveniently stores the mobility arms when patient mobility assistance is not required. Alternatively, mobility arms in a stored position may be positioned in or on other locations such as adjacent to a surface on base arms 40 and 50 (e.g., see FIG. 1 for positioning next to inward-facing surfaces of 40 and 50).

Figure 30:
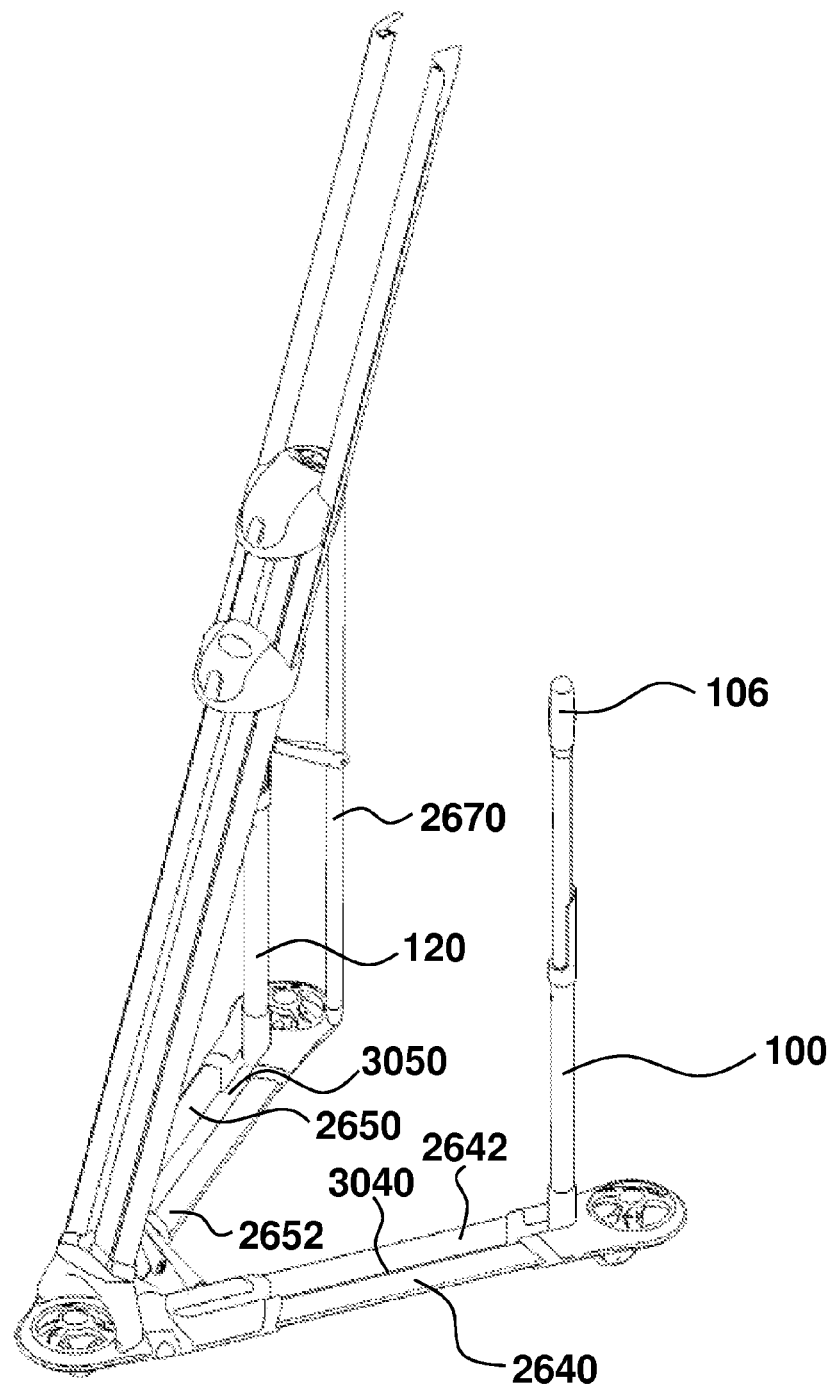
FIG. 30 is a perspective view of a mobility assist IMS with the mobility assist arms in a deployed configuration.
Figure 31:
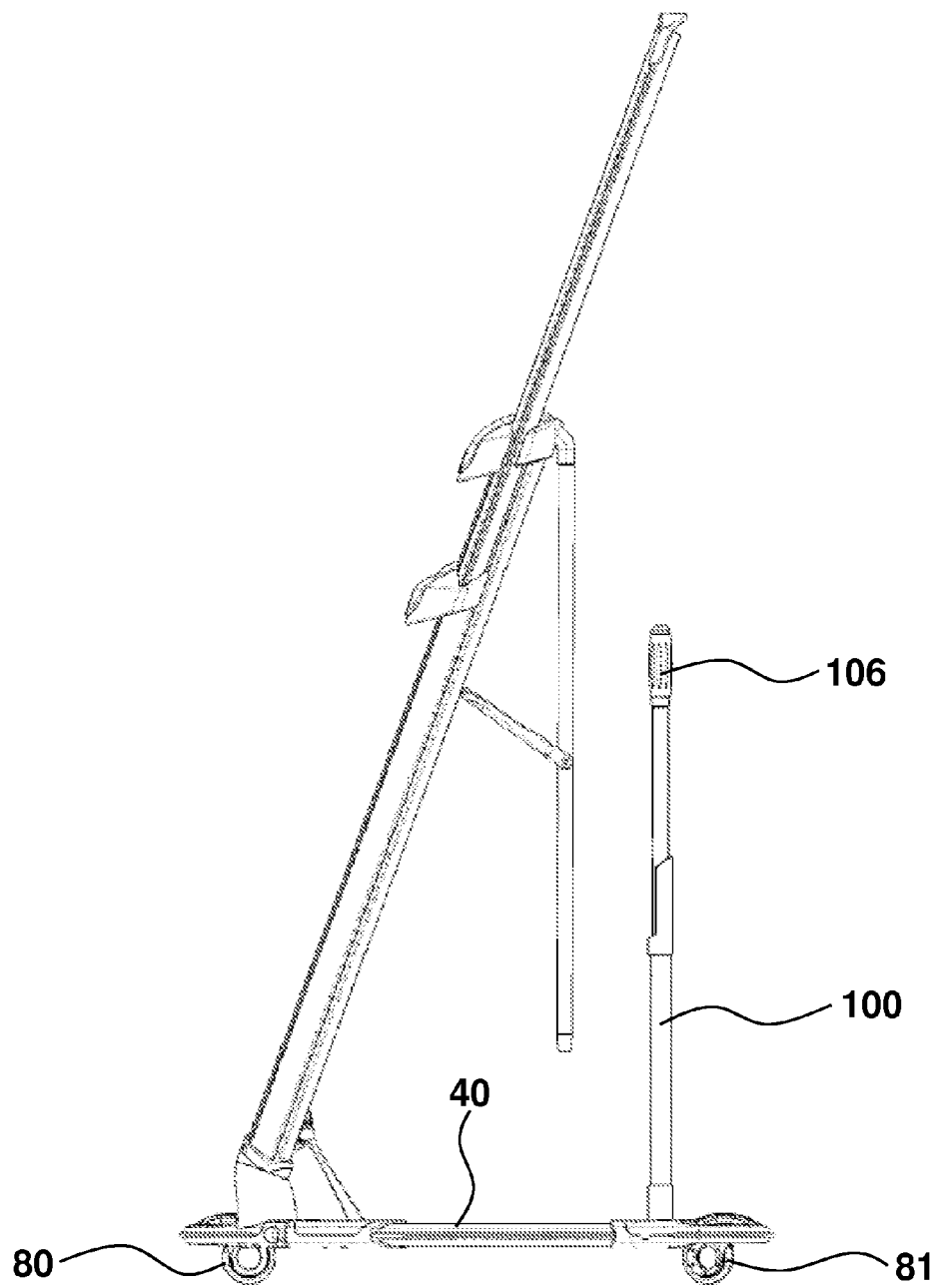
FIG. 31 Side view of the system of FIG. 30.
Figure 32:
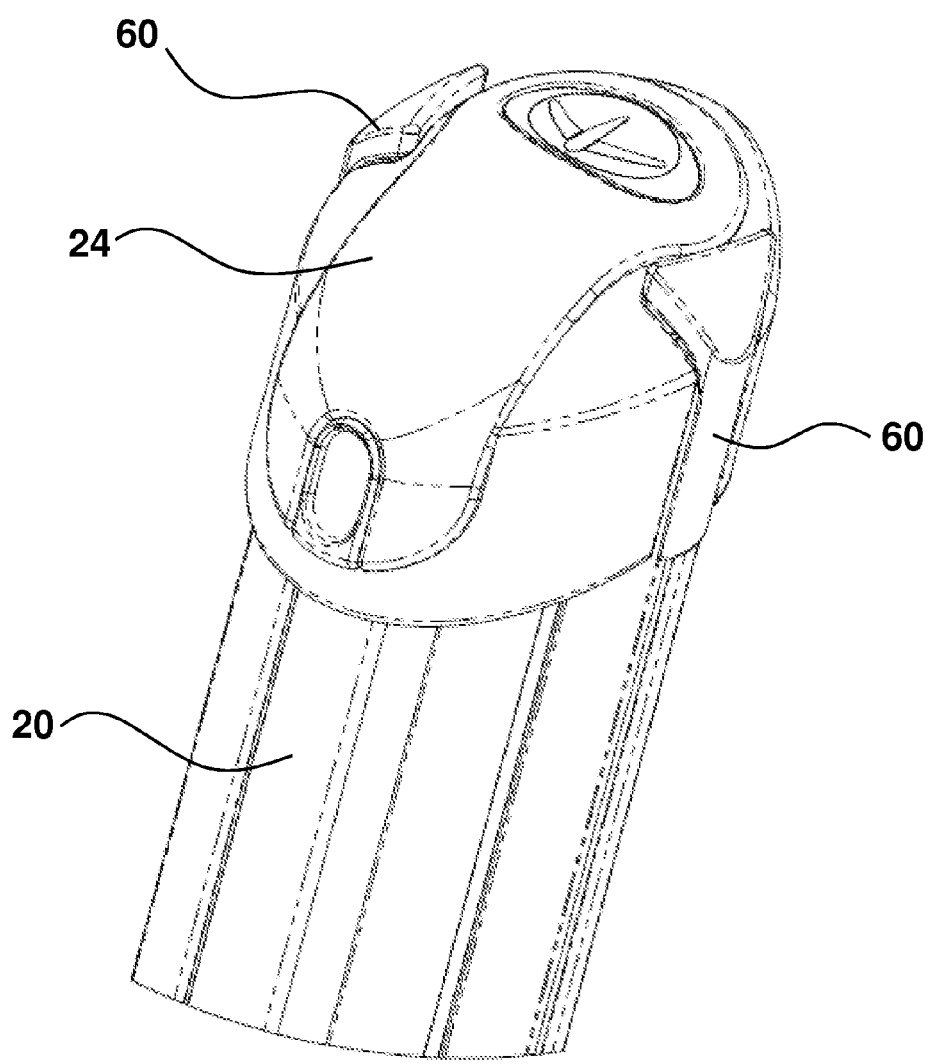
FIG. 32 is a close up view of the trunk top end with the holding arms in a stored position substantially flush with the trunk top end.

Referring to FIGS. 30 and 31, deployment of mobility arms 100 and 120 reveals recesses 3040 and 3050 in each of base arms 40 and 50, respectively. In an aspect the recess corresponds to a complete opening in base arms 40 and 50. Alternatively, a bottom may be provided in each of base arms 40 and 50, such as a floor or ladder-type surface for supporting mobility arms 100 and 120 in their stored configuration. Alternatively, in the embodiment where mobility arms 100 and 120 are not rotably connected to base arms 40 and 50 (e.g., permanently fixed in position, or removably fixed in position such as by threads, tight-fit, or a locking mechanism), recesses in 40 and 50 are unnecessary.

Figure 27:
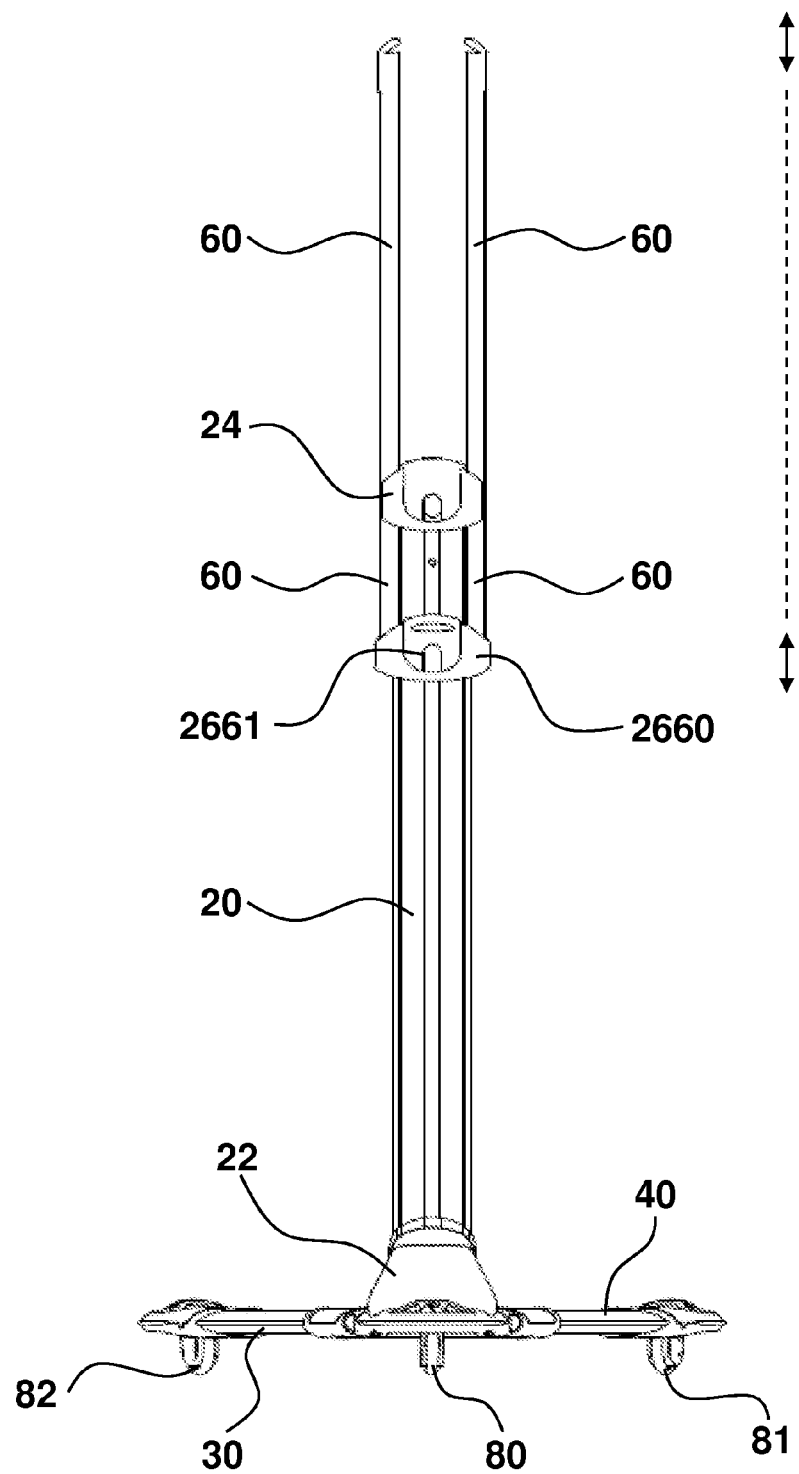
FIG. 27 Front view of the system of FIG. 26.
Figure 28:
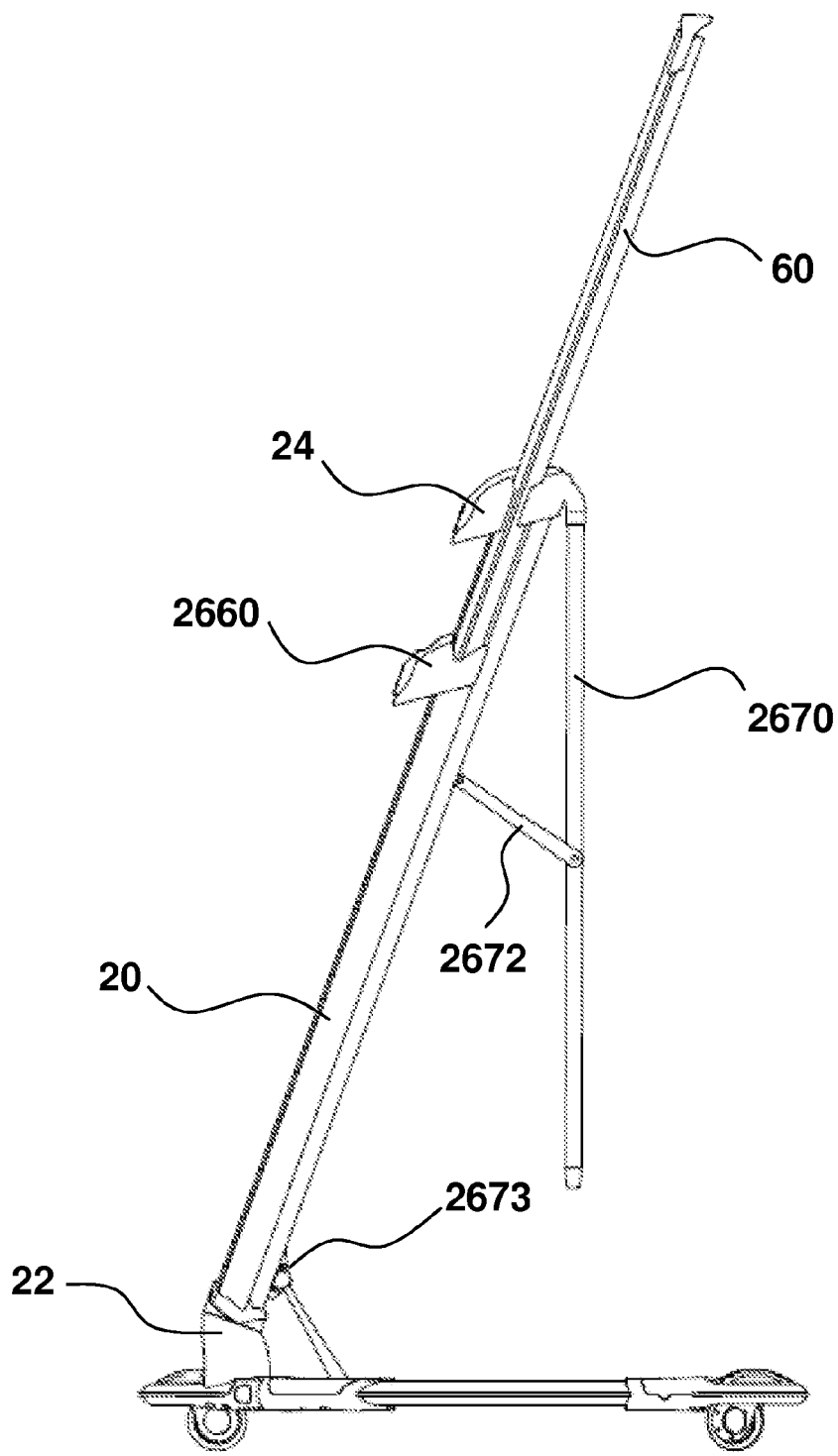
FIG. 28 Side view of the system of FIG. 26.

A comparison of FIGS. 26-28, 33 to FIG. 36 illustrates the deployment mechanism of holding arms 60 by axial movement of handle 2660. Handle 2660 is operably connected to holders 60 such that movement of handle 2660 along trunk 20 results in corresponding movement of holders 60. This is indicated in FIG. 27 by the up/down arrows adjacent to each of 2660 and the top of holding arm 60. The dashed line indicates that motion of one to 2660 or 60 generates a corresponding motion in the other element 60 or 2660, respectively. In this example, two holding arms 60 are provided whose height is controlled by motion of handle 2660. Handle 2660 is infinitely adjustable in that it can be locked in any position along trunk 20 by locking or latch mechanisms known in the art. For example, a locking or latch mechanism may be released by inactivating a holding arm locking mechanism, such as a holding arm lock release button 2661 shown in FIG. 27. Similarly, a latching mechanism may be used as known in the art, such as latches used for car trunk release mechanism, to facilitate movement of holder 2660 along the trunk 20. In a holding arm stored position (see FIGS. 32, 35B, 35C and 36), handle 2660 is positioned to the lowest-possible axial position on trunk 20, corresponding to top of holders 60 being substantially flush or flush with trunk top 24. Trunk top 24 may provide further support to holders 60 by at least partially enclosing holder 60 as holder 60 is maneuvered up/down by slidably moving holder 2660 along trunk 20. A top-view of the systems (FIG. 37) illustrates optional constraint of holding arms 60 by a passage through trunk top 24.

Because handle 2660 is capable of positioning anywhere along trunk 20, the system is versatile in that any item supported by holding arm 60 may be conveniently positioned so as to not hinder the view of a patient that is receiving treatment or support by the IMS. In the examples provided herein (see FIGS. 26-28, and 33), handle 2660 is near the maximum deployed position (e.g., the highest axial position along trunk 20), thereby ensuring any medical device supported by holder 70 does not interfere with a patient who is maneuvering the system, such as by the mobility arms 100 shown in FIG. 30.

In this example, holding arms 60 are both connected to the same handle 2660, so that both arms 60 are simultaneously positioned. In another embodiment, an individual handle 2660 or a positioner may be provided for each holding arm 60, thereby providing independent-positioning for each arm 60. Handle 2660 may also provide a means for a caregiver to help maneuver the unit, or to help collapse the unit, such as by providing a conveniently-shaped for receiving a hand and a related force that either positions the handle 2660 or for lifting the entire collapsed unit and positioning it in its stored configuration, such as affixed to a fastener connected to a wall, hung from a hanger connected to a ceiling or maneuvered and stored within a confined-space.

With respect to the mobility arms 100 and 120 (see FIGS. 30-31) that are optionally rotably engaged with base arms 40 and 50, respectively, arms 100 and 120 lock in a deployed position that is about 90° with respect to horizontal for receiving a user's hands. Mobility arms 100 and 120 are stored either by removing the arms (e.g., for mobility arms that may be removably mated with base arms) or rotating them into a stored position, such as within recesses 3040 and 3050, respectively formed by the split portion of base arms 40 and 50.

Figure 33:
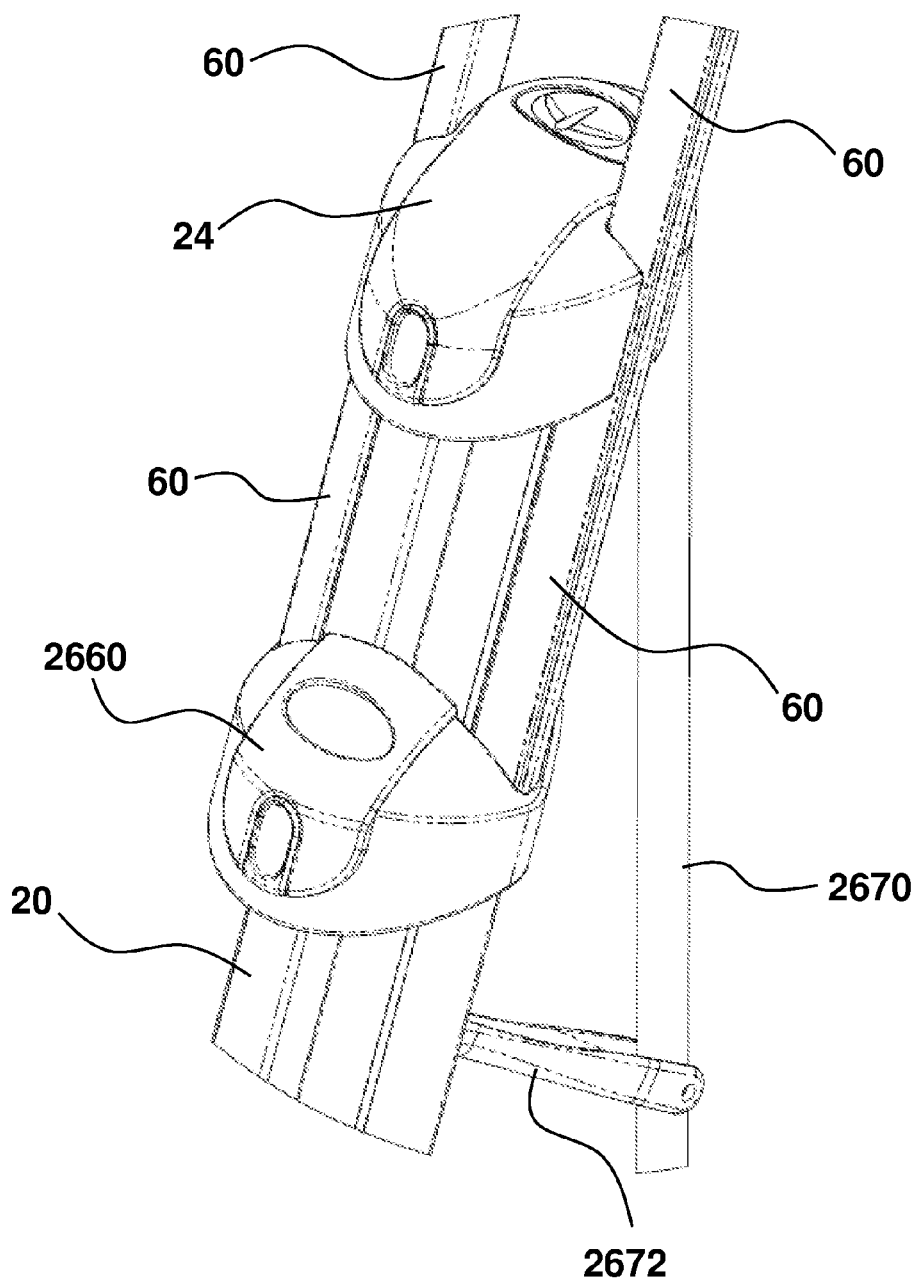
FIG. 33 is a close up view of the trunk top end with the holding arms in a deployed position extending from the trunk top end. Holding arms can be deployed by movement of the holder along the axial length of the trunk.

Optionally, the system is further simplified for ease of use by automatic deployment of pump mount 2670 (see FIGS. 26, 28-30 or equivalently collapsible support 65 of FIG. 1) when the base arms 40 and 50 deploy by operably connecting pump mount 2670 to base arms 40 and/or 50. This connection may be through one or more additional elements, such as a slidable mechanism 2673 that slides along the trunk 20 with base arm 40/50 deployment and to which joint 2672 or mount 2670 is connected (see FIG. 28), such as by a rigid connection element within or along a surface of trunk 20. Such a configuration is an example of an "operable connection" between mount 2670 and base arms 40 and/or 50. Pump mount 2670 provides additional medical device support capacity, such as by support of relatively heavy medical devices such as an infusion pump, power supply, or the like. The capacity of mount 2670 to hold heavier devices is further bolstered by joint 2672 that connects the mount 2670 to the trunk 20 (FIG. 33). Alternatively, pump mount 2670 may be independently deployed from deployment of base arms 40 and 50 as needed and exemplified in Example 1.

Figure 34A:
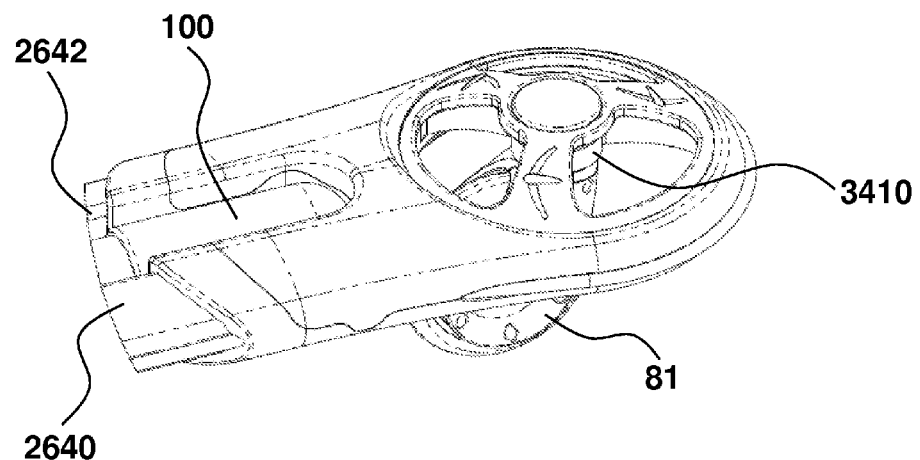
FIG. 34 is a close up view of the various wheel portions of the system illustrated in FIG. 26. A shows the end-portion of the base arms. B shows the trunk bottom portion, vertex region, and other end-portion of the base arms.
Figure 34B:
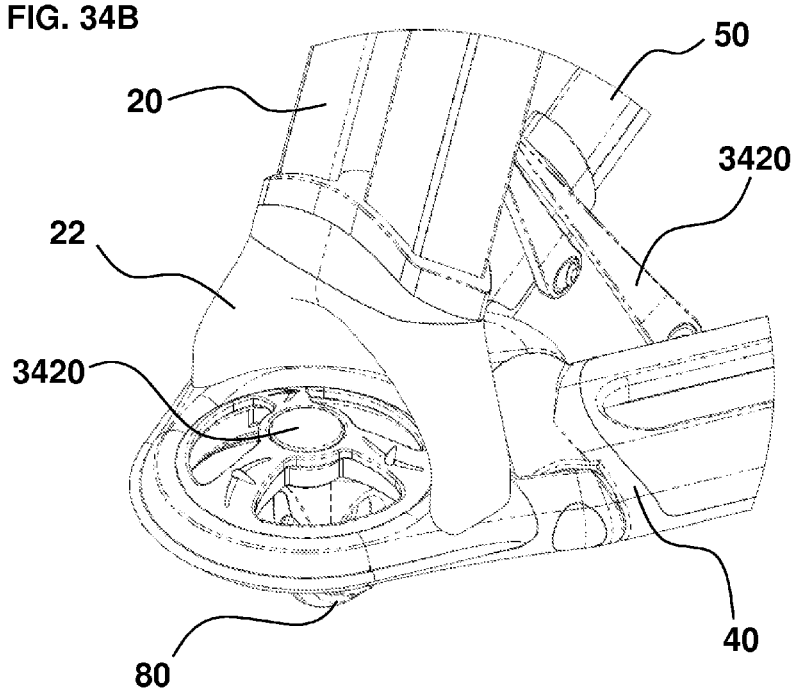
Figure 36:
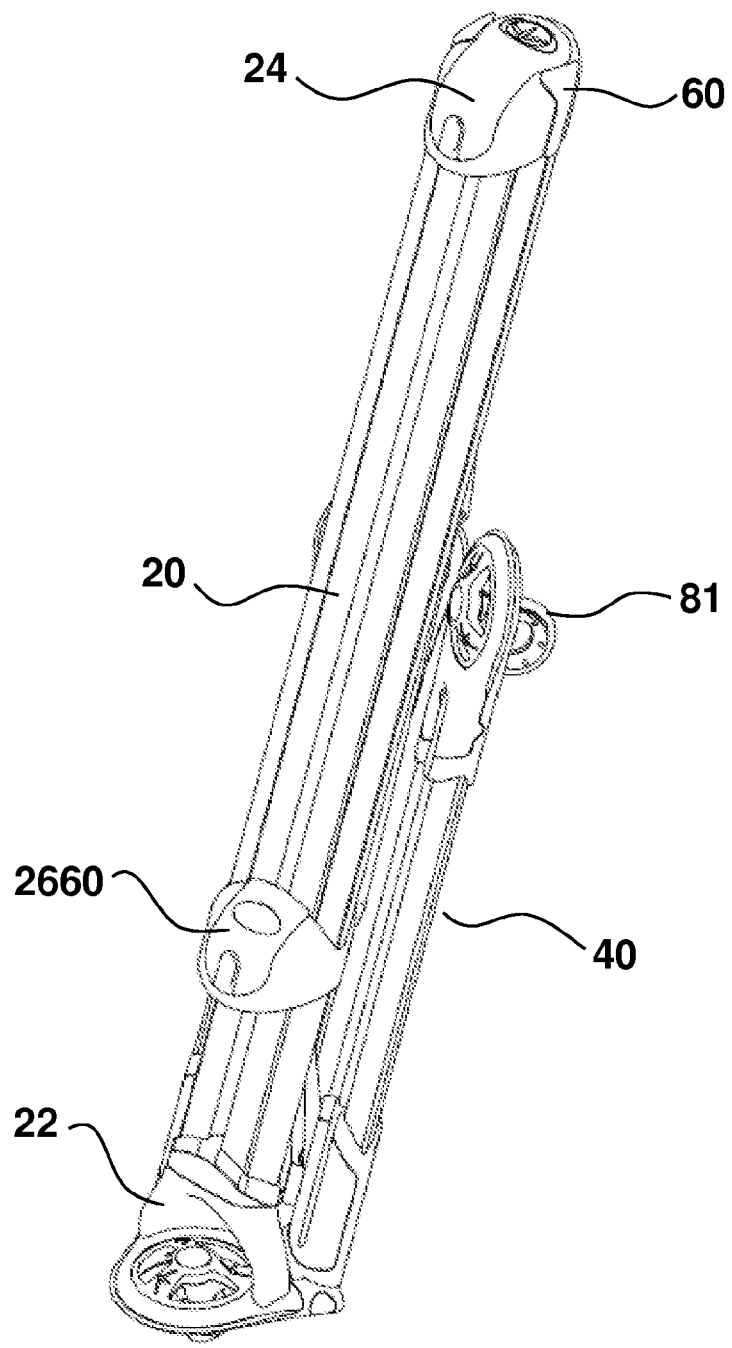
FIG. 36 is a perspective view of the system of FIG. 26 in a stored position.
Figure 37:
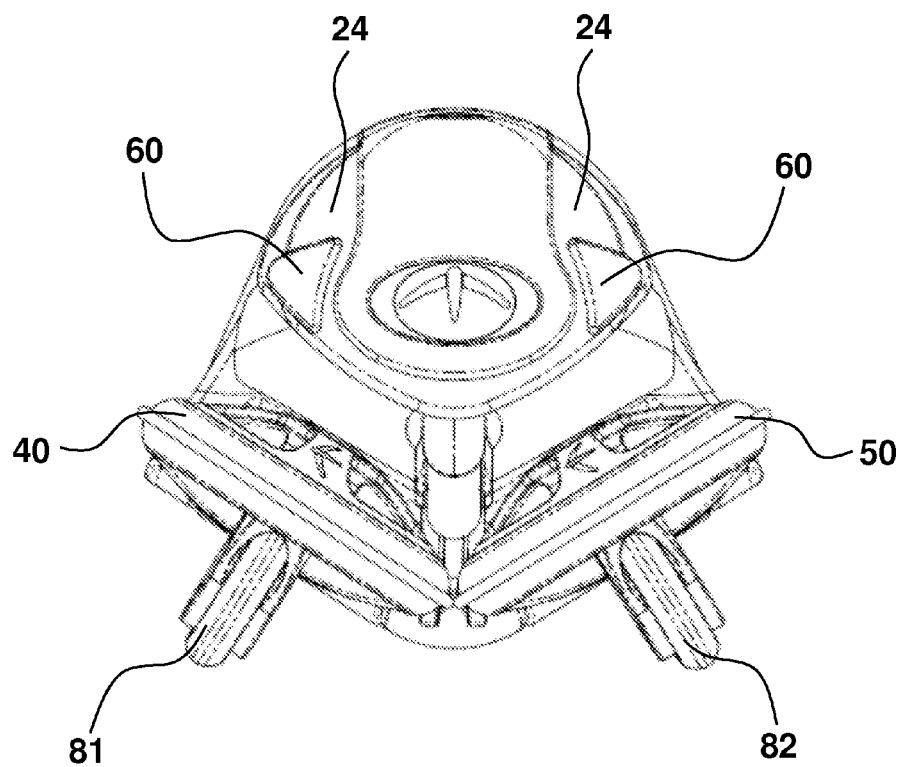
FIG. 37 is a top view of the system of FIG. 26 in a stored position.

Additional support for base arms 40 and 50 upon deployment is provided by arm-trunk joint 3420 that connects each of the base arms 40 and 50 with trunk 20 (FIG. 34B). FIG. 34A is a close-up view of a wheel 81 connected to the end of a base arm 40 or 50. In this example, the wheel is connected to the system by a conventional caster 3410. Referring to FIG. 38A, in the conventional caster embodiment, the wheel 81 need not deploy to a stored configuration, while the base arms 40 and 50 nestle in a position that is substantially parallel to trunk 20. A close-up view of the vertex region, where the base arms 40 and 50 meet trunk bottom 22, in a stored position is provided in FIG. 38B. Having wheel 80 remain in a deployed position, even when stored, provides a convenient means for maneuvering the stored system by rolling the system along the floor via wheel 80.

Figure 39:
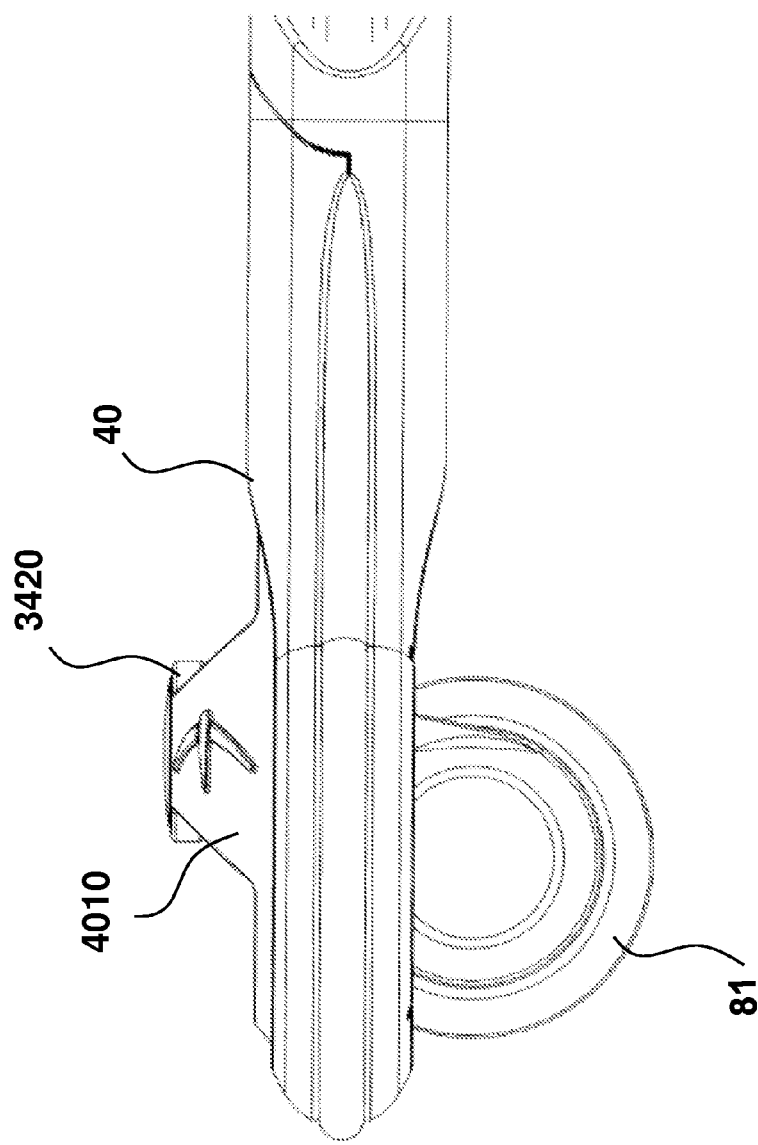
FIGS. 39-40 provide a close-up view of a wheel system connected to a base arm by a conventional caster.
Figure 40:
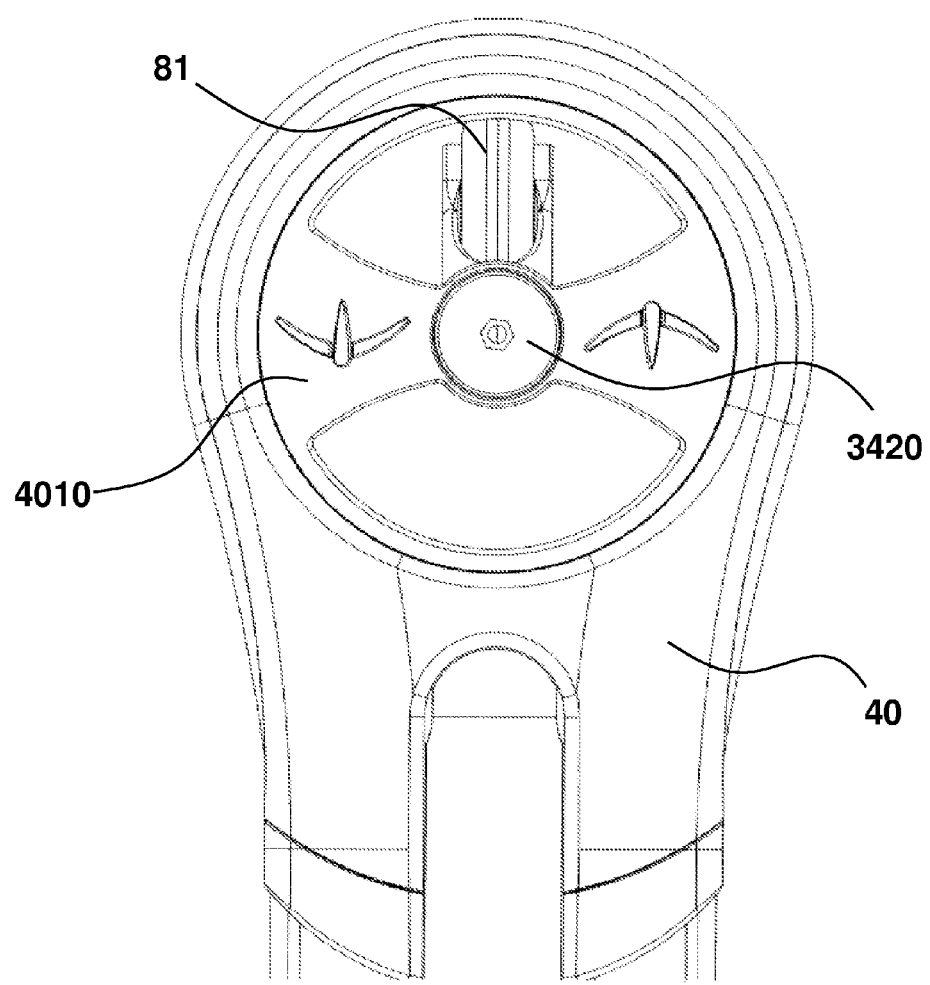

A close-up view of the wheel system is provided in FIGS. 39-40, where a conventional caster 3420 connects wheel 81 to base arm 40. To help prevent unwanted interference with the wheel motion, a multi-spoked wheel connector 4010 optionally connects caster 3420 connection with base arm 40.

Example 6

Offset Vertical Trunk

The construction of a base comprising a pair of base arms 40 and 50 that form a relatively-large base footprint in an IV pole-type setting provides a great deal of flexibility in designing the trunk. For example, FIGS. 1-38 all relate to a trunk that in one manner or another extends over the base footprint by angling at least a portion of the trunk relative to vertical. Another embodiment relates to a substantially vertical trunk, such as a vertical trunk 20 illustrated in FIG. 41.

Figure 41:
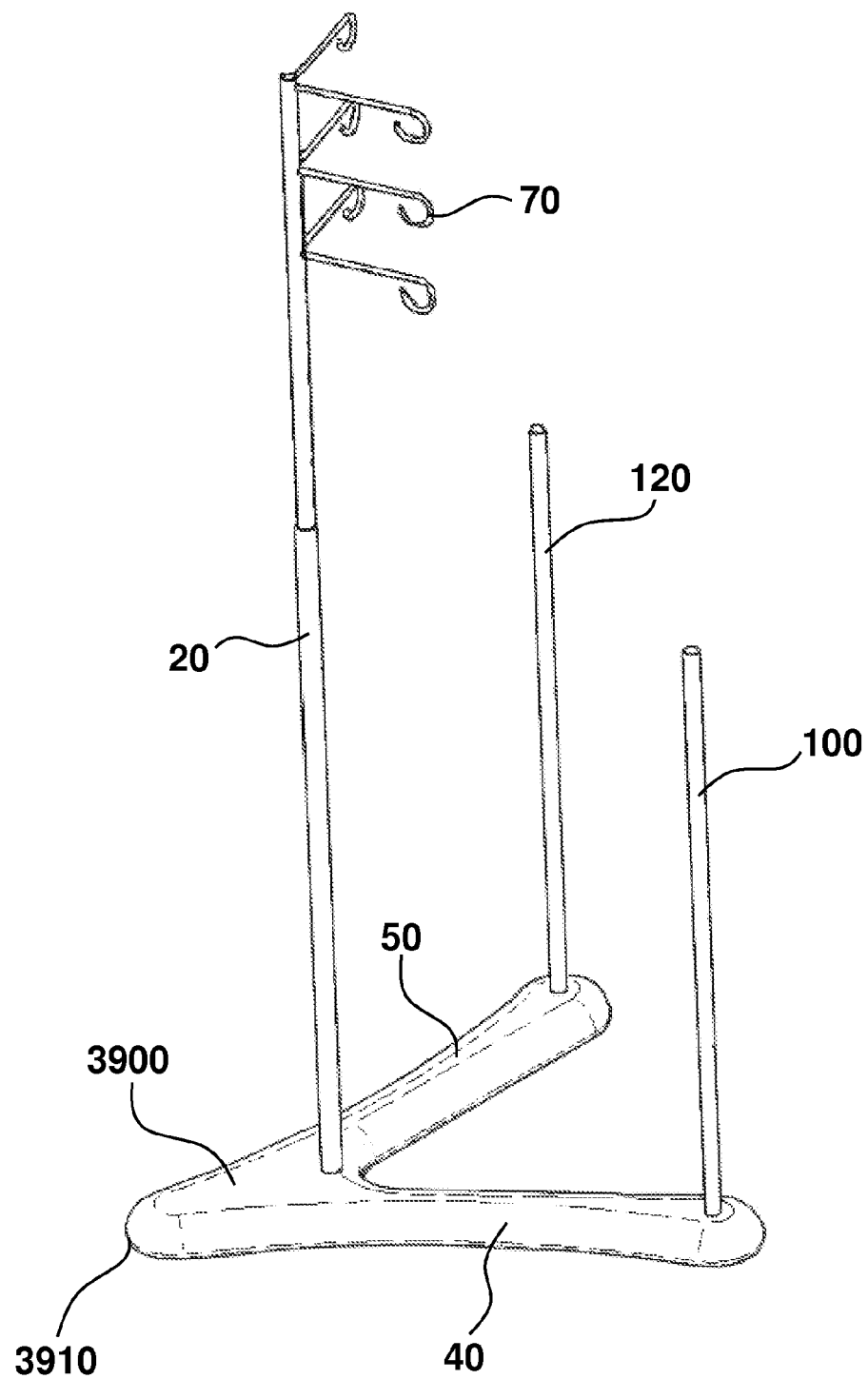
FIG. 41 is a view of a mobility-assist IMS with an offset vertical trunk.

The general configuration in FIG. 41 is similar to the other illustrated embodiments, with base arms 40 and 50 forming a relatively large-area footprint having one-side that is open-ended, with a trunk 20 and mobility arms 100 and 120 connected to base arms 40 and 50. One difference, however, is that trunk 20 is vertical (e.g., 90° with respect to vertical). To provide added stability, vertex region 3900 may extend past the point at which trunk 20 meets the base. This configuration is referred to as a "distal extension" of vertex region 3900 relative to trunk 20.

"Vertex region" refers to the base footprint vertex from which the first and second base arms extend, such as the region from which the front wheel connects. Vertex region is generally the vertex opposite the open-ended side of the base footprint. Accordingly, the vertex region may be an integral part of each of the base arms, or may refer to a separate piece to which the base arms and/or trunk bottom attach. In particular, vertex region refers to the region from which where the trunk extends and the base arms meet. In an aspect, the vertex region extends significantly past the trunk 20 (FIG. 41). The vertex region 3990 depicted in FIG. 41 has a front edge 3910 that extends to a position that is distal to the trunk 20.

The various arms such as holding arms 60 and mobility arms 100 and 120 are exemplified as being not connected to one another. In an embodiment, however, the top ends of holding arms 60 are connected to each other, thereby providing additional support as well as another location for supporting or hanging any one or more medical devices. Similarly, mobility arms 100 and 120 are optionally connected to each other, such as by a rigid bar for example, The bar can provide another location for receiving a patient's hands in a fashion similar to the bar on conventional shopping carts, for example.

We claim:

1. An infusion management mobility assistance device comprising:
   a trunk having one or more holders capable of holding one or more medical components, said trunk having a bottom end and a top end;
   a base comprising a first base arm and a second base arm to form a two-sided base footprint with a vertex region, wherein one end of each of the first and second base arms connect to form the vertex region, wherein each of the base arms are pivotally connected to the trunk for pivoting each of the base arms into a base-storage or a base-deployed configuration, and wherein said trunk bottom end connects to said base at said vertex region and said trunk forms an acute angle with respect to said base, and the device center of gravity is located over the two-sided base footprint;
   a mount connected to said trunk, wherein said mount is configured to support one or more medical devices;
   a first wheel connected to said vertex region;
   a second wheel connected to said first base arm;
   a third wheel connected to said second base arm, wherein each of the wheels are capable of stably contacting a supporting surface on which the system rests;
   a first mobility handle connected to said trunk for supporting one hand of a patient; and
   a second mobility handle connected to said trunk for supporting the other hand of the patient;
   wherein the mobility handles are configured to receive an applied force to stably ambulate the device over a supporting surface under the applied force while being extremely tip resistant.

2. The device of claim 1 wherein said vertex region has a front edge that extends to a position that is distal to said trunk.

3. The device of claim 1, wherein each of the mobility handles are removable.

4. The device of claim 1, wherein said acute angle is less than or equal to 85° and greater than or equal to 70°.

5. The device of claim 1, wherein each wheel contact point corresponds to a vertex of a triangular base footprint, said footprint having an area that is selected from a range of between about 1600 cm$^2$ and 4800 cm$^2$.

6. The device of claim 1 wherein the first base arm and second base form a base vertex angle, wherein said base vertex angle is greater than or equal to 50° and less than or equal to 90°.

7. The device of claim 1, further comprising a holding arm operably connected to said trunk top end for supporting one or more medical components.

8. The device of claim 7, wherein said holding arm is height-adjustable.

9. The device of claim 8, further comprising a handle, wherein
   said handle is operably connected to said holding arm; and
   said handle is slideably connected to said trunk, so that said handle is capable of axial travel along said trunk, wherein said slideable axial travel provides said height-adjustability.

10. The device of claim 1, wherein said mount is a pump mount for supporting an infusion pump.

11. The device of claim 10, wherein said pump mount is operably connected to said base arms so that deploying said base arms automatically deploys said pump mount.

12. The device of claim 1, further comprising a connector to connect the first and second mobility handles to the trunk, the connector having one end connected to the trunk and another end connected to each of the first and second mobility handles.

13. The device of claim 1, wherein each of the first and second mobility handles connect to and extend from the trunk.

14. The device of claim 1, wherein multiple medical components are attached to the infusion management mobility assistance device, the multiple medical components comprising an intravenous fluid bag, an infusion pump and an oxygen canister.

15. The device of claim 14, wherein the multiple medical components further comprise a catheter bag.

16. The device of claim 1, further comprising an electrical system for providing power to an electrical component attached to the infusion management mobility assistance device.

17. The device of claim 1, further comprising an additional wheel connected to the infusion management mobility assistance device.

18. The device of claim 12, wherein in a base storage configuration the mobility handles are parallel to the trunk.

19. The device of claim 13, wherein in a base storage configuration the mobility handles are parallel to the trunk.

20. The device of claim 1, wherein the mobility handles are rotably connected to said trunk and configured to provide a deployed configuration to receive an applied force from a user to ambulate the device over a supporting surface and a stored configuration with the base arms and mobility handles parallel to the trunk.

* * * * *